(12) United States Patent
Vivien et al.

(10) Patent No.: US 9,732,334 B2
(45) Date of Patent: Aug. 15, 2017

(54) MUTATED TISSUE PLASMINOGEN ACTIVATORS AND USES THEREOF

(71) Applicants: Denis Vivien, Caen (FR); Jerome Parcq, Caen (FR)

(72) Inventors: Denis Vivien, Caen (FR); Jerome Parcq, Caen (FR)

(73) Assignees: Institut National de la Sante et de la Recherche Medicale (INSERM), Paris (FR); Universite de Caen Basse Normandie, Caen (FR)

( * ) Notice: Subject to any disclaimer, the term of this patent is extended or adjusted under 35 U.S.C. 154(b) by 0 days.

(21) Appl. No.: 14/972,268

(22) Filed: Dec. 17, 2015

(65) Prior Publication Data

US 2016/0194623 A1 Jul. 7, 2016

Related U.S. Application Data

(62) Division of application No. 14/342,164, filed as application No. PCT/EP2012/067540 on Sep. 7, 2012, now Pat. No. 9,249,406.

(30) Foreign Application Priority Data

Sep. 8, 2011 (EP) .................................... 11306119

(51) Int. Cl.
| | |
|---|---|
| C12N 5/071 | (2010.01) |
| C12N 5/10 | (2006.01) |
| C12P 21/06 | (2006.01) |
| C12P 19/34 | (2006.01) |
| C12N 15/00 | (2006.01) |
| C12N 9/64 | (2006.01) |
| C12N 9/48 | (2006.01) |
| C07H 21/04 | (2006.01) |
| C07K 1/00 | (2006.01) |
| C12N 9/72 | (2006.01) |

(52) U.S. Cl.
CPC .... *C12N 9/6459* (2013.01); *C12Y 304/21068* (2013.01)

(58) Field of Classification Search
CPC ...................... C12Y 304/21068; C12N 9/6459

USPC .......... 435/369, 359, 69.1, 91.1, 320.1, 226, 435/212; 536/23.1, 23.2; 530/350
See application file for complete search history.

(56) References Cited

U.S. PATENT DOCUMENTS 5,770,426 A 6/1998 Anderson et al.

FOREIGN PATENT DOCUMENTS

| EP | 0 275 606 A1 | 7/1988 |
|---|---|---|
| EP | 0 462 651 A1 | 12/1991 |
| WO | 9004635 A1 | 5/1990 |
| WO | 2007/047995 A2 | 10/2007 |

OTHER PUBLICATIONS

"t-PA/u-PA-e", Database Geneseq, Mar. 26, 1992, Web.
"Sequence 222 from Patent WO2007047995", Database EPA Proteins, Jun. 26, 2007, Web.
Yepes et al., "Tissue-type plasminogen activator in the ischemic brain: more than a thrombolytic", Trends in Neuroscience, Jan. 1, 2009, pp. 48-55, vol. 32, No. 1, Elsevier, Amsterdam, NL.
Sugiki et al., "Downregulation of urokinase-type and tissue-type plasminogen activators in a rabbit model of renal schemia/reperfusion", Journal of Biochemistry (Tokyo), Sep. 2002, pp. 501-508, vol. 132, No. 3.
Liberatore et al., "Vampire Bat Salivary Plasminogen Activator (Desmoteplase) a Unique Fibrinolytic Enzyme That Does Not Promote Neurodegeneration", Stroke, Feb. 1, 2003, pp. 537-543, vol. 34, No. 2, Lippincott Williams & Wilkins, US.
Broun et al., "Catalytic plasticity of fatty acid modification enzymes underlying chemical diversity of plant lipids", Science, 1998, pp. 1315-1317, vol. 282.
Chica et al., "Semi-rational approaches to engineering enzyme activity: combining the benefits of directed evolution and rational design", Curr. Opi. Biotechnol., 2005, pp. 378-384, vol. 16.
Devos et al., "Practical limits of function prediction", Proteins: Structure, Function, and Genetics, 200, pp. 98-107, vol. 41.
Seffernick et al., "Melamine deaminase and Atrazine chlorohydrolase: 98 percent identical but functionally different", J. Bacteriol., 2001, pp. 2405-2410, vol. 183, No. 8.

*Primary Examiner* — Ganapathirama Raghu
(74) *Attorney, Agent, or Firm* — Whitham, Curtis & Cook, P.C.

(57) ABSTRACT

The present invention relates to mutated tissue plasminogen activators, and their use for treating thrombotic diseases.

4 Claims, 17 Drawing Sheets

| Name | Domain structure | Two-chain form | Homology to rat tPA (identical matches / conserved substitution) |
|---|---|---|---|
| Human tPA | F E K1 K2 SP | Yes | 81 % / 89 % |
| Rat tPA | F E K1 K2 SP | Yes | 100 % / 100 % |
| Desmodus rotundus plasminogen activator (DSPAα1) | F E K1 SP | No | 67 % / 79 % |

Figure 1A

```
Rat-tPA-K1  LSQKPYSARRPNAIKLGLGNHNYCRNPDRDTKPWCYVFKAGKYTTFCSTPAC  SEQ ID NO: 40
DSPA-K      LTRRTYNGRMPDAFNLGLGNHNYCRNHNGAPKPWCYVIKAGKFSSCSVPVC  SEQ ID NO: 41
Rat-tPA-K2  LIGKTYTAWRANSQALGLGRHNYCRNPDGDAKPWCHVMKDRKLWYYCDMSPC  SEQ ID NO: 42
            *  :.*..  .::  ****.*******:  ****:*:*  *   *. . *
```

Figure 2A

```
                 270|     |280|       |
Rat-tPA   GLRQYKQPQFRIKGGLFTDIT   SEQ ID NO: 43
Hu-tPA    GLRQYSQPQFRIHGGLFADIA   SEQ ID NO: 27
DSPA-a1   GLRKYKEPQIHSTGGLFTDIT   SEQ ID NO: 44
          ***:*.:**.:. .****:**:
```

Figure 2B

| Name | Domain structure | Two-chain form | Modification relative to wt-tPA |
|---|---|---|---|
| Rat wt-tPA |  | Yes | |
| Rat ΔK2-tPA |  | Yes | Suppression of the kringle 2 domain (AA181-262) |
| Rat K2*-tPA | 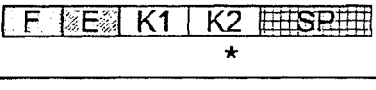 | Yes | Trp254Arg |
| Rat sc*-tPA | 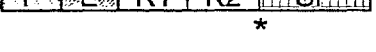 | No | Arg276Ser |
Figure 13

| Name | Sequence / mutation | two-chain form | amidolytic activity | fibrinolytic activity | | | |
|---|---|---|---|---|---|---|---|
| | | | | IU/mg[2] | Kd[3] (nM) | Km[4] (µM) | kcat/Km[4] (nM$^{-1}$.s$^{-1}$) |
| Hu tPA | UniProtKB: P00750 | yes | yes | | | | |
| DSPAα1 | UniProtKB: P98119 | no | limited | | | | |
| rat wt-tPA | UniProtKB: P19637 [1] | yes | yes | 203 605 | 0.26 | 0.024 | 0.022 |
| rat sc*-tPA | Arg276/Ser | no | limited | 184 136 | 1.20 | 0.044 | 0.0026 |
| rat K2*-tPA | Tryp254/Arg | yes | yes | 155 559 | 0.50 | 0.037 | 0.0042 |
| rat ΔK2-tPA | Cys181 to Cys262 deletion | yes | yes | 319 903 | 0.82 | 0.045 | 0.0031 |

Figure 14

SEQUENCE LISTING

```
<160> NUMBER OF SEQ ID NOS: 46

<210> SEQ ID NO 1
<211> LENGTH: 562
<212> TYPE: PRT
<213> ORGANISM: Homo sapiens

<400> SEQUENCE: 1

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ser Tyr Gln Val Ile Cys Arg Asp Glu Lys Thr Gln Met
            35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
    130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
        275                 280                 285

Glu Tyr Cys Asp Val Pro Ser Cys Ser Thr Cys Gly Leu Arg Gln Tyr
    290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
```

```
                        340                 345                 350
Leu Ser Ala Ala His Cys Phe Gln Glu Arg Phe Pro Pro His His Leu
                355                 360                 365

Thr Val Ile Leu Gly Arg Thr Tyr Arg Val Val Pro Gly Glu Glu Glu
        370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
                420                 425                 430

Pro Ala Asp Leu Gln Leu Pro Asp Trp Thr Glu Cys Glu Leu Ser Gly
                435                 440                 445

Tyr Gly Lys His Glu Ala Leu Ser Pro Phe Tyr Ser Glu Arg Leu Lys
                450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
                500                 505                 510

Ser Gly Gly Pro Leu Val Cys Leu Asn Asp Gly Arg Met Thr Leu Val
                515                 520                 525

Gly Ile Ile Ser Trp Gly Leu Gly Cys Gly Gln Lys Asp Val Pro Gly
                530                 535                 540

Val Tyr Thr Lys Val Thr Asn Tyr Leu Asp Trp Ile Arg Asp Asn Met
545                 550                 555                 560

Arg Pro

<210> SEQ ID NO 2
<211> LENGTH: 527
<212> TYPE: PRT
<213> ORGANISM: Homo sapiens

<400> SEQUENCE: 2

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
                20                  25                  30

Tyr Cys Trp Cys Asn Ser Gly Arg Ala Gln Cys His Ser Val Pro Val
            35                  40                  45

Lys Ser Cys Ser Glu Pro Arg Cys Phe Asn Gly Gly Thr Cys Gln Gln
        50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
```

```
            145                 150                 155                 160
        Gly Lys Tyr Ser Ser Glu Phe Cys Ser Thr Pro Ala Cys Ser Glu Gly
                        165                 170                 175

Asn Ser Asp Cys Tyr Phe Gly Asn Gly Ser Ala Tyr Arg Gly Thr His
                        180                 185                 190

Ser Leu Thr Glu Ser Gly Ala Ser Cys Leu Pro Trp Asn Ser Met Ile
                        195                 200                 205

Leu Ile Gly Lys Val Tyr Thr Ala Gln Asn Pro Ser Ala Gln Ala Leu
                210                 215                 220

Gly Leu Gly Lys His Asn Tyr Cys Arg Asn Pro Asp Gly Asp Ala Lys
        225                 230                 235                 240

Pro Trp Cys His Val Leu Lys Asn Arg Arg Leu Thr Trp Glu Tyr Cys
                        245                 250                 255

Asp Val Pro Ser Cys Ser Thr Cys Gly Leu Arg Gln Tyr Ser Gln Pro
                        260                 265                 270

Gln Phe Arg Ile Lys Gly Gly Leu Phe Ala Asp Ile Ala Ser His Pro
                        275                 280                 285

Trp Gln Ala Ala Ile Phe Ala Lys His Arg Arg Ser Pro Gly Glu Arg
                        290                 295                 300

Phe Leu Cys Gly Gly Ile Leu Ile Ser Ser Cys Trp Ile Leu Ser Ala
        305                 310                 315                 320

Ala His Cys Phe Gln Glu Arg Phe Pro Pro His His Leu Thr Val Ile
                        325                 330                 335

Leu Gly Arg Thr Tyr Arg Val Val Pro Gly Glu Glu Glu Gln Lys Phe
                        340                 345                 350

Glu Val Glu Lys Tyr Ile Val His Lys Glu Phe Asp Asp Asp Thr Tyr
                        355                 360                 365

Asp Asn Asp Ile Ala Leu Leu Gln Leu Lys Ser Asp Ser Ser Arg Cys
                        370                 375                 380

Ala Gln Glu Ser Ser Val Val Arg Thr Val Cys Leu Pro Pro Ala Asp
        385                 390                 395                 400

Leu Gln Leu Pro Asp Trp Thr Glu Cys Glu Leu Ser Gly Tyr Gly Lys
                        405                 410                 415

His Glu Ala Leu Ser Pro Phe Tyr Ser Glu Arg Leu Lys Glu Ala His
                        420                 425                 430

Val Arg Leu Tyr Pro Ser Ser Arg Cys Thr Ser Gln His Leu Leu Asn
                        435                 440                 445

Arg Thr Val Thr Asp Asn Met Leu Cys Ala Gly Asp Thr Arg Ser Gly
                450                 455                 460

Gly Pro Gln Ala Asn Leu His Asp Ala Cys Gln Gly Asp Ser Gly Gly
        465                 470                 475                 480

Pro Leu Val Cys Leu Asn Asp Gly Arg Met Thr Leu Val Gly Ile Ile
                        485                 490                 495

Ser Trp Gly Leu Gly Cys Gly Gln Lys Asp Val Pro Gly Val Tyr Thr
                        500                 505                 510

Lys Val Thr Asn Tyr Leu Asp Trp Ile Arg Asp Asn Met Arg Pro
                        515                 520                 525

<210> SEQ ID NO 3
<211> LENGTH: 559
<212> TYPE: PRT
<213> ORGANISM: Rattus norvegicus

<400> SEQUENCE: 3
```

-continued

```
Met Lys Gly Glu Leu Leu Cys Val Leu Leu Cys Gly Val Ala Phe
1               5                   10                  15

Thr Leu Pro Asp Gln Gly Ile His Arg Arg Phe Arg Arg Gly Ala Arg
            20                  25                  30

Ser Tyr Arg Ala Thr Cys Arg Asp Glu Gln Thr Gln Thr Thr Tyr Gln
        35                  40                  45

Gln His Gln Ser Trp Leu Arg Pro Met Leu Arg Gly Asn Arg Val Glu
    50                  55                  60

Tyr Cys Arg Cys Asn Ser Gly Leu Ala Gln Cys His Ser Val Pro Val
65                  70                  75                  80

Arg Ser Cys Ser Glu Pro Arg Cys Phe Asn Gly Gly Thr Cys Gln Gln
                85                  90                  95

Ala Leu Tyr Phe Ser Asp Phe Val Cys Gln Cys Pro Asp Gly Phe Val
            100                 105                 110

Gly Lys Arg Cys Asp Ile Asp Thr Arg Ala Thr Cys Phe Glu Gly Gln
        115                 120                 125

Gly Ile Thr Tyr Arg Gly Thr Trp Ser Thr Ala Glu Asn Gly Ala Glu
    130                 135                 140

Cys Ile Asn Trp Asn Ser Ser Ala Leu Ser Gln Lys Pro Tyr Ser Ala
145                 150                 155                 160

Arg Arg Pro Asn Ala Ile Lys Leu Gly Leu Gly Asn His Asn Tyr Cys
                165                 170                 175

Arg Asn Pro Asp Arg Asp Val Arg Pro Trp Cys Tyr Val Phe Lys Ala
            180                 185                 190

Gly Lys Tyr Thr Thr Glu Phe Cys Ser Thr Pro Ala Cys Pro Lys Gly
        195                 200                 205

Pro Thr Glu Asp Cys Tyr Val Gly Lys Gly Val Thr Tyr Arg Gly Thr
    210                 215                 220

His Ser Phe Thr Thr Ser Lys Ala Ser Cys Leu Pro Trp Asn Ser Met
225                 230                 235                 240

Ile Leu Ile Gly Lys Thr Tyr Thr Ala Trp Arg Ala Asn Ser Gln Ala
                245                 250                 255

Leu Gly Leu Gly Arg His Asn Tyr Cys Arg Asn Pro Asp Gly Asp Ala
            260                 265                 270

Lys Pro Trp Cys His Val Met Lys Asp Arg Lys Leu Thr Arg Glu Tyr
        275                 280                 285

Cys Asp Met Ser Pro Cys Ser Thr Cys Gly Leu Arg Gln Tyr Lys Gln
    290                 295                 300

Pro Leu Phe Arg Ile Lys Gly Gly Leu Phe Thr Asp Ile Thr Ser His
305                 310                 315                 320

Pro Trp Gln Ala Ala Ile Phe Val Lys Asn Lys Arg Ser Pro Gly Glu
                325                 330                 335

Arg Phe Leu Cys Gly Gly Val Leu Ile Ser Ser Cys Trp Val Leu Ser
            340                 345                 350

Ala Ala His Cys Phe Val Glu Arg Phe Pro Pro His His Leu Lys Val
        355                 360                 365

Val Leu Gly Arg Thr Tyr Arg Val Val Pro Gly Glu Glu Gln Thr
    370                 375                 380

Phe Glu Ile Glu Lys Tyr Ile Val His Lys Glu Phe Asp Asp Asp Thr
385                 390                 395                 400

Tyr Asp Asn Asp Ile Ala Leu Leu Gln Leu Arg Ser Asp Ser Ser Gln
                405                 410                 415

Cys Ala Gln Glu Ser Ser Ser Val Gly Thr Ala Cys Leu Pro Asp Pro
```

```
                   420                 425                 430
Asp Val Gln Leu Pro Asp Trp Thr Glu Cys Glu Leu Ser Gly Tyr Gly
                435                 440                 445

Lys His Glu Ala Ser Ser Pro Phe Phe Ser Asp Arg Leu Lys Glu Ala
450                 455                 460

His Val Arg Leu Tyr Pro Ser Ser Arg Cys Thr Ser Gln His Leu Phe
465                 470                 475                 480

Asn Lys Thr Ile Thr Ser Asn Met Leu Cys Ala Gly Asp Thr Arg Thr
                485                 490                 495

Gly Gly Asn Gln Asp Val His Asp Ala Cys Gln Gly Asp Ser Gly Gly
                500                 505                 510

Pro Leu Val Cys Met Ile Asp Lys Arg Met Thr Leu Leu Gly Ile Ile
                515                 520                 525

Ser Trp Gly Leu Gly Cys Gly Gln Lys Asp Val Pro Gly Ile Tyr Thr
                530                 535                 540

Lys Val Thr Asn Tyr Leu Asn Trp Ile Gln Asp Asn Met Lys Gln
545                 550                 555

<210> SEQ ID NO 4
<211> LENGTH: 527
<212> TYPE: PRT
<213> ORGANISM: Rattus norvegicus

<400> SEQUENCE: 4

Ser Tyr Arg Ala Thr Cys Arg Asp Glu Gln Thr Gln Thr Thr Tyr Gln
1               5                   10                  15

Gln His Gln Ser Trp Leu Arg Pro Met Leu Arg Gly Asn Arg Val Glu
                20                  25                  30

Tyr Cys Arg Cys Asn Ser Gly Leu Ala Gln Cys His Ser Val Pro Val
            35                  40                  45

Arg Ser Cys Ser Glu Pro Arg Cys Phe Asn Gly Gly Thr Cys Gln Gln
        50                  55                  60

Ala Leu Tyr Phe Ser Asp Phe Val Cys Gln Cys Pro Asp Gly Phe Val
65              70                  75                  80

Gly Lys Arg Cys Asp Ile Asp Thr Arg Ala Thr Cys Phe Glu Gly Gln
                85                  90                  95

Gly Ile Thr Tyr Arg Gly Thr Trp Ser Thr Ala Glu Asn Gly Ala Glu
                100                 105                 110

Cys Ile Asn Trp Asn Ser Ser Ala Leu Ser Gln Lys Pro Tyr Ser Ala
            115                 120                 125

Arg Arg Pro Asn Ala Ile Lys Leu Gly Leu Gly Asn His Asn Tyr Cys
        130                 135                 140

Arg Asn Pro Asp Arg Asp Val Arg Pro Trp Cys Tyr Val Phe Lys Ala
145                 150                 155                 160

Gly Lys Tyr Thr Thr Glu Phe Cys Ser Thr Pro Ala Cys Pro Lys Gly
                165                 170                 175

Pro Thr Glu Asp Cys Tyr Val Gly Lys Gly Val Thr Tyr Arg Gly Thr
                180                 185                 190

His Ser Phe Thr Thr Ser Lys Ala Ser Cys Leu Pro Trp Asn Ser Met
            195                 200                 205

Ile Leu Ile Gly Lys Thr Tyr Thr Ala Trp Arg Ala Asn Ser Gln Ala
        210                 215                 220

Leu Gly Leu Gly Arg His Asn Tyr Cys Arg Asn Pro Asp Gly Asp Ala
225                 230                 235                 240
```

```
Lys Pro Trp Cys His Val Met Lys Asp Arg Lys Leu Thr Arg Glu Tyr
            245                 250                 255

Cys Asp Met Ser Pro Cys Ser Thr Cys Gly Leu Arg Gln Tyr Lys Gln
            260                 265                 270

Pro Leu Phe Arg Ile Lys Gly Gly Leu Phe Thr Asp Ile Thr Ser His
            275                 280                 285

Pro Trp Gln Ala Ala Ile Phe Val Lys Asn Lys Arg Ser Pro Gly Glu
            290                 295                 300

Arg Phe Leu Cys Gly Gly Val Leu Ile Ser Ser Cys Trp Val Leu Ser
305                 310                 315                 320

Ala Ala His Cys Phe Val Glu Arg Phe Pro Pro His His Leu Lys Val
                325                 330                 335

Val Leu Gly Arg Thr Tyr Arg Val Val Pro Gly Glu Glu Gln Thr
                340                 345                 350

Phe Glu Ile Glu Lys Tyr Ile Val His Lys Glu Phe Asp Asp Asp Thr
            355                 360                 365

Tyr Asp Asn Asp Ile Ala Leu Leu Gln Leu Arg Ser Asp Ser Ser Gln
            370                 375                 380

Cys Ala Gln Glu Ser Ser Val Gly Thr Ala Cys Leu Pro Asp Pro
385                 390                 395                 400

Asp Val Gln Leu Pro Asp Trp Thr Glu Cys Glu Leu Ser Gly Tyr Gly
                405                 410                 415

Lys His Glu Ala Ser Ser Pro Phe Phe Ser Asp Arg Leu Lys Glu Ala
            420                 425                 430

His Val Arg Leu Tyr Pro Ser Ser Arg Cys Thr Ser Gln His Leu Phe
            435                 440                 445

Asn Lys Thr Ile Thr Ser Asn Met Leu Cys Ala Gly Asp Thr Arg Thr
450                 455                 460

Gly Gly Asn Gln Asp Val His Asp Ala Cys Gln Gly Asp Ser Gly Gly
465                 470                 475                 480

Pro Leu Val Cys Met Ile Asp Lys Arg Met Thr Leu Leu Gly Ile Ile
                485                 490                 495

Ser Trp Gly Leu Gly Cys Gly Gln Lys Asp Val Pro Gly Ile Tyr Thr
            500                 505                 510

Lys Val Thr Asn Tyr Leu Asn Trp Ile Gln Asp Asn Met Lys Gln
            515                 520                 525

<210> SEQ ID NO 5
<211> LENGTH: 562
<212> TYPE: PRT
<213> ORGANISM: Homo sapiens

<400> SEQUENCE: 5

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ser Tyr Gln Val Ile Cys Arg Asp Glu Lys Thr Gln Met
            35                  40                  45

Ile Tyr Gln Gln His Gln Ser Trp Leu Arg Pro Val Leu Arg Ser Asn
            50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95
```

```
Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
            115                 120                 125

Glu Asp Gln Gly Ile Ser Tyr Arg Gly Thr Trp Ser Thr Ala Glu Ser
            130                 135             140

Gly Ala Glu Cys Thr Asn Trp Asn Ser Ser Ala Leu Ala Gln Lys Pro
145             150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
            195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225             230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Arg
            275                 280                 285

Glu Tyr Cys Asp Val Pro Ser Cys Ser Thr Cys Gly Leu Arg Gln Tyr
            290                 295                 300

Ser Gln Pro Gln Phe Arg Ile Lys Gly Gly Leu Phe Ala Asp Ile Ala
305             310                 315                 320

Ser His Pro Trp Gln Ala Ala Ile Phe Ala Lys His Arg Arg Ser Pro
            325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
            355                 360                 365

Thr Val Ile Leu Gly Arg Thr Tyr Arg Val Val Pro Gly Glu Glu Glu
            370                 375                 380

Gln Lys Phe Glu Val Glu Lys Tyr Ile Val His Lys Glu Phe Asp Asp
385             390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
            420                 425                 430

Pro Ala Asp Leu Gln Leu Pro Asp Trp Thr Glu Cys Glu Leu Ser Gly
            435                 440                 445

Tyr Gly Lys His Glu Ala Leu Ser Pro Phe Tyr Ser Glu Arg Leu Lys
            450                 455                 460

Glu Ala His Val Arg Leu Tyr Pro Ser Ser Arg Cys Thr Ser Gln His
465             470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
            500                 505                 510
```

```
Ser Gly Gly Pro Leu Val Cys Leu Asn Asp Gly Arg Met Thr Leu Val
            515                 520                 525

Gly Ile Ile Ser Trp Gly Leu Gly Cys Gly Gln Lys Asp Val Pro Gly
        530                 535                 540

Val Tyr Thr Lys Val Thr Asn Tyr Leu Asp Trp Ile Arg Asp Asn Met
545                 550                 555                 560

Arg Pro

<210> SEQ ID NO 6
<211> LENGTH: 527
<212> TYPE: PRT
<213> ORGANISM: Homo sapiens

<400> SEQUENCE: 6

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Arg Glu Tyr Cys
                245                 250                 255

Asp Val Pro Ser Cys Ser Thr Cys Gly Leu Arg Gln Tyr Ser Gln Pro
            260                 265                 270

Gln Phe Arg Ile Lys Gly Gly Leu Phe Ala Asp Ile Ala Ser His Pro
        275                 280                 285

Trp Gln Ala Ala Ile Phe Ala Lys His Arg Arg Ser Pro Gly Glu Arg
    290                 295                 300

Phe Leu Cys Gly Gly Ile Leu Ile Ser Ser Cys Trp Ile Leu Ser Ala
305                 310                 315                 320
```

```
Ala His Cys Phe Gln Glu Arg Phe Pro Pro His His Leu Thr Val Ile
            325                 330                 335

Leu Gly Arg Thr Tyr Arg Val Val Pro Gly Glu Glu Gln Lys Phe
            340                 345                 350

Glu Val Glu Lys Tyr Ile Val His Lys Glu Phe Asp Asp Thr Tyr
            355                 360                 365

Asp Asn Asp Ile Ala Leu Leu Gln Leu Lys Ser Asp Ser Ser Arg Cys
370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
            405                 410                 415

His Glu Ala Leu Ser Pro Phe Tyr Ser Glu Arg Leu Lys Glu Ala His
            420                 425                 430

Val Arg Leu Tyr Pro Ser Ser Arg Cys Thr Ser Gln His Leu Leu Asn
            435                 440                 445

Arg Thr Val Thr Asp Asn Met Leu Cys Ala Gly Asp Thr Arg Ser Gly
            450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
            485                 490                 495

Ser Trp Gly Leu Gly Cys Gly Gln Lys Asp Val Pro Gly Val Tyr Thr
            500                 505                 510

Lys Val Thr Asn Tyr Leu Asp Trp Ile Arg Asp Asn Met Arg Pro
            515                 520                 525

<210> SEQ ID NO 7
<211> LENGTH: 559
<212> TYPE: PRT
<213> ORGANISM: Rattus norvegicus

<400> SEQUENCE: 7

Met Lys Gly Glu Leu Leu Cys Val Leu Leu Leu Cys Gly Val Ala Phe
1               5                   10                  15

Thr Leu Pro Asp Gln Gly Ile His Arg Arg Phe Arg Arg Gly Ala Arg
            20                  25                  30

Ser Tyr Arg Ala Thr Cys Arg Asp Glu Gln Thr Gln Thr Thr Tyr Gln
            35                  40                  45

Gln His Gln Ser Trp Leu Arg Pro Met Leu Arg Gly Asn Arg Val Glu
        50                  55                  60

Tyr Cys Arg Cys Asn Ser Gly Leu Ala Gln Cys His Ser Val Pro Val
65                  70                  75                  80

Arg Ser Cys Ser Glu Pro Arg Cys Phe Asn Gly Gly Thr Cys Gln Gln
            85                  90                  95

Ala Leu Tyr Phe Ser Asp Phe Val Cys Gln Cys Pro Asp Gly Phe Val
            100                 105                 110

Gly Lys Arg Cys Asp Ile Asp Thr Arg Ala Thr Cys Phe Glu Gly Gln
            115                 120                 125

Gly Ile Thr Tyr Arg Gly Thr Trp Ser Thr Ala Glu Asn Gly Ala Glu
            130                 135                 140

Cys Ile Asn Trp Asn Ser Ser Ala Leu Ser Gln Lys Pro Tyr Ser Ala
145                 150                 155                 160

Arg Arg Pro Asn Ala Ile Lys Leu Gly Leu Gly Asn His Asn Tyr Cys
            165                 170                 175
```

Arg Asn Pro Asp Arg Asp Val Arg Pro Trp Cys Tyr Val Phe Lys Ala
            180                 185                 190

Gly Lys Tyr Thr Thr Glu Phe Cys Ser Thr Pro Ala Cys Pro Lys Gly
        195                 200                 205

Pro Thr Glu Asp Cys Tyr Val Gly Lys Gly Val Thr Tyr Arg Gly Thr
210                 215                 220

His Ser Phe Thr Thr Ser Lys Ala Ser Cys Leu Pro Trp Asn Ser Met
225                 230                 235                 240

Ile Leu Ile Gly Lys Thr Tyr Thr Ala Trp Arg Ala Asn Ser Gln Ala
                245                 250                 255

Leu Gly Leu Gly Arg His Asn Tyr Cys Arg Asn Pro Asp Gly Asp Ala
            260                 265                 270

Lys Pro Trp Cys His Val Met Lys Asp Arg Lys Leu Thr Trp Glu Tyr
        275                 280                 285

Cys Asp Met Ser Pro Cys Ser Thr Cys Gly Leu Arg Gln Tyr Lys Gln
290                 295                 300

Pro Leu Phe Ser Ile Lys Gly Gly Leu Phe Thr Asp Ile Thr Ser His
305                 310                 315                 320

Pro Trp Gln Ala Ala Ile Phe Val Lys Asn Lys Arg Ser Pro Gly Glu
                325                 330                 335

Arg Phe Leu Cys Gly Gly Val Leu Ile Ser Ser Cys Trp Val Leu Ser
            340                 345                 350

Ala Ala His Cys Phe Val Glu Arg Phe Pro Pro His Leu Lys Val
        355                 360                 365

Val Leu Gly Arg Thr Tyr Arg Val Val Pro Gly Glu Glu Glu Gln Thr
370                 375                 380

Phe Glu Ile Glu Lys Tyr Ile Val His Lys Glu Phe Asp Asp Asp Thr
385                 390                 395                 400

Tyr Asp Asn Asp Ile Ala Leu Leu Gln Leu Arg Ser Asp Ser Ser Gln
                405                 410                 415

Cys Ala Gln Glu Ser Ser Val Gly Thr Ala Cys Leu Pro Asp Pro
            420                 425                 430

Asp Val Gln Leu Pro Asp Trp Thr Glu Cys Glu Leu Ser Gly Tyr Gly
        435                 440                 445

Lys His Glu Ala Ser Ser Pro Phe Phe Ser Asp Arg Leu Lys Glu Ala
450                 455                 460

His Val Arg Leu Tyr Pro Ser Ser Arg Cys Thr Ser Gln His Leu Phe
465                 470                 475                 480

Asn Lys Thr Ile Thr Ser Asn Met Leu Cys Ala Gly Asp Thr Arg Thr
                485                 490                 495

Gly Gly Asn Gln Asp Val His Asp Ala Cys Gln Gly Asp Ser Gly Gly
            500                 505                 510

Pro Leu Val Cys Met Ile Asp Lys Arg Met Thr Leu Leu Gly Ile Ile
        515                 520                 525

Ser Trp Gly Leu Gly Cys Gly Gln Lys Asp Val Pro Gly Ile Tyr Thr
530                 535                 540

Lys Val Thr Asn Tyr Leu Asn Trp Ile Gln Asp Asn Met Lys Gln
545                 550                 555

<210> SEQ ID NO 8
<211> LENGTH: 527
<212> TYPE: PRT
<213> ORGANISM: Rattus norvegicus

```
<400> SEQUENCE: 8

Ser Tyr Arg Ala Thr Cys Arg Asp Glu Gln Thr Gln Thr Thr Tyr Gln
1               5                   10                  15

Gln His Gln Ser Trp Leu Arg Pro Met Leu Arg Gly Asn Arg Val Glu
            20                  25                  30

Tyr Cys Arg Cys Asn Ser Gly Leu Ala Gln Cys His Ser Val Pro Val
        35                  40                  45

Arg Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Asp Gly Phe Val
65                  70                  75                  80

Gly Lys Arg Cys Asp Ile Asp Thr Arg Ala Thr Cys Phe Glu Gly Gln
                85                  90                  95

Gly Ile Thr Tyr Arg Gly Thr Trp Ser Thr Ala Glu Asn Gly Ala Glu
            100                 105                 110

Cys Ile Asn Trp Asn Ser Ser Ala Leu Ser Gln Lys Pro Tyr Ser Ala
        115                 120                 125

Arg Arg Pro Asn Ala Ile Lys Leu Gly Leu Gly Asn His Asn Tyr Cys
    130                 135                 140

Arg Asn Pro Asp Arg Asp Val Arg Pro Trp Cys Tyr Val Phe Lys Ala
145                 150                 155                 160

Gly Lys Tyr Thr Thr Glu Phe Cys Ser Thr Pro Ala Cys Pro Lys Gly
                165                 170                 175

Pro Thr Glu Asp Cys Tyr Val Gly Lys Gly Val Thr Tyr Arg Gly Thr
            180                 185                 190

His Ser Phe Thr Thr Ser Lys Ala Ser Cys Leu Pro Trp Asn Ser Met
        195                 200                 205

Ile Leu Ile Gly Lys Thr Tyr Thr Ala Trp Arg Ala Asn Ser Gln Ala
    210                 215                 220

Leu Gly Leu Gly Arg His Asn Tyr Cys Arg Asn Pro Asp Gly Asp Ala
225                 230                 235                 240

Lys Pro Trp Cys His Val Met Lys Asp Arg Lys Leu Thr Trp Glu Tyr
                245                 250                 255

Cys Asp Met Ser Pro Cys Ser Thr Cys Gly Leu Arg Gln Tyr Lys Gln
            260                 265                 270

Pro Leu Phe Ser Ile Lys Gly Gly Leu Phe Thr Asp Ile Thr Ser His
        275                 280                 285

Pro Trp Gln Ala Ala Ile Phe Val Lys Asn Lys Arg Ser Pro Gly Glu
    290                 295                 300

Arg Phe Leu Cys Gly Gly Val Leu Ile Ser Ser Cys Trp Val Leu Ser
305                 310                 315                 320

Ala Ala His Cys Phe Val Glu Arg Phe Pro Pro His His Leu Lys Val
                325                 330                 335

Val Leu Gly Arg Thr Tyr Arg Val Val Pro Gly Glu Glu Gln Thr
            340                 345                 350

Phe Glu Ile Glu Lys Tyr Ile Val His Lys Glu Phe Asp Asp Asp Thr
        355                 360                 365

Tyr Asp Asn Asp Ile Ala Leu Leu Gln Leu Arg Ser Asp Ser Ser Gln
    370                 375                 380

Cys Ala Gln Glu Ser Ser Ser Val Gly Thr Ala Cys Leu Pro Asp Pro
385                 390                 395                 400

Asp Val Gln Leu Pro Asp Trp Thr Glu Cys Glu Leu Ser Gly Tyr Gly
                405                 410                 415
```

```
Lys His Glu Ala Ser Ser Pro Phe Phe Ser Asp Arg Leu Lys Glu Ala
                420                 425                 430

His Val Arg Leu Tyr Pro Ser Ser Arg Cys Thr Ser Gln His Leu Phe
            435                 440                 445

Asn Lys Thr Ile Thr Ser Asn Met Leu Cys Ala Gly Asp Thr Arg Thr
        450                 455                 460

Gly Gly Asn Gln Asp Val His Asp Ala Cys Gln Gly Asp Ser Gly Gly
465                 470                 475                 480

Pro Leu Val Cys Met Ile Asp Lys Arg Met Thr Leu Gly Ile Ile
                485                 490                 495

Ser Trp Gly Leu Gly Cys Gly Gln Lys Asp Val Pro Gly Ile Tyr Thr
                500                 505                 510

Lys Val Thr Asn Tyr Leu Asn Trp Ile Gln Asp Asn Met Lys Gln
            515                 520                 525
```

<210> SEQ ID NO 9
<211> LENGTH: 562
<212> TYPE: PRT
<213> ORGANISM: Homo sapiens

<400> SEQUENCE: 9

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ser Tyr Gln Val Ile Cys Arg Asp Glu Lys Thr Gln Met
            35                  40                  45

Ile Tyr Gln Gln His Gln Ser Trp Leu Arg Pro Val Leu Arg Ser Asn
50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
    130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
```

```
                    260                 265                 270
Asp Ala Lys Pro Trp Cys His Val Leu Lys Asn Arg Arg Leu Thr Trp
        275                 280                 285

Glu Tyr Cys Asp Val Pro Ser Cys Ser Thr Cys Gly Leu Arg Gln Tyr
290                 295                 300

Ser Gln Pro Gln Phe Ser Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
                340                 345                 350

Leu Ser Ala Ala His Cys Phe Gln Glu Arg Phe Pro Pro His His Leu
            355                 360                 365

Thr Val Ile Leu Gly Arg Thr Tyr Arg Val Val Pro Gly Glu Glu Glu
            370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
                420                 425                 430

Pro Ala Asp Leu Gln Leu Pro Asp Trp Thr Glu Cys Glu Leu Ser Gly
            435                 440                 445

Tyr Gly Lys His Glu Ala Leu Ser Pro Phe Tyr Ser Glu Arg Leu Lys
            450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
                500                 505                 510

Ser Gly Gly Pro Leu Val Cys Leu Asn Asp Gly Arg Met Thr Leu Val
            515                 520                 525

Gly Ile Ile Ser Trp Gly Leu Gly Cys Gly Gln Lys Asp Val Pro Gly
            530                 535                 540

Val Tyr Thr Lys Val Thr Asn Tyr Leu Asp Trp Ile Arg Asp Asn Met
545                 550                 555                 560

Arg Pro

<210> SEQ ID NO 10
<211> LENGTH: 527
<212> TYPE: PRT
<213> ORGANISM: Homo sapiens

<400> SEQUENCE: 10

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
```

```
                65                  70                  75                  80
Gly Lys Cys Cys Glu Ile Asp Thr Arg Ala Thr Cys Tyr Glu Asp Gln
                    85                  90                  95
Gly Ile Ser Tyr Arg Gly Thr Trp Ser Thr Ala Glu Ser Gly Ala Glu
                    100                 105                 110
Cys Thr Asn Trp Asn Ser Ser Leu Ala Gln Lys Pro Tyr Ser Gly
                115                 120                 125
Arg Arg Pro Asp Ala Ile Arg Leu Gly Leu Gly Asn His Asn Tyr Cys
                130                 135                 140
Arg Asn Pro Asp Arg Asp Ser Lys Pro Trp Cys Tyr Val Phe Lys Ala
145                 150                 155                 160
Gly Lys Tyr Ser Ser Glu Phe Cys Ser Thr Pro Ala Cys Ser Glu Gly
                    165                 170                 175
Asn Ser Asp Cys Tyr Phe Gly Asn Gly Ser Ala Tyr Arg Gly Thr His
                    180                 185                 190
Ser Leu Thr Glu Ser Gly Ala Ser Cys Leu Pro Trp Asn Ser Met Ile
                    195                 200                 205
Leu Ile Gly Lys Val Tyr Thr Ala Gln Asn Pro Ser Ala Gln Ala Leu
                210                 215                 220
Gly Leu Gly Lys His Asn Tyr Cys Arg Asn Pro Asp Gly Asp Ala Lys
225                 230                 235                 240
Pro Trp Cys His Val Leu Lys Asn Arg Arg Leu Thr Trp Glu Tyr Cys
                    245                 250                 255
Asp Val Pro Ser Cys Ser Thr Cys Gly Leu Arg Gln Tyr Ser Gln Pro
                    260                 265                 270
Gln Phe Ser Ile Lys Gly Gly Leu Phe Ala Asp Ile Ala Ser His Pro
                275                 280                 285
Trp Gln Ala Ala Ile Phe Ala Lys His Arg Arg Ser Pro Gly Glu Arg
                290                 295                 300
Phe Leu Cys Gly Gly Ile Leu Ile Ser Ser Cys Trp Ile Leu Ser Ala
305                 310                 315                 320
Ala His Cys Phe Gln Glu Arg Phe Pro Pro His His Leu Thr Val Ile
                    325                 330                 335
Leu Gly Arg Thr Tyr Arg Val Val Pro Gly Glu Glu Glu Gln Lys Phe
                    340                 345                 350
Glu Val Glu Lys Tyr Ile Val His Lys Glu Phe Asp Asp Thr Tyr
                    355                 360                 365
Asp Asn Asp Ile Ala Leu Leu Gln Leu Lys Ser Asp Ser Ser Arg Cys
                370                 375                 380
Ala Gln Glu Ser Ser Val Val Arg Thr Val Cys Leu Pro Pro Ala Asp
385                 390                 395                 400
Leu Gln Leu Pro Asp Trp Thr Glu Cys Glu Leu Ser Gly Tyr Gly Lys
                    405                 410                 415
His Glu Ala Leu Ser Pro Phe Tyr Ser Glu Arg Leu Lys Glu Ala His
                    420                 425                 430
Val Arg Leu Tyr Pro Ser Ser Arg Cys Thr Ser Gln His Leu Leu Asn
                435                 440                 445
Arg Thr Val Thr Asp Asn Met Leu Cys Ala Gly Asp Thr Arg Ser Gly
                450                 455                 460
Gly Pro Gln Ala Asn Leu His Asp Ala Cys Gln Gly Asp Ser Gly Gly
465                 470                 475                 480
Pro Leu Val Cys Leu Asn Asp Gly Arg Met Thr Leu Val Gly Ile Ile
                    485                 490                 495
```

```
Ser Trp Gly Leu Gly Cys Gly Gln Lys Asp Val Pro Gly Val Tyr Thr
            500                 505                 510
Lys Val Thr Asn Tyr Leu Asp Trp Ile Arg Asp Asn Met Arg Pro
        515                 520                 525
```

<210> SEQ ID NO 11
<211> LENGTH: 559
<212> TYPE: PRT
<213> ORGANISM: Rattus norvegicus

<400> SEQUENCE: 11

```
Met Lys Gly Glu Leu Leu Cys Val Leu Leu Cys Gly Val Ala Phe
1               5                   10                  15
Thr Leu Pro Asp Gln Gly Ile His Arg Arg Phe Arg Arg Gly Ala Arg
            20                  25                  30
Ser Tyr Arg Ala Thr Cys Arg Asp Glu Gln Thr Gln Thr Thr Tyr Gln
        35                  40                  45
Gln His Gln Ser Trp Leu Arg Pro Met Leu Arg Gly Asn Arg Val Glu
    50                  55                  60
Tyr Cys Arg Cys Asn Ser Gly Leu Ala Gln Cys His Ser Val Pro Val
65                  70                  75                  80
Arg Ser Cys Ser Glu Pro Arg Cys Phe Asn Gly Gly Thr Cys Gln Gln
                85                  90                  95
Ala Leu Tyr Phe Ser Asp Phe Val Cys Gln Cys Pro Asp Gly Phe Val
            100                 105                 110
Gly Lys Arg Cys Asp Ile Asp Thr Arg Ala Thr Cys Phe Glu Gly Gln
        115                 120                 125
Gly Ile Thr Tyr Arg Gly Thr Trp Ser Thr Ala Glu Asn Gly Ala Glu
    130                 135                 140
Cys Ile Asn Trp Asn Ser Ser Ala Leu Ser Gln Lys Pro Tyr Ser Ala
145                 150                 155                 160
Arg Arg Pro Asn Ala Ile Lys Leu Gly Leu Gly Asn His Asn Tyr Cys
                165                 170                 175
Arg Asn Pro Asp Arg Asp Val Arg Pro Trp Cys Tyr Val Phe Lys Ala
            180                 185                 190
Gly Lys Tyr Thr Thr Glu Phe Cys Ser Thr Pro Ala Cys Pro Lys Gly
        195                 200                 205
Pro Thr Glu Asp Cys Tyr Val Gly Lys Gly Val Thr Tyr Arg Gly Thr
    210                 215                 220
His Ser Phe Thr Thr Ser Lys Ala Ser Cys Leu Pro Trp Asn Ser Met
225                 230                 235                 240
Ile Leu Ile Gly Lys Thr Tyr Thr Ala Trp Arg Ala Asn Ser Gln Ala
                245                 250                 255
Leu Gly Leu Gly Arg His Asn Tyr Cys Arg Asn Pro Asp Gly Asp Ala
            260                 265                 270
Lys Pro Trp Cys His Val Met Lys Asp Arg Lys Leu Thr Arg Glu Tyr
        275                 280                 285
Cys Asp Met Ser Pro Cys Ser Thr Cys Gly Leu Arg Gln Tyr Lys Gln
    290                 295                 300
Pro Leu Phe Ser Ile Lys Gly Gly Leu Phe Thr Asp Ile Thr Ser His
305                 310                 315                 320
Pro Trp Gln Ala Ala Ile Phe Val Lys Asn Lys Arg Ser Pro Gly Glu
                325                 330                 335
Arg Phe Leu Cys Gly Gly Val Leu Ile Ser Ser Cys Trp Val Leu Ser
```

-continued

```
                    340                 345                 350
Ala Ala His Cys Phe Val Glu Arg Phe Pro His His Leu Lys Val
            355                 360                 365

Val Leu Gly Arg Thr Tyr Arg Val Pro Gly Glu Glu Gln Thr
    370                 375                 380

Phe Glu Ile Glu Lys Tyr Ile Val His Lys Glu Phe Asp Asp Asp Thr
385                 390                 395                 400

Tyr Asp Asn Asp Ile Ala Leu Leu Gln Leu Arg Ser Asp Ser Ser Gln
                405                 410                 415

Cys Ala Gln Glu Ser Ser Ser Val Gly Thr Ala Cys Leu Pro Asp Pro
            420                 425                 430

Asp Val Gln Leu Pro Asp Trp Thr Glu Cys Glu Leu Ser Gly Tyr Gly
            435                 440                 445

Lys His Glu Ala Ser Ser Pro Phe Phe Ser Asp Arg Leu Lys Glu Ala
            450                 455                 460

His Val Arg Leu Tyr Pro Ser Ser Arg Cys Thr Ser Gln His Leu Phe
465                 470                 475                 480

Asn Lys Thr Ile Thr Ser Asn Met Leu Cys Ala Gly Asp Thr Arg Thr
                485                 490                 495

Gly Gly Asn Gln Asp Val His Asp Ala Cys Gln Gly Asp Ser Gly Gly
            500                 505                 510

Pro Leu Val Cys Met Ile Asp Lys Arg Met Thr Leu Leu Gly Ile Ile
            515                 520                 525

Ser Trp Gly Leu Gly Cys Gly Gln Lys Asp Val Pro Gly Ile Tyr Thr
            530                 535                 540

Lys Val Thr Asn Tyr Leu Asn Trp Ile Gln Asp Asn Met Lys Gln
545                 550                 555

<210> SEQ ID NO 12
<211> LENGTH: 527
<212> TYPE: PRT
<213> ORGANISM: Rattus norvegicus

<400> SEQUENCE: 12

Ser Tyr Arg Ala Thr Cys Arg Asp Glu Gln Thr Gln Thr Thr Tyr Gln
1               5                   10                  15

Gln His Gln Ser Trp Leu Arg Pro Met Leu Arg Gly Asn Arg Val Glu
                20                  25                  30

Tyr Cys Arg Cys Asn Ser Gly Leu Ala Gln Cys His Ser Val Pro Val
            35                  40                  45

Arg Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Asp Gly Phe Val
65                  70                  75                  80

Gly Lys Arg Cys Asp Ile Asp Thr Arg Ala Thr Cys Phe Glu Gly Gln
                85                  90                  95

Gly Ile Thr Tyr Arg Gly Thr Trp Ser Thr Ala Glu Asn Gly Ala Glu
            100                 105                 110

Cys Ile Asn Trp Asn Ser Ser Ala Leu Ser Gln Lys Pro Tyr Ser Ala
        115                 120                 125

Arg Arg Pro Asn Ala Ile Lys Leu Gly Leu Gly Asn His Asn Tyr Cys
    130                 135                 140

Arg Asn Pro Asp Arg Asp Val Arg Pro Trp Cys Tyr Val Phe Lys Ala
145                 150                 155                 160
```

Gly Lys Tyr Thr Thr Glu Phe Cys Ser Thr Pro Ala Cys Pro Lys Gly
            165                 170                 175

Pro Thr Glu Asp Cys Tyr Val Gly Lys Gly Val Thr Tyr Arg Gly Thr
        180                 185                 190

His Ser Phe Thr Thr Ser Lys Ala Ser Cys Leu Pro Trp Asn Ser Met
    195                 200                 205

Ile Leu Ile Gly Lys Thr Tyr Thr Ala Trp Arg Ala Asn Ser Gln Ala
210                 215                 220

Leu Gly Leu Gly Arg His Asn Tyr Cys Arg Asn Pro Asp Gly Asp Ala
225                 230                 235                 240

Lys Pro Trp Cys His Val Met Lys Asp Arg Lys Leu Thr Arg Glu Tyr
                245                 250                 255

Cys Asp Met Ser Pro Cys Ser Thr Cys Gly Leu Arg Gln Tyr Lys Gln
            260                 265                 270

Pro Leu Phe Ser Ile Lys Gly Gly Leu Phe Thr Asp Ile Thr Ser His
        275                 280                 285

Pro Trp Gln Ala Ala Ile Phe Val Lys Asn Lys Arg Ser Pro Gly Glu
    290                 295                 300

Arg Phe Leu Cys Gly Gly Val Leu Ile Ser Ser Cys Trp Val Leu Ser
305                 310                 315                 320

Ala Ala His Cys Phe Val Glu Arg Phe Pro Pro His His Leu Lys Val
                325                 330                 335

Val Leu Gly Arg Thr Tyr Arg Val Val Pro Gly Glu Glu Glu Gln Thr
            340                 345                 350

Phe Glu Ile Glu Lys Tyr Ile Val His Lys Glu Phe Asp Asp Asp Thr
        355                 360                 365

Tyr Asp Asn Asp Ile Ala Leu Leu Gln Leu Arg Ser Asp Ser Ser Gln
370                 375                 380

Cys Ala Gln Glu Ser Ser Val Gly Thr Ala Cys Leu Pro Asp Pro
385                 390                 395                 400

Asp Val Gln Leu Pro Asp Trp Thr Glu Cys Glu Leu Ser Gly Tyr Gly
                405                 410                 415

Lys His Glu Ala Ser Ser Pro Phe Phe Ser Asp Arg Leu Lys Glu Ala
            420                 425                 430

His Val Arg Leu Tyr Pro Ser Ser Arg Cys Thr Ser Gln His Leu Phe
        435                 440                 445

Asn Lys Thr Ile Thr Ser Asn Met Leu Cys Ala Gly Asp Thr Arg Thr
    450                 455                 460

Gly Gly Asn Gln Asp Val His Asp Ala Cys Gln Gly Asp Ser Gly Gly
465                 470                 475                 480

Pro Leu Val Cys Met Ile Asp Lys Arg Met Thr Leu Leu Gly Ile Ile
                485                 490                 495

Ser Trp Gly Leu Gly Cys Gly Gln Lys Asp Val Pro Gly Ile Tyr Thr
            500                 505                 510

Lys Val Thr Asn Tyr Leu Asn Trp Ile Gln Asp Asn Met Lys Gln
        515                 520                 525

<210> SEQ ID NO 13
<211> LENGTH: 562
<212> TYPE: PRT
<213> ORGANISM: Homo sapiens

<400> SEQUENCE: 13

Met Asp Ala Met Lys Arg Gly Leu Cys Cys Val Leu Leu Leu Cys Gly
1               5                   10                  15

```
Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
                    100                 105                 110

Gly Phe Ala Gly Lys Cys Cys Glu Ile Asp Thr Arg Ala Thr Cys Tyr
                115                 120                 125

Glu Asp Gln Gly Ile Ser Tyr Arg Gly Thr Trp Ser Thr Ala Glu Ser
            130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
                180                 185                 190

Phe Lys Ala Gly Lys Tyr Ser Ser Glu Phe Cys Ser Thr Pro Ala Cys
            195                 200                 205

Ser Glu Gly Asn Ser Asp Cys Tyr Phe Gly Asn Gly Ser Ala Tyr Arg
            210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
                260                 265                 270

Asp Ala Lys Pro Trp Cys His Val Leu Lys Asn Arg Arg Leu Thr Arg
                275                 280                 285

Glu Tyr Cys Asp Val Pro Ser Cys Ser Thr Cys Gly Leu Arg Gln Tyr
            290                 295                 300

Ser Gln Pro Gln Phe Ser Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
                340                 345                 350

Leu Ser Ala Ala His Cys Phe Gln Glu Arg Phe Pro Pro His His Leu
            355                 360                 365

Thr Val Ile Leu Gly Arg Thr Tyr Arg Val Val Pro Gly Glu Glu Glu
            370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
                420                 425                 430
```

```
Pro Ala Asp Leu Gln Leu Pro Asp Trp Thr Glu Cys Glu Leu Ser Gly
            435                 440                 445
Tyr Gly Lys His Glu Ala Leu Ser Pro Phe Tyr Ser Glu Arg Leu Lys
450                 455                 460
Glu Ala His Val Arg Leu Tyr Pro Ser Ser Arg Cys Thr Ser Gln His
465                 470                 475                 480
Leu Leu Asn Arg Thr Val Thr Asp Asn Met Leu Cys Ala Gly Asp Thr
                485                 490                 495
Arg Ser Gly Gly Pro Gln Ala Asn Leu His Asp Ala Cys Gln Gly Asp
            500                 505                 510
Ser Gly Gly Pro Leu Val Cys Leu Asn Asp Gly Arg Met Thr Leu Val
            515                 520                 525
Gly Ile Ile Ser Trp Gly Leu Gly Cys Gly Gln Lys Asp Val Pro Gly
            530                 535                 540
Val Tyr Thr Lys Val Thr Asn Tyr Leu Asp Trp Ile Arg Asp Asn Met
545                 550                 555                 560
Arg Pro

<210> SEQ ID NO 14
<211> LENGTH: 527
<212> TYPE: PRT
<213> ORGANISM: Homo sapiens

<400> SEQUENCE: 14

Ser Tyr Gln Val Ile Cys Arg Asp Glu Lys Thr Gln Met Ile Tyr Gln
1               5                   10                  15
Gln His Gln Ser Trp Leu Arg Pro Val Leu Arg Ser Asn Arg Val Glu
                20                  25                  30
Tyr Cys Trp Cys Asn Ser Gly Arg Ala Gln Cys His Ser Val Pro Val
            35                  40                  45
Lys Ser Cys Ser Glu Pro Arg Cys Phe Asn Gly Gly Thr Cys Gln Gln
50                  55                  60
Ala Leu Tyr Phe Ser Asp Phe Val Cys Gln Cys Pro Glu Gly Phe Ala
65                  70                  75                  80
Gly Lys Cys Cys Glu Ile Asp Thr Arg Ala Thr Cys Tyr Glu Asp Gln
                85                  90                  95
Gly Ile Ser Tyr Arg Gly Thr Trp Ser Thr Ala Glu Ser Gly Ala Glu
            100                 105                 110
Cys Thr Asn Trp Asn Ser Ser Ala Leu Ala Gln Lys Pro Tyr Ser Gly
        115                 120                 125
Arg Arg Pro Asp Ala Ile Arg Leu Gly Leu Gly Asn His Asn Tyr Cys
130                 135                 140
Arg Asn Pro Asp Arg Asp Ser Lys Pro Trp Cys Tyr Val Phe Lys Ala
145                 150                 155                 160
Gly Lys Tyr Ser Ser Glu Phe Cys Ser Thr Pro Ala Cys Ser Glu Gly
                165                 170                 175
Asn Ser Asp Cys Tyr Phe Gly Asn Gly Ser Ala Tyr Arg Gly Thr His
            180                 185                 190
Ser Leu Thr Glu Ser Gly Ala Ser Cys Leu Pro Trp Asn Ser Met Ile
        195                 200                 205
Leu Ile Gly Lys Val Tyr Thr Ala Gln Asn Pro Ser Ala Gln Ala Leu
210                 215                 220
Gly Leu Gly Lys His Asn Tyr Cys Arg Asn Pro Asp Gly Asp Ala Lys
225                 230                 235                 240
```

```
Pro Trp Cys His Val Leu Lys Asn Arg Arg Leu Thr Arg Glu Tyr Cys
            245                 250                 255

Asp Val Pro Ser Cys Ser Thr Cys Gly Leu Arg Gln Tyr Ser Gln Pro
260                 265                 270

Gln Phe Ser Ile Lys Gly Gly Leu Phe Ala Asp Ile Ala Ser His Pro
        275                 280                 285

Trp Gln Ala Ala Ile Phe Ala Lys His Arg Arg Ser Pro Gly Glu Arg
290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
            325                 330                 335

Leu Gly Arg Thr Tyr Arg Val Val Pro Gly Glu Glu Glu Gln Lys Phe
        340                 345                 350

Glu Val Glu Lys Tyr Ile Val His Lys Glu Phe Asp Asp Asp Thr Tyr
    355                 360                 365

Asp Asn Asp Ile Ala Leu Leu Gln Leu Lys Ser Asp Ser Ser Arg Cys
370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
            405                 410                 415

His Glu Ala Leu Ser Pro Phe Tyr Ser Glu Arg Leu Lys Glu Ala His
                420                 425                 430

Val Arg Leu Tyr Pro Ser Ser Arg Cys Thr Ser Gln His Leu Leu Asn
        435                 440                 445

Arg Thr Val Thr Asp Asn Met Leu Cys Ala Gly Asp Thr Arg Ser Gly
    450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
            485                 490                 495

Ser Trp Gly Leu Gly Cys Gly Gln Lys Asp Val Pro Gly Val Tyr Thr
                500                 505                 510

Lys Val Thr Asn Tyr Leu Asp Trp Ile Arg Asp Asn Met Arg Pro
        515                 520                 525

<210> SEQ ID NO 15
<211> LENGTH: 1734
<212> TYPE: PRT
<213> ORGANISM: Rattus norvegicus

<400> SEQUENCE: 15

Ala Thr Gly Ala Ala Gly Gly Ala Gly Ala Gly Cys Thr Gly Thr
1               5                   10                  15

Thr Gly Thr Gly Cys Gly Thr Cys Cys Thr Gly Cys Thr Gly Cys Thr
            20                  25                  30

Thr Thr Gly Thr Gly Gly Ala Gly Thr Gly Gly Cys Gly Thr Thr Cys
        35                  40                  45

Ala Cys Gly Thr Thr Gly Cys Thr Gly Ala Cys Cys Ala Gly Gly
    50                  55                  60

Gly Ala Ala Thr Ala Cys Ala Cys Ala Gly Gly Ala Gly Gly Thr Thr
65                  70                  75                  80

Cys Ala Gly Ala Ala Gly Ala Gly Gly Ala Gly Cys Thr Cys Gly Gly
            85                  90                  95
```

```
Cys Ala Thr Cys Ala Cys Cys Ala Thr Cys Ala Cys Cys Ala Thr Cys
100 105 110

Ala Cys Gly Gly Ala Thr Cys Cys Thr Cys Cys Thr Ala Cys Ala Gly
115 120 125

Ala Gly Cys Gly Ala Cys Cys Thr Gly Cys Ala Gly Ala Gly Ala Thr
130 135 140

Gly Ala Ala Cys Ala Gly Ala Cys Thr Cys Ala Gly Ala Cys Ala Ala
145 150 155 160

Cys Thr Thr Ala Cys Cys Ala Ala Cys Ala Gly Cys Ala Thr Cys Ala
165 170 175

Gly Thr Cys Ala Thr Gly Gly Cys Thr Ala Cys Gly Thr Cys Cys Cys
180 185 190

Ala Thr Gly Cys Thr Cys Ala Gly Ala Gly Gly Cys Ala Ala Thr Cys
195 200 205

Gly Gly Gly Thr Gly Gly Ala Ala Thr Ala Cys Thr Gly Cys Cys Gly
210 215 220

Gly Thr Gly Cys Ala Ala Cys Ala Gly Cys Gly Gly Cys Cys Thr Gly
225 230 235 240

Gly Cys Ala Cys Ala Gly Thr Gly Cys Cys Ala Cys Thr Cys Gly Gly
245 250 255

Thr Gly Cys Cys Cys Gly Thr Cys Cys Gly Ala Ala Gly Thr Thr Gly
260 265 270

Cys Ala Gly Thr Gly Ala Ala Cys Cys Gly Ala Gly Ala Thr Gly Cys
275 280 285

Thr Thr Cys Ala Ala Thr Gly Gly Gly Gly Gly Thr Ala Cys Gly Thr
290 295 300

Gly Thr Cys Ala Gly Cys Ala Gly Gly Cys Cys Cys Thr Gly Thr Ala
305 310 315 320

Thr Thr Thr Cys Thr Cys Thr Gly Ala Cys Thr Thr Cys Gly Thr Cys
325 330 335

Thr Gly Cys Cys Ala Gly Thr Gly Cys Cys Cys Thr Gly Ala Cys Gly
340 345 350

Gly Ala Thr Thr Thr Gly Thr Thr Gly Gly Gly Ala Ala Ala Cys Gly
355 360 365

Cys Thr Gly Thr Gly Ala Thr Ala Thr Ala Gly Ala Thr Ala Cys Cys
370 375 380

Ala Gly Ala Gly Cys Ala Ala Cys Cys Thr Gly Cys Thr Thr Cys Gly
385 390 395 400

Ala Gly Gly Gly Cys Cys Ala Gly Gly Gly Cys Ala Thr Cys Ala Cys
405 410 415

Cys Thr Ala Cys Ala Gly Ala Gly Gly Cys Ala Cys Ala Thr Gly Gly
420 425 430

Ala Gly Cys Ala Cys Ala Gly Cys Ala Gly Ala Ala Ala Ala Thr Gly
435 440 445

Gly Gly Gly Cys Thr Gly Ala Ala Thr Gly Cys Ala Thr Cys Ala Ala
450 455 460

Cys Thr Gly Gly Ala Ala Thr Ala Gly Cys Ala Gly Thr Gly Cys Cys
465 470 475 480

Cys Thr Gly Thr Cys Cys Cys Ala Gly Ala Ala Gly Cys Cys Cys Thr
485 490 495

Ala Cys Ala Gly Thr Gly Cys Ala Ala Gly Gly Ala Gly Gly Cys Cys
500 505 510

-continued

Ala Ala Ala Thr Gly Cys Cys Ala Thr Cys Ala Gly Cys Thr Gly
            515                 520                 525

Gly Gly Cys Cys Thr Thr Gly Gly Ala Ala Cys Cys Ala Cys Ala
            530                 535                 540

Ala Thr Thr Ala Cys Thr Gly Cys Ala Gly Ala Ala Cys Cys Cys
545                 550                 555                 560

Ala Gly Ala Cys Cys Gly Ala Gly Ala Cys Gly Thr Gly Ala Gly
                565                 570                 575

Cys Cys Cys Thr Gly Gly Thr Gly Cys Thr Ala Thr Gly Thr Cys Thr
                580                 585                 590

Thr Thr Ala Ala Gly Gly Cys Ala Gly Gly Gly Ala Ala Gly Thr Ala
            595                 600                 605

Thr Ala Cys Cys Ala Cys Gly Gly Ala Gly Thr Thr Cys Thr Gly Cys
            610                 615                 620

Ala Gly Cys Ala Cys Gly Cys Cys Gly Gly Cys Thr Thr Gly Cys Cys
625                 630                 635                 640

Cys Thr Ala Ala Gly Gly Gly Ala Cys Cys Ala Ala Cys Thr Gly Ala
                645                 650                 655

Gly Gly Ala Cys Thr Gly Cys Thr Ala Thr Gly Thr Thr Gly Gly Ala
                660                 665                 670

Ala Ala Ala Gly Gly Thr Gly Thr Gly Ala Cys Thr Ala Cys Cys
            675                 680                 685

Gly Thr Gly Gly Cys Ala Cys Cys Cys Ala Cys Ala Gly Cys Thr Thr
            690                 695                 700

Thr Ala Cys Cys Ala Cys Ala Thr Cys Ala Ala Gly Gly Cys Cys
705                 710                 715                 720

Thr Cys Cys Thr Gly Cys Cys Thr Cys Cys Ala Thr Gly Gly Ala
                725                 730                 735

Ala Thr Thr Cys Cys Ala Thr Gly Ala Thr Cys Cys Thr Gly Ala Thr
                740                 745                 750

Ala Gly Gly Cys Ala Ala Gly Ala Cys Thr Thr Ala Cys Ala Cys Ala
            755                 760                 765

Gly Cys Gly Thr Gly Gly Ala Gly Gly Gly Cys Cys Ala Ala Cys Thr
            770                 775                 780

Cys Cys Cys Ala Gly Gly Cys Ala Cys Thr Gly Gly Cys Cys Thr
785                 790                 795                 800

Gly Gly Gly Cys Ala Gly Ala Cys Ala Cys Ala Thr Thr Ala Thr
                805                 810                 815

Thr Gly Cys Cys Gly Gly Ala Ala Cys Cys Cys Ala Gly Ala Thr Gly
            820                 825                 830

Gly Gly Gly Ala Thr Gly Cys Cys Ala Ala Cys Cys Thr Thr Gly
                835                 840                 845

Gly Thr Gly Cys Cys Ala Cys Gly Thr Gly Ala Thr Gly Ala Ala Gly
            850                 855                 860

Gly Ala Cys Cys Gly Ala Ala Ala Gly Cys Thr Gly Ala Cys Ala Thr
865                 870                 875                 880

Gly Gly Gly Ala Ala Thr Ala Thr Thr Gly Cys Gly Ala Cys Ala Thr
                885                 890                 895

Gly Thr Cys Cys Cys Ala Thr Gly Cys Thr Cys Ala Cys Cys
            900                 905                 910

Thr Gly Cys Gly Gly Cys Cys Thr Gly Ala Gly Gly Cys Ala Ala Thr
            915                 920                 925

Ala Cys Ala Ala Ala Cys Ala Gly Cys Cys Thr Cys Thr Gly Thr Thr

```
                930             935             940
Thr Cys Gly Ala Ala Thr Thr Ala Ala Ala Gly Gly Ala Gly Gly Ala
945                 950             955                 960
Cys Thr Cys Thr Thr Cys Ala Cys Ala Gly Ala Cys Ala Thr Cys Ala
                    965             970                 975
Cys Cys Thr Cys Ala Cys Ala Cys Cys Cys Thr Thr Gly Gly Cys Ala
                980             985                 990
Gly Gly Cys Cys Gly Cys Cys Ala Thr Cys Thr Thr Thr Gly Thr Cys
            995                 1000            1005
Ala Ala Gly Ala Ala Cys Ala Ala Gly Ala Gly Gly Thr Cys Thr
    1010            1015            1020
Cys Cys Ala Gly Gly Ala Gly Ala Gly Ala Gly Ala Thr Thr Cys
    1025            1030            1035
Cys Thr Gly Thr Gly Thr Gly Gly Ala Gly Gly Gly Gly Thr Gly
    1040            1045            1050
Cys Thr Gly Ala Thr Cys Ala Gly Thr Thr Cys Cys Thr Gly Cys
    1055            1060            1065
Thr Gly Gly Thr Gly Cys Thr Ala Thr Cys Thr Gly Cys Cys
    1070            1075            1080
Gly Cys Cys Cys Ala Cys Thr Gly Cys Thr Thr Thr Gly Thr Ala
    1085            1090            1095
Gly Ala Gly Ala Gly Gly Thr Thr Thr Cys Cys Ala Cys Cys Cys
    1100            1105            1110
Cys Ala Thr Cys Ala Thr Cys Thr Thr Ala Ala Ala Gly Thr Gly
    1115            1120            1125
Gly Thr Cys Thr Thr Gly Gly Gly Cys Ala Gly Ala Ala Cys Ala
    1130            1135            1140
Thr Ala Cys Ala Gly Ala Gly Thr Gly Gly Thr Cys Cys Cys Thr
    1145            1150            1155
Gly Gly Ala Gly Ala Gly Gly Ala Gly Gly Ala Gly Cys Ala Gly
    1160            1165            1170
Ala Cys Ala Thr Thr Cys Gly Ala Gly Ala Thr Cys Gly Ala Ala
    1175            1180            1185
Ala Ala Gly Thr Ala Cys Ala Thr Ala Gly Thr Cys Cys Ala Thr
    1190            1195            1200
Ala Ala Gly Gly Ala Ala Thr Thr Thr Gly Ala Thr Gly Ala Cys
    1205            1210            1215
Gly Ala Cys Ala Cys Thr Thr Ala Thr Gly Ala Cys Ala Ala Thr
    1220            1225            1230
Gly Ala Cys Ala Thr Cys Gly Cys Ala Thr Thr Ala Cys Thr Gly
    1235            1240            1245
Cys Ala Gly Cys Thr Gly Ala Gly Gly Thr Cys Ala Gly Ala Thr
    1250            1255            1260
Thr Cys Cys Ala Gly Thr Cys Ala Gly Thr Gly Thr Gly Cys Cys
    1265            1270            1275
Cys Ala Gly Gly Ala Gly Ala Gly Cys Ala Gly Thr Thr Cys Thr
    1280            1285            1290
Gly Thr Cys Gly Gly Cys Ala Cys Thr Gly Cys Cys Thr Gly Cys
    1295            1300            1305
Cys Thr Cys Cys Cys Thr Gly Ala Cys Cys Cys Gly Ala Cys
    1310            1315            1320
Gly Thr Ala Cys Ala Gly Cys Thr Thr Cys Thr Gly Ala Cys
    1325            1330            1335
```

Thr Gly Gly Ala Cys Ala Gly Ala Gly Thr Thr Gly Ala Gly
1340                1345                1350

Cys Thr Thr Thr Cys Thr Gly Gly Cys Thr Ala Cys Gly Gly Cys
1355                1360                1365

Ala Ala Gly Cys Ala Thr Gly Ala Gly Gly Cys Ala Thr Cys Cys
1370                1375                1380

Thr Cys Thr Cys Cys Thr Thr Cys Thr Thr Cys Thr Cys Thr
1385                1390                1395

Gly Ala Cys Cys Gly Gly Cys Thr Gly Ala Ala Gly Gly Ala Gly
1400                1405                1410

Gly Cys Thr Cys Ala Cys Gly Thr Cys Ala Gly Ala Cys Thr Gly
1415                1420                1425

Thr Ala Thr Cys Cys Gly Thr Cys Cys Ala Gly Cys Cys Gly Cys
1430                1435                1440

Thr Gly Thr Ala Cys Cys Thr Cys Ala Cys Ala Gly Cys Ala Thr
1445                1450                1455

Cys Thr Gly Thr Thr Thr Ala Ala Cys Ala Ala Ala Ala Cys Cys
1460                1465                1470

Ala Thr Cys Ala Cys Gly Ala Gly Cys Ala Ala Cys Ala Thr Gly
1475                1480                1485

Cys Thr Gly Thr Gly Thr Gly Cys Ala Gly Gly Ala Gly Ala Cys
1490                1495                1500

Ala Cys Cys Cys Gly Ala Ala Cys Thr Gly Gly Gly Gly Cys
1505                1510                1515

Ala Ala Cys Cys Ala Ala Gly Ala Cys Gly Thr Cys Cys Ala Thr
1520                1525                1530

Gly Ala Cys Gly Cys Gly Thr Gly Cys Cys Ala Gly Gly Gly Thr
1535                1540                1545

Gly Ala Cys Thr Cys Ala Gly Gly Ala Gly Gly Cys Cys Cys Thr
1550                1555                1560

Cys Thr Gly Gly Thr Gly Thr Gly Cys Ala Thr Gly Ala Thr Cys
1565                1570                1575

Gly Ala Thr Ala Ala Gly Cys Gly Gly Ala Thr Gly Ala Cys Thr
1580                1585                1590

Thr Thr Ala Cys Thr Gly Gly Gly Cys Ala Thr Cys Ala Thr Cys
1595 1600 1605

Ala Gly Cys Thr Gly Gly Gly Gly Cys Cys Thr Cys Gly Gly Cys
1610 1615 1620

Thr Gly Thr Gly Gly Gly Cys Ala Gly Ala Ala Gly Gly Ala Cys
1625 1630 1635

Gly Thr Gly Cys Cys Ala Gly Gly Gly Ala Thr Ala Thr Ala Cys
1640 1645 1650

Ala Cys Ala Ala Ala Gly Gly Thr Cys Ala Cys Thr Ala Ala Thr
1655 1660 1665

Thr Ala Cys Cys Thr Gly Ala Ala Cys Thr Gly Gly Ala Thr Thr
1670 1675 1680

Cys Ala Ala Gly Ala Cys Ala Ala Cys Ala Thr Gly Ala Ala Gly
1685 1690 1695

Cys Ala Ala Ala Ala Gly Cys Thr Thr Ala Ala Thr Thr Ala Gly
1700 1705 1710

Cys Thr Gly Ala Gly Cys Thr Thr Gly Gly Ala Cys Thr Cys Cys
1715 1720 1725

-continued

Thr Gly Thr Thr Gly Ala
    1730

<210> SEQ ID NO 16
<211> LENGTH: 1614
<212> TYPE: PRT
<213> ORGANISM: Rattus norvegicus

<400> SEQUENCE: 16

Thr Cys Cys Thr Ala Cys Ala Gly Ala Gly Cys Gly Ala Cys Cys Thr
1               5                   10                  15

Gly Cys Ala Gly Ala Gly Ala Thr Gly Ala Ala Cys Ala Gly Ala Cys
            20                  25                  30

Thr Cys Ala Gly Ala Cys Ala Ala Cys Thr Thr Ala Cys Cys Ala Ala
        35                  40                  45

Cys Ala Gly Cys Ala Thr Cys Ala Gly Thr Cys Ala Thr Gly Gly Cys
    50                  55                  60

Thr Ala Cys Gly Thr Cys Cys Ala Thr Gly Cys Thr Cys Ala Gly
65                  70                  75                  80

Ala Gly Gly Cys Ala Ala Thr Cys Gly Gly Thr Gly Gly Ala Ala
                85                  90                  95

Thr Ala Cys Thr Gly Cys Cys Gly Gly Thr Gly Cys Ala Ala Cys Ala
            100                 105                 110

Gly Cys Gly Gly Cys Cys Thr Gly Gly Cys Ala Cys Ala Gly Thr Gly
        115                 120                 125

Cys Cys Ala Cys Thr Cys Gly Gly Thr Gly Cys Cys Cys Gly Thr Cys
    130                 135                 140

Cys Gly Ala Ala Gly Thr Thr Gly Cys Ala Gly Thr Gly Ala Ala Cys
145                 150                 155                 160

Cys Gly Ala Gly Ala Thr Gly Cys Thr Thr Cys Ala Ala Thr Gly Gly
                165                 170                 175

Gly Gly Gly Thr Ala Cys Gly Thr Gly Thr Cys Ala Gly Cys Ala Gly
            180                 185                 190

Gly Cys Cys Cys Thr Gly Thr Ala Thr Thr Cys Thr Cys Thr Gly
        195                 200                 205

Ala Cys Thr Thr Cys Gly Thr Cys Thr Gly Cys Cys Ala Gly Thr Gly
    210                 215                 220

Cys Cys Cys Thr Gly Ala Cys Gly Gly Ala Thr Thr Thr Gly Thr Thr
225                 230                 235                 240

Gly Gly Gly Ala Ala Ala Cys Gly Cys Thr Gly Thr Gly Ala Thr Ala
                245                 250                 255

Thr Ala Gly Ala Thr Ala Cys Cys Ala Gly Ala Gly Cys Ala Ala Cys
            260                 265                 270

Cys Thr Gly Cys Thr Thr Cys Gly Ala Gly Gly Cys Cys Ala Gly
        275                 280                 285

Gly Gly Cys Ala Thr Cys Ala Cys Cys Thr Ala Cys Ala Gly Ala Gly
    290                 295                 300

Gly Cys Ala Cys Ala Thr Gly Gly Ala Gly Cys Ala Cys Ala Gly Cys
305                 310                 315                 320

Ala Gly Ala Ala Ala Ala Thr Gly Gly Gly Cys Thr Gly Ala Ala
                325                 330                 335

Thr Gly Cys Ala Thr Cys Ala Ala Cys Thr Gly Gly Ala Ala Thr Ala
            340                 345                 350

Gly Cys Ala Gly Thr Gly Cys Cys Cys Thr Gly Thr Cys Cys Cys Ala
        355                 360                 365

```
Gly Ala Ala Gly Cys Cys Thr Cys Ala Gly Thr Cys Ala
    370             375             380

Ala Gly Gly Ala Gly Cys Cys Ala Ala Thr Gly Cys Cys Ala
385             390             395             400

Thr Cys Ala Ala Gly Cys Thr Gly Gly Cys Cys Thr Thr Gly Gly
                405             410             415

Gly Ala Ala Cys Cys Ala Cys Ala Ala Thr Ala Cys Thr Gly Cys
            420             425             430

Ala Gly Ala Ala Ala Cys Cys Ala Gly Ala Cys Cys Gly Ala Gly
            435             440             445

Ala Cys Gly Thr Gly Ala Gly Cys Cys Cys Thr Gly Gly Thr Gly
    450             455             460

Cys Thr Ala Thr Gly Thr Cys Thr Thr Thr Ala Ala Gly Gly Cys Ala
465             470             475             480

Gly Gly Gly Ala Ala Gly Thr Ala Thr Ala Cys Cys Ala Cys Gly Gly
                485             490             495

Ala Gly Thr Thr Cys Thr Gly Cys Ala Gly Cys Ala Cys Gly Cys Cys
        500             505             510

Gly Gly Cys Thr Thr Gly Cys Cys Cys Thr Ala Ala Gly Gly Gly Ala
        515             520             525

Cys Cys Ala Ala Cys Thr Gly Ala Gly Gly Ala Cys Thr Gly Cys Thr
530             535             540

Ala Thr Gly Thr Thr Gly Gly Ala Ala Ala Gly Gly Thr Gly Thr
545             550             555             560

Gly Ala Cys Thr Thr Ala Cys Cys Gly Thr Gly Cys Ala Cys Cys
            565             570             575

Cys Ala Cys Ala Gly Cys Thr Thr Ala Cys Cys Ala Cys Ala Thr
        580             585             590

Cys Cys Ala Ala Gly Gly Cys Cys Thr Cys Thr Gly Cys Cys Thr
    595             600             605

Cys Cys Cys Ala Thr Gly Gly Ala Ala Thr Thr Cys Cys Ala Thr Gly
    610             615             620

Ala Thr Cys Cys Thr Gly Ala Thr Ala Gly Gly Cys Ala Ala Gly Ala
625             630             635             640

Cys Thr Thr Ala Cys Ala Cys Ala Gly Cys Gly Thr Gly Gly Ala Gly
                645             650             655

Gly Gly Cys Cys Ala Ala Cys Thr Cys Cys Ala Gly Gly Cys Ala
        660             665             670

Cys Thr Thr Gly Gly Cys Cys Thr Gly Gly Gly Cys Ala Gly Ala Cys
    675             680             685

Ala Cys Ala Ala Thr Thr Ala Thr Thr Gly Cys Cys Gly Gly Ala Ala
690             695             700

Cys Cys Cys Ala Gly Ala Thr Gly Gly Gly Ala Thr Gly Cys Cys
705             710             715             720

Ala Ala Ala Cys Cys Thr Thr Gly Gly Thr Gly Cys Cys Ala Cys Gly
        725             730             735

Thr Gly Ala Thr Gly Ala Ala Gly Gly Ala Cys Cys Gly Ala Ala Ala
            740             745             750

Gly Cys Thr Gly Ala Cys Ala Thr Gly Gly Ala Ala Thr Ala Thr
        755             760             765

Thr Gly Cys Gly Ala Cys Ala Thr Gly Thr Cys Cys Cys Cys Ala Thr
    770             775             780
```

-continued

```
Gly Cys Thr Cys Cys Ala Cys Cys Thr Gly Cys Gly Gly Cys Cys Thr
785                 790                 795                 800
Gly Ala Gly Gly Cys Ala Ala Thr Ala Cys Ala Ala Ala Cys Ala Gly
                805                 810                 815
Cys Cys Thr Cys Thr Gly Thr Thr Thr Cys Gly Ala Ala Thr Thr Ala
                820                 825                 830
Ala Ala Gly Gly Ala Gly Gly Ala Cys Thr Cys Thr Thr Cys Ala Cys
                835                 840                 845
Ala Gly Ala Cys Ala Thr Cys Ala Cys Cys Thr Cys Ala Cys Ala Cys
    850                 855                 860
Cys Cys Thr Thr Gly Gly Cys Ala Gly Gly Cys Cys Gly Cys Cys Ala
865                 870                 875                 880
Thr Cys Thr Thr Thr Gly Thr Cys Ala Ala Gly Ala Ala Cys Ala Ala
                885                 890                 895
Gly Ala Gly Gly Thr Cys Thr Cys Cys Ala Gly Gly Ala Gly Ala Gly
                900                 905                 910
Ala Gly Ala Thr Thr Cys Cys Thr Gly Thr Gly Thr Gly Gly Ala Gly
                915                 920                 925
Gly Gly Gly Thr Gly Cys Thr Gly Ala Thr Cys Ala Gly Thr Thr Cys
930                 935                 940
Cys Thr Gly Cys Thr Gly Gly Thr Gly Cys Thr Ala Thr Cys Thr Thr
945                 950                 955                 960
Gly Cys Cys Gly Cys Cys Ala Cys Thr Gly Cys Thr Thr Thr Thr Gly
                965                 970                 975
Thr Ala Gly Ala Gly Ala Gly Thr Thr Thr Cys Cys Ala Cys Cys Cys
                980                 985                 990
Cys Cys Ala Thr Cys Ala Thr Cys  Thr Thr Ala Ala Ala  Gly Thr Gly
        995                 1000                 1005
Gly Thr  Cys Thr Thr Gly Gly  Gly Cys Ala Gly Ala  Ala Cys Ala
         1010                 1015                 1020
Thr Ala  Cys Ala Gly Ala Gly  Thr Gly Gly Thr Cys  Cys Cys Thr
         1025                 1030                 1035
Gly Gly  Ala Gly Ala Gly Gly  Ala Gly Gly Ala Gly  Cys Ala Gly
         1040                 1045                 1050
Ala Cys  Ala Thr Thr Cys Gly  Ala Gly Ala Thr Cys  Gly Ala Ala
         1055                 1060                 1065
Ala Ala  Gly Thr Ala Cys Ala  Thr Ala Gly Thr Cys  Cys Ala Thr
         1070                 1075                 1080
Ala Ala  Gly Gly Ala Ala Thr  Thr Thr Gly Ala Thr  Gly Ala Cys
         1085                 1090                 1095
Gly Ala  Cys Ala Cys Thr Thr  Ala Thr Gly Ala Cys  Ala Ala Thr
         1100                 1105                 1110
Gly Ala  Cys Ala Thr Cys Gly  Cys Ala Thr Thr Ala  Cys Thr Gly
         1115                 1120                 1125
Cys Ala  Gly Cys Thr Gly Ala  Gly Gly Cys Ala  Gly Ala Thr
         1130                 1135                 1140
Thr Cys  Cys Ala Gly Thr Cys  Ala Gly Thr Gly Thr  G

```
                          1190                1195                1200
Gly Thr Ala Cys Ala Gly Cys Thr Thr Cys Cys Thr Gly Ala Cys
        1205                1210                1215

Thr Gly Gly Ala Cys Ala Gly Ala Gly Thr Gly Thr Gly Ala Gly
        1220                1225                1230

Cys Thr Thr Thr Cys Thr Gly Gly Cys Thr Ala Cys Gly Gly Cys
        1235                1240                1245

Ala Ala Gly Cys Ala Thr Gly Ala Gly Gly Cys Ala Thr Cys Cys
        1250                1255                1260

Thr Cys Thr Cys Cys Thr Thr Cys Thr Thr Cys Thr Cys Thr
        1265                1270                1275

Gly Ala Cys Cys Gly Gly Cys Thr Gly Ala Ala Gly Gly Ala Gly
        1280                1285                1290

Gly Cys Thr Cys Ala Cys Gly Thr Cys Ala Gly Ala Cys Thr Gly
        1295                1300                1305

Thr Ala Thr Cys Cys Gly Thr Cys Cys Ala Gly Cys Cys Gly Cys
        1310                1315                1320

Thr Gly Thr Ala Cys Cys Thr Cys Ala Cys Ala Gly Cys Ala Thr
        1325                1330                1335

Cys Thr Gly Thr Thr Thr Ala Ala Cys Ala Ala Ala Ala Cys Cys
        1340                1345                1350

Ala Thr Cys Ala Cys Gly Ala Gly Cys Ala Ala Cys Ala Thr Gly
        1355                1360                1365

Cys Thr Gly Thr Gly Thr Gly Cys Ala Gly Gly Ala Gly Ala Cys
        1370                1375                1380

Ala Cys Cys Cys Gly Ala Ala Cys Thr Gly Gly Gly Gly Cys
        1385                1390                1395

Ala Ala Cys Cys Ala Ala Gly Ala Cys Gly Thr Cys Cys Ala Thr
        1400                1405                1410

Gly Ala Cys Gly Cys Gly Thr Gly Cys Cys Ala Gly Gly Gly Thr
        1415                1420                1425

Gly Ala Cys Thr Cys Ala Gly Gly Ala Gly Gly Cys Cys Cys Thr
        1430                1435                1440

Cys Thr Gly Gly Thr Gly Thr Gly Cys Ala Thr Gly Ala Thr Cys
        1445                1450                1455

Gly Ala Thr Ala Ala Gly Cys Gly Gly Ala Thr Gly Ala Cys Thr
        1460                1465                1470

Thr Thr Ala Cys Thr Gly Gly Cys Ala Thr Cys Ala Thr Cys
        1475                1480                1485

Ala Gly Cys Thr Gly Gly Gly Gly Cys Cys Thr Cys Gly Gly Cys
        1490                1495                1500

Thr Gly Thr Gly Gly Gly Cys Ala Gly Ala Ala Gly Gly Ala Cys
        1505                1510                1515

Gly Thr Gly Cys Cys Ala Gly Gly Ala Thr Ala Thr Ala Cys
        1520                1525                1530

Ala Cys Ala Ala Ala Gly Gly Thr Cys Ala Cys Thr Ala Ala Thr
        1535                1540                1545

Thr Ala Cys Cys Thr Gly Ala Ala Cys Thr Gly Gly Ala Thr Thr
        1550                1555                1560

Cys Ala Ala Gly Ala Cys Ala Ala Cys Ala Thr Gly Ala Ala Gly
        1565                1570                1575

Cys Ala Ala Ala Ala Gly Cys Thr Thr Ala Ala Thr Thr Ala Gly
        1580                1585                1590
```

Cys Thr Gly Ala Gly Cys Thr Thr Gly Gly Ala Cys Thr Cys Cys
1595                1600                1605

Thr Gly  Thr Thr Gly Ala
    1610

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
ccgggatcct cctacagagc gacc                                              24

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
ggcaagcttt tgcttcatgt tgtcttgaat ccagtt                                 36

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
caggccgcac gtggagtcct gagttggtcc cttagg                                 36

<210> SEQ ID NO 20
<211> LENGTH: 15
<212> TYPE: DNA
<213> ORGANISM: Artificial Sequence
<220> FEATURE:
<223> OTHER INFORMATION: primer

<400> SEQUENCE: 20
tccacctgcg gcctg                                                        15

<210> SEQ ID NO 21
<211> LENGTH: 37
<212> TYPE: DNA
<213> ORGANISM: Artificial Sequence
<220> FEATURE:
<223> OTHER INFORMATION: primer

<400> SEQUENCE: 21
ggaccgaaag ctgacacggg aatattgcga catgtcc                                37

<210> SEQ ID NO 22
<211> LENGTH: 38
<212> TYPE: DNA
<213> ORGANISM: Artificial Sequence
<220> FEATURE:
<223> OTHER INFORMATION: primer

<400> SEQUENCE: 22
ggacatgtcg caatattccc gtggtcagct ttcggtcc                               38

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
tacaaacagc ctctgtttcg aattaaagga gga         33

<210> SEQ ID NO 24
<211> LENGTH: 33
<212> TYPE: DNA
<213> ORGANISM: Artificial Sequence
<220> FEATURE:
<223> OTHER INFORMATION: primer

<400> SEQUENCE: 24
tcctccttta attcgaaaca gaggctgttt gta         33

<210> SEQ ID NO 25
<211> LENGTH: 275
<212> TYPE: PRT
<213> ORGANISM: Homo sapiens

<400> SEQUENCE: 25

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
        35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

-continued

```
Asp Val Pro Ser Cys Ser Thr Cys Gly Leu Arg Gln Tyr Ser Gln Pro
            260                 265                 270

Gln Phe Arg
        275

<210> SEQ ID NO 26
<211> LENGTH: 252
<212> TYPE: PRT
<213> ORGANISM: Homo sapiens

<400> SEQUENCE: 26

Ile Lys Gly Gly Leu Phe Ala Asp Ile Ala Ser His Pro Trp Gln Ala
1               5                   10                  15

Ala Ile Phe Ala Lys His Arg Arg Ser Pro Gly Glu Arg Phe Leu Cys
            20                  25                  30

Gly Gly Ile Leu Ile Ser Ser Cys Trp Ile Leu Ser Ala Ala His Cys
        35                  40                  45

Phe Gln Glu Arg Phe Pro Pro His His Leu Thr Val Ile Leu Gly Arg
    50                  55                  60

Thr Tyr Arg Val Val Pro Gly Glu Glu Gln Lys Phe Glu Val Glu
65                  70                  75                  80

Lys Tyr Ile Val His Lys Glu Phe Asp Asp Thr Tyr Asp Asn Asp
                85                  90                  95

Ile Ala Leu Leu Gln Leu Lys Ser Asp Ser Ser Arg Cys Ala Gln Glu
            100                 105                 110

Ser Ser Val Val Arg Thr Val Cys Leu Pro Pro Ala Asp Leu Gln Leu
        115                 120                 125

Pro Asp Trp Thr Glu Cys Glu Leu Ser Gly Tyr Gly Lys His Glu Ala
    130                 135                 140

Leu Ser Pro Phe Tyr Ser Glu Arg Leu Lys Glu Ala His Val Arg Leu
145                 150                 155                 160

Tyr Pro Ser Ser Arg Cys Thr Ser Gln His Leu Leu Asn Arg Thr Val
                165                 170                 175

Thr Asp Asn Met Leu Cys Ala Gly Asp Thr Arg Ser Gly Gly Pro Gln
            180                 185                 190

Ala Asn Leu His Asp Ala Cys Gln Gly Asp Ser Gly Gly Pro Leu Val
        195                 200                 205

Cys Leu Asn Asp Gly Arg Met Thr Leu Val Gly Ile Ile Ser Trp Gly
    210                 215                 220

Leu Gly Cys Gly Gln Lys Asp Val Pro Gly Val Tyr Thr Lys Val Thr
225                 230                 235                 240

Asn Tyr Leu Asp Trp Ile Arg Asp Asn Met Arg Pro
                245                 250

<210> SEQ ID NO 27
<211> LENGTH: 535
<212> TYPE: PRT
<213> ORGANISM: Artificial Sequence
<220> FEATURE:
<223> OTHER INFORMATION: his tPA

<400> SEQUENCE: 27

His His His His His His Gly Ser Ser Tyr Gln Val Ile Cys Arg Asp
1               5                   10                  15

Glu Lys Thr Gln Met Ile Tyr Gln Gln His Gln Ser Trp Leu Arg Pro
            20                  25                  30
```

-continued

Val Leu Arg Ser Asn Arg Val Glu Tyr Cys Trp Cys Asn Ser Gly Arg
         35                  40                  45

Ala Gln Cys His Ser Val Pro Val Lys Ser Cys Ser Glu Pro Arg Cys
 50                  55                  60

Phe Asn Gly Gly Thr Cys Gln Gln Ala Leu Tyr Phe Ser Asp Phe Val
 65                  70                  75                  80

Cys Gln Cys Pro Glu Gly Phe Ala Gly Lys Cys Cys Glu Ile Asp Thr
                 85                  90                  95

Arg Ala Thr Cys Tyr Glu Asp Gln Gly Ile Ser Tyr Arg Gly Thr Trp
             100                 105                 110

Ser Thr Ala Glu Ser Gly Ala Glu Cys Thr Asn Trp Asn Ser Ser Ala
         115                 120                 125

Leu Ala Gln Lys Pro Tyr Ser Gly Arg Arg Pro Asp Ala Ile Arg Leu
130                 135                 140

Gly Leu Gly Asn His Asn Tyr Cys Arg Asn Pro Asp Arg Asp Ser Lys
145                 150                 155                 160

Pro Trp Cys Tyr Val Phe Lys Ala Gly Lys Tyr Ser Ser Glu Phe Cys
                165                 170                 175

Ser Thr Pro Ala Cys Ser Glu Gly Asn Ser Asp Cys Tyr Phe Gly Asn
            180                 185                 190

Gly Ser Ala Tyr Arg Gly Thr His Ser Leu Thr Glu Ser Gly Ala Ser
        195                 200                 205

Cys Leu Pro Trp Asn Ser Met Ile Leu Ile Gly Lys Val Tyr Thr Ala
    210                 215                 220

Gln Asn Pro Ser Ala Gln Ala Leu Gly Leu Gly Lys His Asn Tyr Cys
225                 230                 235                 240

Arg Asn Pro Asp Gly Asp Ala Lys Pro Trp Cys His Val Leu Lys Asn
                245                 250                 255

Arg Arg Leu Thr Trp Glu Tyr Cys Asp Val Pro Ser Cys Ser Thr Cys
            260                 265                 270

Gly Leu Arg Gln Tyr Ser Gln Pro Gln Phe Arg Ile Lys Gly Gly Leu
        275                 280                 285

Phe Ala Asp Ile Ala Ser His Pro Trp Gln Ala Ala Ile Phe Ala Lys
    290                 295                 300

His Arg Arg Ser Pro Gly Glu Arg Phe Leu Cys Gly Gly Ile Leu Ile
305                 310                 315                 320

Ser Ser Cys Trp Ile Leu Ser Ala Ala His Cys Phe Gln Glu Arg Phe
                325                 330                 335

Pro Pro His His Leu Thr Val Ile Leu Gly Arg Thr Tyr Arg Val Val
            340                 345                 350

Pro Gly Glu Glu Glu Gln Lys Phe Glu Val Glu Lys Tyr Ile Val His
        355                 360                 365

Lys Glu Phe Asp Asp Asp Thr Tyr Asp Asn Asp Ile Ala Leu Leu Gln
    370                 375                 380

Leu Lys Ser Asp Ser Ser Arg Cys Ala Gln Glu Ser Ser Val Val Arg
385                 390                 395                 400

Thr Val Cys Leu Pro Pro Ala Asp Leu Gln Leu Pro Asp Trp Thr Glu
                405                 410                 415

Cys Glu Leu Ser Gly Tyr Gly Lys His Glu Ala Leu Ser Pro Phe Tyr
            420                 425                 430

Ser Glu Arg Leu Lys Glu Ala His Val Arg Leu Tyr Pro Ser Ser Arg
        435                 440                 445

Cys Thr Ser Gln His Leu Leu Asn Arg Thr Val Thr Asp Asn Met Leu

```
                450            455            460
Cys Ala Gly Asp Thr Arg Ser Gly Pro Gln Ala Asn Leu His Asp
465            470            475            480

Ala Cys Gln Gly Asp Ser Gly Gly Pro Leu Val Cys Leu Asn Asp Gly
                485            490                495

Arg Met Thr Leu Val Gly Ile Ile Ser Trp Gly Leu Gly Cys Gly Gln
            500                505                510

Lys Asp Val Pro Gly Val Tyr Thr Lys Val Thr Asn Tyr Leu Asp Trp
            515                520            525

Ile Arg Asp Asn Met Arg Pro
530                535

<210> SEQ ID NO 28
<211> LENGTH: 535
<212> TYPE: PRT
<213> ORGANISM: Artificial Sequence
<220> FEATURE:
<223> OTHER INFORMATION: his tPA

<400> SEQUENCE: 28

His His His His His His Gly Ser Ser Tyr Gln Val Ile Cys Arg Asp
1               5                   10                  15

Glu Lys Thr Gln Met Ile Tyr Gln Gln His Gln Ser Trp Leu Arg Pro
            20                  25                  30

Val Leu Arg Ser Asn Arg Val Glu Tyr Cys Trp Cys Asn Ser Gly Arg
        35                  40                  45

Ala Gln Cys His Ser Val Pro Val Lys Ser Cys Ser Glu Pro Arg Cys
50                  55                  60

Phe Asn Gly Gly Thr Cys Gln Gln Ala Leu Tyr Phe Ser Asp Phe Val
65                  70                  75                  80

Cys Gln Cys Pro Glu Gly Phe Ala Gly Lys Cys Cys Glu Ile Asp Thr
                85                  90                  95

Arg Ala Thr Cys Tyr Glu Asp Gln Gly Ile Ser Tyr Arg Gly Thr Trp
            100                 105                 110

Ser Thr Ala Glu Ser Gly Ala Glu Cys Thr Asn Trp Asn Ser Ser Ala
        115                 120                 125

Leu Ala Gln Lys Pro Tyr Ser Gly Arg Arg Pro Asp Ala Ile Arg Leu
130                 135                 140

Gly Leu Gly Asn His Asn Tyr Cys Arg Asn Pro Asp Arg Asp Ser Lys
145                 150                 155                 160

Pro Trp Cys Tyr Val Phe Lys Ala Gly Lys Tyr Ser Ser Glu Phe Cys
                165                 170                 175

Ser Thr Pro Ala Cys Ser Glu Gly Asn Ser Asp Cys Tyr Phe Gly Asn
            180                 185                 190

Gly Ser Ala Tyr Arg Gly Thr His Ser Leu Thr Glu Ser Gly Ala Ser
        195                 200                 205

Cys Leu Pro Trp Asn Ser Met Ile Leu Ile Gly Lys Val Tyr Thr Ala
210                 215                 220

Gln Asn Pro Ser Ala Gln Ala Leu Gly Leu Gly Lys His Asn Tyr Cys
225                 230                 235                 240

Arg Asn Pro Asp Gly Asp Ala Lys Pro Trp Cys His Val Leu Lys Asn
                245                 250                 255

Arg Arg Leu Thr Arg Glu Tyr Cys Asp Val Pro Ser Cys Ser Thr Cys
            260                 265                 270

Gly Leu Arg Gln Tyr Ser Gln Pro Gln Phe Arg Ile Lys Gly Gly Leu
```

```
            275                 280                 285
Phe Ala Asp Ile Ala Ser His Pro Trp Gln Ala Ile Phe Ala Lys
290                 295                 300
His Arg Arg Ser Pro Gly Glu Arg Phe Leu Cys Gly Gly Ile Leu Ile
305                 310                 315                 320
Ser Ser Cys Trp Ile Leu Ser Ala Ala His Cys Phe Gln Glu Arg Phe
                325                 330                 335
Pro Pro His His Leu Thr Val Ile Leu Gly Arg Thr Tyr Arg Val Val
            340                 345                 350
Pro Gly Glu Glu Glu Gln Lys Phe Glu Val Glu Lys Tyr Ile Val His
            355                 360                 365
Lys Glu Phe Asp Asp Asp Thr Tyr Asp Asn Asp Ile Ala Leu Leu Gln
370                 375                 380
Leu Lys Ser Asp Ser Ser Arg Cys Ala Gln Glu Ser Ser Val Val Arg
385                 390                 395                 400
Thr Val Cys Leu Pro Pro Ala Asp Leu Gln Leu Pro Asp Trp Thr Glu
                405                 410                 415
Cys Glu Leu Ser Gly Tyr Gly Lys His Glu Ala Leu Ser Pro Phe Tyr
                420                 425                 430
Ser Glu Arg Leu Lys Glu Ala His Val Arg Leu Tyr Pro Ser Ser Arg
            435                 440                 445
Cys Thr Ser Gln His Leu Leu Asn Arg Thr Val Thr Asp Asn Met Leu
450                 455                 460
Cys Ala Gly Asp Thr Arg Ser Gly Gly Pro Gln Ala Asn Leu His Asp
465                 470                 475                 480
Ala Cys Gln Gly Asp Ser Gly Gly Pro Leu Val Cys Leu Asn Asp Gly
                485                 490                 495
Arg Met Thr Leu Val Gly Ile Ile Ser Trp Gly Leu Gly Cys Gly Gln
                500                 505                 510
Lys Asp Val Pro Gly Val Tyr Thr Lys Val Thr Asn Tyr Leu Asp Trp
            515                 520                 525
Ile Arg Asp Asn Met Arg Pro
530                 535

<210> SEQ ID NO 29
<211> LENGTH: 535
<212> TYPE: PRT
<213> ORGANISM: Artificial Sequence
<220> FEATURE:
<223> OTHER INFORMATION: his tPA

<400> SEQUENCE: 29

His His His His His His Gly Ser Ser Tyr Gln Val Ile Cys Arg Asp
1               5                   10                  15
Glu Lys Thr Gln Met Ile Tyr Gln Gln His Gln Ser Trp Leu Arg Pro
                20                  25                  30
Val Leu Arg Ser Asn Arg Val Glu Tyr Cys Trp Cys Asn Ser Gly Arg
            35                  40                  45
Ala Gln Cys His Ser Val Pro Val Lys Ser Cys Ser Glu Pro Arg Cys
50                  55                  60
Phe Asn Gly Gly Thr Cys Gln Gln Ala Leu Tyr Phe Ser Asp Phe Val
65                  70                  75                  80
Cys Gln Cys Pro Glu Gly Phe Ala Gly Lys Cys Cys Glu Ile Asp Thr
                85                  90                  95
Arg Ala Thr Cys Tyr Glu Asp Gln Gly Ile Ser Tyr Arg Gly Thr Trp
```

```
               100                 105                 110
Ser Thr Ala Glu Ser Gly Ala Glu Cys Thr Asn Trp Asn Ser Ser Ala
            115                 120                 125

Leu Ala Gln Lys Pro Tyr Ser Gly Arg Arg Pro Asp Ala Ile Arg Leu
        130                 135                 140

Gly Leu Gly Asn His Asn Tyr Cys Arg Asn Pro Asp Arg Asp Ser Lys
145                 150                 155                 160

Pro Trp Cys Tyr Val Phe Lys Ala Gly Lys Tyr Ser Ser Glu Phe Cys
                165                 170                 175

Ser Thr Pro Ala Cys Ser Glu Gly Asn Ser Asp Cys Tyr Phe Gly Asn
            180                 185                 190

Gly Ser Ala Tyr Arg Gly Thr His Ser Leu Thr Glu Ser Gly Ala Ser
        195                 200                 205

Cys Leu Pro Trp Asn Ser Met Ile Leu Ile Gly Lys Val Tyr Thr Ala
    210                 215                 220

Gln Asn Pro Ser Ala Gln Ala Leu Gly Leu Gly Lys His Asn Tyr Cys
225                 230                 235                 240

Arg Asn Pro Asp Gly Asp Ala Lys Pro Trp Cys His Val Leu Lys Asn
                245                 250                 255

Arg Arg Leu Thr Trp Glu Tyr Cys Asp Val Pro Ser Cys Ser Thr Cys
            260                 265                 270

Gly Leu Arg Gln Tyr Ser Gln Pro Gln Phe Ser Ile Lys Gly Gly Leu
        275                 280                 285

Phe Ala Asp Ile Ala Ser His Pro Trp Gln Ala Ala Ile Phe Ala Lys
    290                 295                 300

His Arg Arg Ser Pro Gly Glu Arg Phe Leu Cys Gly Gly Ile Leu Ile
305                 310                 315                 320

Ser Ser Cys Trp Ile Leu Ser Ala Ala His Cys Phe Gln Glu Arg Phe
                325                 330                 335

Pro Pro His His Leu Thr Val Ile Leu Gly Arg Thr Tyr Arg Val Val
            340                 345                 350

Pro Gly Glu Glu Glu Gln Lys Phe Glu Val Glu Lys Tyr Ile Val His
        355                 360                 365

Lys Glu Phe Asp Asp Asp Thr Tyr Asp Asn Asp Ile Ala Leu Leu Gln
    370                 375                 380

Leu Lys Ser Asp Ser Ser Arg Cys Ala Gln Glu Ser Ser Val Val Arg
385                 390                 395                 400

Thr Val Cys Leu Pro Pro Ala Asp Leu Gln Leu Pro Asp Trp Thr Glu
                405                 410                 415

Cys Glu Leu Ser Gly Tyr Gly Lys His Glu Ala Leu Ser Pro Phe Tyr
            420                 425                 430

Ser Glu Arg Leu Lys Glu Ala His Val Arg Leu Tyr Pro Ser Ser Arg
        435                 440                 445

Cys Thr Ser Gln His Leu Leu Asn Arg Thr Val Thr Asp Asn Met Leu
    450                 455                 460

Cys Ala Gly Asp Thr Arg Ser Gly Gly Pro Gln Ala Asn Leu His Asp
465                 470                 475                 480

Ala Cys Gln Gly Asp Ser Gly Gly Pro Leu Val Cys Leu Asn Asp Gly
                485                 490                 495

Arg Met Thr Leu Val Gly Ile Ile Ser Trp Gly Leu Gly Cys Gly Gln
            500                 505                 510

Lys Asp Val Pro Gly Val Tyr Thr Lys Val Thr Asn Tyr Leu Asp Trp
        515                 520                 525
```

Ile Arg Asp Asn Met Arg Pro
530                 535

<210> SEQ ID NO 30
<211> LENGTH: 535
<212> TYPE: PRT
<213> ORGANISM: Artificial Sequence
<220> FEATURE:
<223> OTHER INFORMATION: his tPA

<400> SEQUENCE: 30

His His His His His His Gly Ser Ser Tyr Gln Val Ile Cys Arg Asp
1               5                   10                  15

Glu Lys Thr Gln Met Ile Tyr Gln Gln His Gln Ser Trp Leu Arg Pro
            20                  25                  30

Val Leu Arg Ser Asn Arg Val Glu Tyr Cys Trp Cys Asn Ser Gly Arg
        35                  40                  45

Ala Gln Cys His Ser Val Pro Val Lys Ser Cys Ser Glu Pro Arg Cys
    50                  55                  60

Phe Asn Gly Gly Thr Cys Gln Gln Ala Leu Tyr Phe Ser Asp Phe Val
65                  70                  75                  80

Cys Gln Cys Pro Glu Gly Phe Ala Gly Lys Cys Cys Glu Ile Asp Thr
                85                  90                  95

Arg Ala Thr Cys Tyr Glu Asp Gln Gly Ile Ser Tyr Arg Gly Thr Trp
            100                 105                 110

Ser Thr Ala Glu Ser Gly Ala Glu Cys Thr Asn Trp Asn Ser Ser Ala
        115                 120                 125

Leu Ala Gln Lys Pro Tyr Ser Gly Arg Arg Pro Asp Ala Ile Arg Leu
    130                 135                 140

Gly Leu Gly Asn His Asn Tyr Cys Arg Asn Pro Asp Arg Asp Ser Lys
145                 150                 155                 160

Pro Trp Cys Tyr Val Phe Lys Ala Gly Lys Tyr Ser Ser Glu Phe Cys
                165                 170                 175

Ser Thr Pro Ala Cys Ser Glu Gly Asn Ser Asp Cys Tyr Phe Gly Asn
            180                 185                 190

Gly Ser Ala Tyr Arg Gly Thr His Ser Leu Thr Glu Ser Gly Ala Ser
        195                 200                 205

Cys Leu Pro Trp Asn Ser Met Ile Leu Ile Gly Lys Val Tyr Thr Ala
    210                 215                 220

Gln Asn Pro Ser Ala Gln Ala Leu Gly Leu Gly Lys His Asn Tyr Cys
225                 230                 235                 240

Arg Asn Pro Asp Gly Asp Ala Lys Pro Trp Cys His Val Leu Lys Asn
                245                 250                 255

Arg Arg Leu Thr Arg Glu Tyr Cys Asp Val Pro Ser Cys Ser Thr Cys
            260                 265                 270

Gly Leu Arg Gln Tyr Ser Gln Pro Gln Phe Ser Ile Lys Gly Gly Leu
        275                 280                 285

Phe Ala Asp Ile Ala Ser His Pro Trp Gln Ala Ala Ile Phe Ala Lys
    290                 295                 300

His Arg Arg Ser Pro Gly Glu Arg Phe Leu Cys Gly Gly Ile Leu Ile
305                 310                 315                 320

Ser Ser Cys Trp Ile Leu Ser Ala Ala His Cys Phe Gln Glu Arg Phe
                325                 330                 335

Pro Pro His His Leu Thr Val Ile Leu Gly Arg Thr Tyr Arg Val Val
            340                 345                 350

```
Pro Gly Glu Glu Gln Lys Phe Glu Val Glu Lys Tyr Ile Val His
        355                 360                 365

Lys Glu Phe Asp Asp Asp Thr Tyr Asp Asn Asp Ile Ala Leu Leu Gln
370                 375                 380

Leu Lys Ser Asp Ser Ser Arg Cys Ala Gln Glu Ser Ser Val Val Arg
385                 390                 395                 400

Thr Val Cys Leu Pro Pro Ala Asp Leu Gln Leu Pro Asp Trp Thr Glu
                405                 410                 415

Cys Glu Leu Ser Gly Tyr Gly Lys His Glu Ala Leu Ser Pro Phe Tyr
            420                 425                 430

Ser Glu Arg Leu Lys Glu Ala His Val Arg Leu Tyr Pro Ser Ser Arg
        435                 440                 445

Cys Thr Ser Gln His Leu Leu Asn Arg Thr Val Thr Asp Asn Met Leu
    450                 455                 460

Cys Ala Gly Asp Thr Arg Ser Gly Gly Pro Gln Ala Asn Leu His Asp
465                 470                 475                 480

Ala Cys Gln Gly Asp Ser Gly Gly Pro Leu Val Cys Leu Asn Asp Gly
                485                 490                 495

Arg Met Thr Leu Val Gly Ile Ile Ser Trp Gly Leu Gly Cys Gly Gln
            500                 505                 510

Lys Asp Val Pro Gly Val Tyr Thr Lys Val Thr Asn Tyr Leu Asp Trp
        515                 520                 525

Ile Arg Asp Asn Met Arg Pro
530                 535

<210> SEQ ID NO 31
<211> LENGTH: 535
<212> TYPE: PRT
<213> ORGANISM: Artificial Sequence
<220> FEATURE:
<223> OTHER INFORMATION: his tPA

<400> SEQUENCE: 31

His His His His His His Gly Ser Ser Tyr Gln Val Ile Cys Arg Asp
1               5                   10                  15

Glu Lys Thr Gln Met Ile Tyr Gln Gln His Gln Ser Trp Leu Arg Pro
            20                  25                  30

Val Leu Arg Ser Asn Arg Val Glu Tyr Cys Trp Cys Asn Ser Gly Arg
        35                  40                  45

Ala Gln Cys His Ser Val Pro Val Lys Ser Cys Ser Glu Pro Arg Cys
    50                  55                  60

Phe Asn Gly Gly Thr Cys Gln Gln Ala Leu Tyr Phe Ser Asp Phe Val
65                  70                  75                  80

Cys Gln Cys Pro Glu Gly Phe Ala Gly Lys Cys Cys Glu Ile Asp Thr
                85                  90                  95

Arg Ala Thr Cys Tyr Glu Asp Gln Gly Ile Ser Tyr Arg Gly Thr Trp
            100                 105                 110

Ser Thr Ala Glu Ser Gly Ala Glu Cys Thr Asn Trp Asn Ser Ser Ala
        115                 120                 125

Leu Ala Gln Lys Arg Tyr Ser Gly Arg Arg Pro Asp Ala Ile Arg Leu
    130                 135                 140

Gly Leu Gly Asn His Asn Tyr Cys Arg Asn Pro Asp Arg Asp Ser Lys
145                 150                 155                 160

Pro Trp Cys Tyr Val Phe Lys Ala Gly Lys Tyr Ser Ser Glu Phe Cys
                165                 170                 175
```

Ser Thr Pro Ala Cys Ser Glu Gly Asn Ser Asp Cys Tyr Phe Gly Asn
            180                 185                 190

Gly Ser Ala Tyr Arg Gly Thr His Ser Leu Thr Glu Ser Gly Ala Ser
        195                 200                 205

Cys Leu Pro Trp Asn Ser Met Ile Leu Ile Gly Lys Val Tyr Thr Ala
    210                 215                 220

Gln Asn Pro Ser Ala Gln Ala Leu Gly Leu Gly Lys His Asn Tyr Cys
225                 230                 235                 240

Arg Asn Pro Asp Gly Asp Ala Lys Pro Trp Cys His Val Leu Lys Asn
                245                 250                 255

Arg Arg Leu Thr Arg Glu Tyr Cys Asp Val Pro Ser Cys Ser Thr Cys
            260                 265                 270

Gly Leu Arg Gln Tyr Ser Gln Pro Gln Phe Ser Ile Lys Gly Gly Leu
        275                 280                 285

Phe Ala Asp Ile Ala Ser His Pro Trp Gln Ala Ala Ile Phe Ala Lys
    290                 295                 300

His Arg Arg Ser Pro Gly Glu Arg Phe Leu Cys Gly Gly Ile Leu Ile
305                 310                 315                 320

Ser Ser Cys Trp Ile Leu Ser Ala Ala His Cys Phe Gln Glu Arg Phe
                325                 330                 335

Pro Pro His His Leu Thr Val Ile Leu Gly Arg Thr Tyr Arg Val Val
            340                 345                 350

Pro Gly Glu Glu Glu Gln Lys Phe Glu Val Glu Lys Tyr Ile Val His
        355                 360                 365

Lys Glu Phe Asp Asp Asp Thr Tyr Asp Asn Asp Ile Ala Leu Leu Gln
    370                 375                 380

Leu Lys Ser Asp Ser Ser Arg Cys Ala Gln Glu Ser Ser Val Val Arg
385                 390                 395                 400

Thr Val Cys Leu Pro Pro Ala Asp Leu Gln Leu Pro Asp Trp Thr Glu
                405                 410                 415

Cys Glu Leu Ser Gly Tyr Gly Lys His Glu Ala Leu Ser Pro Phe Tyr
            420                 425                 430

Ser Glu Arg Leu Lys Glu Ala His Val Arg Leu Tyr Pro Ser Ser Arg
        435                 440                 445

Cys Thr Ser Gln His Leu Leu Asn Arg Thr Val Thr Asp Asn Met Leu
    450                 455                 460

Cys Ala Gly Asp Thr Arg Ser Gly Gly Pro Gln Ala Asn Leu His Asp
465                 470                 475                 480

Ala Cys Gln Gly Asp Ser Gly Gly Pro Leu Val Cys Leu Asn Asp Gly
                485                 490                 495

Arg Met Thr Leu Val Gly Ile Ile Ser Trp Gly Leu Gly Cys Gly Gln
            500                 505                 510

Lys Asp Val Pro Gly Val Tyr Thr Lys Val Thr Asn Tyr Leu Asp Trp
        515                 520                 525

Ile Arg Asp Asn Met Arg Pro
    530                 535

<210> SEQ ID NO 32
<211> LENGTH: 31
<212> TYPE: DNA
<213> ORGANISM: Artificial Sequence
<220> FEATURE:
<223> OTHER INFORMATION: primer

<400> SEQUENCE: 32

```
ggcgctagca tggatgcaat gaagagaggg c                              31

<210> SEQ ID NO 33
<211> LENGTH: 39
<212> TYPE: DNA
<213> ORGANISM: Artificial Sequence
<220> FEATURE:
<223> OTHER INFORMATION: primer

<400> SEQUENCE: 33
ccgggcaagc ttttgcttca tgttgtcttg aatccagtt                      39

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
gccaagcccc ggtgccacgt gc                                        22

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
gcacgtggca ccggggcttg gc                                        22

<210> SEQ ID NO 36
<211> LENGTH: 35
<212> TYPE: DNA
<213> ORGANISM: Artificial Sequence
<220> FEATURE:
<223> OTHER INFORMATION: primer

<400> SEQUENCE: 36
gtacagccag cctcagttta gcatcaaagg agggc                          35

<210> SEQ ID NO 37
<211> LENGTH: 32
<212> TYPE: DNA
<213> ORGANISM: Artificial Sequence
<220> FEATURE:
<223> OTHER INFORMATION: primer

<400> SEQUENCE: 37
aaactgaggc tggctgtact gtctcaggcc gc                             32

<210> SEQ ID NO 38
<211> LENGTH: 33
<212> TYPE: DNA
<213> ORGANISM: Artificial Sequence
<220> FEATURE:
<223> OTHER INFORMATION: primer

<400> SEQUENCE: 38
gcagcgcgtt ggcccagaag cgctacagcg ggc                            33

<210> SEQ ID NO 39
<211> LENGTH: 32
<212> TYPE: DNA
```

<213> ORGANISM: Artificial Sequence
<220> FEATURE:
<223> OTHER INFORMATION: primer

<400> SEQUENCE: 39
cttctgggcc aacgcgctgc tgttccagtt gg             32

<210> SEQ ID NO 40
<211> LENGTH: 53
<212> TYPE: PRT
<213> ORGANISM: Artificial Sequence
<220> FEATURE:
<223> OTHER INFORMATION: Synthetic peptide - Rat-tPA-K1

<400> SEQUENCE: 40

Leu Ser Gln Lys Pro Tyr Ser Ala Arg Arg Pro Asn Ala Ile Lys Leu
1               5                   10                  15

Gly Leu Gly Asn His Asn Tyr Cys Arg Asn Pro Asp Arg Asp Val Lys
            20                  25                  30

Pro Trp Cys Tyr Val Phe Lys Ala Gly Lys Tyr Thr Thr Glu Phe Cys
        35                  40                  45

Ser Thr Pro Ala Cys
    50

<210> SEQ ID NO 41
<211> LENGTH: 53
<212> TYPE: PRT
<213> ORGANISM: Artificial Sequence
<220> FEATURE:
<223> OTHER INFORMATION: Synthetic peptide - DSPA-K

<400> SEQUENCE: 41

Leu Thr Arg Arg Thr Tyr Asn Gly Arg Met Pro Asp Ala Phe Asn Leu
1               5                   10                  15

Gly Leu Gly Asn His Asn Tyr Cys Arg Asn Pro Asn Gly Ala Pro Lys
            20                  25                  30

Pro Trp Cys Tyr Val Ile Lys Ala Gly Lys Phe Thr Ser Glu Ser Cys
        35                  40                  45

Ser Val Pro Val Cys
    50

<210> SEQ ID NO 42
<211> LENGTH: 53
<212> TYPE: PRT
<213> ORGANISM: Artificial Sequence
<220> FEATURE:
<223> OTHER INFORMATION: Synthetic peptide - Rat-tPA-K2

<400> SEQUENCE: 42

Leu Ile Gly Lys Thr Tyr Thr Ala Trp Arg Ala Asn Ser Gln Ala Leu
1               5                   10                  15

Gly Leu Gly Arg His Asn Tyr Cys Arg Asn Pro Asp Gly Asp Ala Lys
            20                  25                  30

Pro Trp Cys His Val Met Lys Asp Arg Lys Leu Thr Trp Glu Tyr Cys
        35                  40                  45

Asp Met Ser Pro Cys
    50

<210> SEQ ID NO 43
<211> LENGTH: 21
<212> TYPE: PRT
<213> ORGANISM: Artificial Sequence

```
<220> FEATURE:
<223> OTHER INFORMATION: Synthetic peptide - Rat-tPA

<400> SEQUENCE: 43

Gly Leu Arg Gln Tyr Lys Gln Pro Gln Phe Arg Ile Lys Gly Gly Leu
1               5                   10                  15

Phe Thr Asp Ile Thr
            20

<210> SEQ ID NO 44
<211> LENGTH: 21
<212> TYPE: PRT
<213> ORGANISM: Artificial Sequence
<220> FEATURE:
<223> OTHER INFORMATION: Synthetic peptide - DSPA-a1

<400> SEQUENCE: 44

Gly Leu Arg Lys Tyr Lys Glu Pro Gln Glu His Ser Thr Gly Gly Leu
1               5                   10                  15

Phe Thr Asp Ile Thr
            20

<210> SEQ ID NO 45
<211> LENGTH: 4
<212> TYPE: PRT
<213> ORGANISM: Artificial Sequence
<220> FEATURE:
<223> OTHER INFORMATION: Synthetic peptide - residues 296-299 of SEQ ID
      NO: 2

<400> SEQUENCE: 45

Lys His Arg Arg
1

<210> SEQ ID NO 46
<211> LENGTH: 4
<212> TYPE: PRT
<213> ORGANISM: Artificial Sequence
<220> FEATURE:
<223> OTHER INFORMATION: Synthetic peptide

<400> SEQUENCE: 46

Ala Ala Ala Ala
1
```

MUTATED TISSUE PLASMINOGEN ACTIVATORS AND USES THEREOF

CROSS-REFERENCE TO RELATED APPLICATIONS

This application is a divisional of U.S. patent application Ser. No. 14/342,164 filed on Feb. 28, 2014, now U.S. Pat. No. 9,249,406, which itself was a Rule 371 national stage filing of PCT/EP2016/067540 filed Sep. 7, 2012 which claimed priority to European Application 11306119.6 filed Sep. 8, 2011.

FIELD OF THE INVENTION

The invention relates to mutated tissue plasminogen activators (tPA) and their use for treating thrombotic and haemorrhagic diseases, preferably intra-cerebral haemorrhages and ocular haemorrhages, more preferably thrombotic neurological disorders and central retinal artery occlusion, most preferably stroke.

BACKGROUND OF THE INVENTION

Tissue type plasminogen activator (tPA) is a serine protease secreted in the neurovascular unit (NVU) by endothelial cells (Angles-Cano et al., 1985), neurons (Pecorino et al., 1991) and glial cells ((Siao and Tsirka, 2002); (Buisson et al., 1998)). Unlike other serine proteases, tPA is an unusually active zymogen, with full intrinsic activity and low zymogenicity (Loscalzo, 1988). In the vasculature, tPA promotes fibrinolysis via the conversion of the abundant and inactive fibrin-bound zymogen plasminogen into plasmin. In the brain parenchyma, tPA was reported to display critical functions such as the control of the neuronal migration, learning and memory processes notably through the control of the N-methyl-D-aspartate receptor (NMDAR) signalling ((Calabresi et al., 2000); (Nicole et al., 2001); (Su et al., 2008); (Seeds et al., 1999)).

At the time when tPA (clinically delivered as Actilyse® or Alteplase®) was approved by the Federal Food and Drug Administration for the acute treatment of ischemic stroke, experimental data favour the idea that beyond its beneficial vascular effects, tPA may have damaging properties in the cerebral parenchyma, including haemorrhagic transformations and neurotoxicity ((Fugate et al., 2010); (Yepes et al., 2009)). Indeed, beyond its ability to promote clot lysis, it is now well established, from both experimental models and clinical data, that tPA can activate metalloproteinases, growth factors, mediates neutrophils activation and thus promotes haemorrhagic transformations ((Suzuki et al., 2009); (Fredriksson et al., 2004); (Rosell et al., 2008)). Interestingly, intravenous tPA is also capable to cross both the intact and the injured blood brain barrier ((Harada et al., 2005); (Benchenane et al., 2005); (Benchenane et al., 2005)) and thus influence brain dysfunctions such as neurotoxicity ((Samson and Medcalf, 2006); (Benchenane et al., 2007); for review, (Yepes et al., 2009)).

Accordingly, in the NVU and together with endogenous parenchymal tPA, blood derived tPA interacts with several substrates in vitro and in vivo. Among its mechanisms of action, by interacting with the N-methyl-D-aspartate receptors (NMDAR) in neurons tPA is known to activate NMDAR-dependent signaling processes leading to an exacerbated neuronal death in conditions of oxygen and glucose deprivation, excitotoxicity or ischemia (Nicole et al., 2001) (Baron et al., 2010).

It is thus of major concern to identify tPA derivatives which would present a good or improved fibrinolytic activity, but without having the damaging properties in the cerebral parenchyma of the existing tPA, including exacerbated neuronal death.

It is also of major concern that said tPA derivatives have a reasonable intrinsic activity (which may be measured thanks to their amidolytic activity), so that vascular adverse effects are minimized.

The inventors have identified specific mutated tPA, which are efficient thrombolytics, which have a reasonable intrinsic activity, and which do not promote NMDAR-mediated neurotoxicity.

SUMMARY OF THE INVENTION

The present invention relates to specific mutated tPA, which have a thrombolytic and fibrinolytic activity and are thus efficient for treating thrombotic neurological disorders and central retinal artery occlusion, most preferably stroke, but which do not show the neurotoxic adverse events.

Consequently, one object of the invention is a protein chosen from the group consisting of:
i) proteins comprising the sequence SEQ ID NO: 2 or SEQ ID NO:25, preferably consisting of SEQ ID NO: 2 or of the association of SEQ ID NO:25 and SEQ ID NO:26, wherein said sequence comprises:
a mutation A' consisting of the replacement of any amino acid of the Lysine Binding Site of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, preferably by arginine, or
a mutation B consisting of the replacement of arginine in position 275 of SEQ ID NO: 2 or SEQ ID NO:25 by serine, or
a double mutation A' and B consisting of the replacement of any amino acid of the Lysine Binding Site of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, preferably by arginine, and the replacement of arginine in position 275 of SEQ ID NO: 2 or SEQ ID NO:25 by serine,
ii) proteins comprising a sequence having at least 80% homology with SEQ ID NO: 2 or SEQ ID NO:25, said proteins comprising mutation A', mutation B, or mutation A' and B, and
iii) proteins consisting of a fragment of SEQ ID NO:2, said fragment consisting of the Kringle 2 domain and the catalytic domain, said proteins comprising mutation A', mutation B, or mutation A' and B.

Preferably, the protein of the invention is chosen from the group consisting of:
i) proteins comprising the sequence SEQ ID NO: 2 or SEQ ID NO:25, preferably consisting of SEQ ID NO: 2 or of the association of SEQ ID NO:25 and SEQ ID NO:26, wherein said sequence comprises:
a mutation A consisting of the replacement of tryptophan in position 253 of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, preferably by arginine, or
a mutation B consisting of the replacement of arginine in position 275 of SEQ ID NO: 2 or SEQ ID NO:25 by serine, or
a double mutation A and B consisting of the replacement of tryptophan in position 253 of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, preferably by arginine, and the replacement of arginine in position 275 of SEQ ID NO: 2 or SEQ ID NO:25 by serine, ii) proteins comprising a sequence having at least 80% homology with SEQ ID NO: 2 or SEQ ID NO:25, said proteins comprising mutation A, mutation B, or mutation A and B, and iii) proteins consisting of a fragment of SEQ ID NO:2, said fragment consisting of the Kringle 2 domain and the catalytic domain, said proteins comprising mutation A, mutation B, or mutation A and B.

Another object of the invention is a polynucleotide encoding for said protein.

Another object of the invention is an expression vector comprising said polynucleotide.

Another object of the invention is a host cell comprising said expression vector or said polynucleotide.

Another object of the invention is the use of said protein as a medicament. Particularly, said protein may be used for treating thrombotic diseases, and preferably for treating intra-cerebral haemorrhages or ocular haemorrhages, more preferably for treating stroke or central retinal artery occlusion.

Another object of the invention is a method for treating a thrombotic disease in a subject in need thereof, particularly stroke or central retinal artery occlusion, comprising administering a therapeutically effective amount of a protein according to the invention to said subject.

DETAILED DESCRIPTION OF THE INVENTION

Definitions

As used herein, the terms "protein" and "polypeptide" are used herein interchangeably, and refer to an amino acid sequence having more than 500 amino acids. As used herein, the term "protein" encompasses amino acid sequences having between 500 and 1000 amino acids, preferably between 510 and 900 amino acids, preferably between 520 and 800 amino acids, preferably between 525 and 700 amino acids.

The term "homology" (or "homologous"), as used herein, is synonymous with the term "identity" and refers to the sequence similarity between two polypeptide molecules or between two nucleic acid molecule. When a position in both compared sequences is occupied by the same base or same amino acid residue, then the respective molecules are homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid sequences. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g., that have a similar size, shape, electric charge, chemical properties, including the ability to form covalent or hydrogen bonds, or the like. Particularly preferred conservative substitutions are those fulfilling the criteria defined for an "accepted point mutation" by Dayhoff et al. ("Atlas of Protein Sequence and Structure", 1978, Nat. Biomed. Res. Foundation, Washington, D.C., Suppl. 3, 22: 354-352).

The homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, CLUSTALW, etc. Thus, according to the invention, a sequence having at least 80% homology with SEQ ID NO: 2 is a sequence for which the number of matching or homologous positions shared by said sequence and SEQ ID NO:2, divided by the length of SEQ ID NO:2 and multiplied by 100, is at least equal to 80.

The term "thrombotic diseases" as used herein encompasses deep vein thrombosis (DVT), pulmonary embolism (PE), coronary artery disease (CAD) and acute coronary syndrome (ACS), central retinal artery occlusion (CRAO), age related macular degeneration (AMD) and thrombotic neurological disorders, including stroke.

The term "thrombotic neurological disorder" as used herein is defined as a disease, disorder or condition which directly or indirectly affects the normal functioning or anatomy of a subject's nervous system and includes, but is not limited to, cerebrovascular insufficiency, cerebral ischemia, cerebral or cerebral infarction such as stroke, retinal ischemia (diabetic or otherwise), glaucoma, retinal degeneration, multiple sclerosis, ischemic optic neuropathy, reperfusion following acute cerebral ischemia, perinatal hypoxic-ischemic injury, or intracranial haemorrhage of any type (including, but not limited to, epidural, subdural, subarachnoid or intracerebral haemorrhage).

The term "fibrinolytic activity" or "thrombolytic activity" refers to the capacity to break down a fibrin clot.

The term "treating" a disorder or a condition refers to reversing, alleviating or inhibiting the process of one or more symptoms of such disorder or condition.

As used herein, the term "subject" denotes a mammal, such as a rodent, a feline, a canine, a pig, a bovine and a primate. Preferably a subject according to the invention is a human.

A "therapeutically effective amount" as used herein is intended for a minimal amount of active agent which is necessary to impart therapeutic benefit to a subject. For example, a "therapeutically effective amount of the active agent" to a subject is an amount of the active agent that induces, ameliorates or causes an improvement in the pathological symptoms, disease progression, or physical conditions associated with the disease affecting the subject.

The Invention

The present invention relates to a protein chosen from the group consisting of:

i) proteins comprising the sequence SEQ ID NO: 2 or SEQ ID NO:25, preferably consisting of SEQ ID NO: 2 or of the association of SEQ ID NO:25 and SEQ ID NO:26, wherein said sequence comprises:

a mutation A' consisting of the replacement of any amino acid of the Lysine Binding Site of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, preferably by arginine, or a mutation B consisting of the replacement of arginine in position 275 of SEQ ID NO: 2 or SEQ ID NO:25 by serine, or a double mutation A' and B consisting of the replacement of any amino acid of the Lysine Binding Site of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, preferably by arginine, and the replacement of arginine in position 275 of SEQ ID NO: 2 or SEQ ID NO:25 by serine, ii) proteins comprising a sequence having at least 80% homology with SEQ ID NO: 2 or SEQ ID NO:25, said proteins comprising mutation A', mutation B, or mutation A' and B, and iii) proteins consisting of a fragment of SEQ ID NO:2, said fragment consisting of the Kringle 2 domain and the catalytic domain, said proteins comprising mutation A', mutation B, or mutation A' and B.

The amino acids of the Lysine Binding Site concerned by mutation A' are easy to identify: if one amino acid of said Lysine Binding Site is mutated, then the corresponding mutant does not induce a significant effect in the NMDA neurotoxicity test, as explained in example 1 below (see protocol for "Excitotoxic neuronal death.").

The amino acids of the Lysine Binding Site which may be mutated according to mutation A' are preferably the charged amino acids (positively and negatively) and the hydrophobic amino acids of the Lysine Binding Site. Preferably said amino acids are the aspartic acids in position 236 and 238, and tryptophan in position 253 of SEQ ID NO:2 or SEQ ID NO:25.

Preferably, mutation A' is mutation A consisting of the replacement of tryptophan in position 253 of SEQ ID NO: 2 or SEQ ID NO:25 by a hydrophilic amino acid chosen from arginine, aspartic acid, glutamic acid, lysine, asparagine, glutamine, serine, threonine, tyrosine and histidine.

Preferably, the double mutation A' and B is double mutation A and B consisting of the replacement of tryptophan in position 253 of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, and the replacement of arginine in position 275 of SEQ ID NO: 2 or SEQ ID NO:25 by serine.

Preferably, the protein of the invention is chosen from the group consisting of:

i) proteins comprising the sequence SEQ ID NO: 2 or SEQ ID NO:25, preferably consisting of SEQ ID NO: 2 or of the association of SEQ ID NO:25 and SEQ ID NO:26, wherein said sequence comprises:

a mutation A consisting of the replacement of tryptophan in position 253 of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, or a mutation B consisting of the replacement of arginine in position 275 of SEQ ID NO: 2 or SEQ ID NO:25 by serine, or a double mutation A and B consisting of the replacement of tryptophan in position 253 of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, and the replacement of arginine in position 275 of SEQ ID NO: 2 or SEQ ID NO:25 by serine, ii) proteins comprising a sequence having at least 80% homology with SEQ ID NO: 2 or SEQ ID NO:25, said proteins comprising mutation A, mutation B, or mutation A and B, and iii) proteins consisting of a fragment of SEQ ID NO:2, said fragment consisting of the Kringle 2 domain and the catalytic domain, said proteins comprising mutation A, mutation B, or mutation A and B.

Preferably, said mutation A consists of the replacement of tryptophan in position 253 of SEQ ID NO: 2 or SEQ ID NO:25 by arginine. Preferably, said mutation A and B consists of the replacement of tryptophan in position 253 of SEQ ID NO: 2 or SEQ ID NO:25 by arginine, and of the replacement of arginine in position 275 of SEQ ID NO: 2 or SEQ ID NO:25 by serine.

Preferably, the protein according to the invention comprises mutation A' or mutation A' and B, preferably mutation A or mutation A and B.

Said protein according to the invention is a mutated tPA, which has a good fibrinolytic activity and which does not promote N-methyl-D-aspartate receptors (NMDAR) mediated neurotoxicity. This is notably shown in the example below.

tPA is encoded by the PLAT gene and refers to the serine protease EC 3.4.21.68. Human tPA is commercially available as Alteplase (Activase® or Actilyse®). tPA is composed of 5 domains: a Finger domain in the N-terminus, then an EGF-like domain, a Kringle 1 and a Kringle 2 domains, and finally the catalytic domain in the C-terminus. The Kringle 2 domain comprises a Lysine Binding Site (LBS). The tPA protein is well conserved among mammals: human, pig, bovine, mouse and rat tPA share at least 80% homology. Particularly, human and rat tPA share 81% homology.

Human tPA can be found in UniProtKB under the accession number P00750, and rat tPA can be found in UniProtKB under the accession number P19637. Human tPA is present under 4 isoforms: isoform 1 is the canonical sequence, whereas isoforms 2 to 4 differ from this canonical sequence by deletions and substitutions.

The protein is modified during processing: mammalian tPA is translated in a prepropeptide form, and then processed into the mature protein. The mature protein is finally cleaved into two chains, so as to give a two-chain form, wherein both chains are linked together via a disulfide bond.

For example, human tPA is first translated in a prepropeptide form comprising 562 amino acids, and then processed into the mature protein comprising 527 amino acids (the 35 first amino acids are cleaved during processing). Finally, after cleavage of the mature protein, the human two-chain form comprises a first chain of 275 amino acids, and a second chain of 252 amino acids.

The prepropeptide of human tPA corresponds to SEQ ID NO:1 in the present invention, whereas its mature protein corresponds to SEQ ID NO:2. Finally, the first chain of the human two-chain form corresponds to SEQ ID NO:25, and the second chain of the human two-chain form corresponds to SEQ ID NO:26. SEQ ID NO:25 is identical to the first 275 amino acids of SEQ ID NO:2. SEQ ID NO:26 is identical to the last 252 amino acids of SEQ ID NO:2.

As another example, rat tPA is first translated in a prepropeptide form comprising 559 amino acids, and then processed into the mature protein comprising 527 amino acids (the 32 first amino acids are cleaved during processing).

Without being bound by any theory, the inventors have shown in the example that tPA specifically mutated in the Lysine Binding Site present in the Kringle 2 domain (i.e. like SEQ ID NO:4 or SEQ ID NO:3)—and particularly in a LBS constitutive tryptophan—do not induce neurotoxicity. Nevertheless, said mutations do not decrease the thrombolytic competence of said mutated tPA, the Kringle 2 domain having a minor function in fibrinolytic activity (Bakker et al, 1995; Bennett et al, 1991).

Moreover, tPA mutants according to the invention comprising at least mutation B are more stable than their wild type version.

The proteins according to the invention comprise mutated tPA proteins, in their original mature or cleaved form. Therefore, the proteins according to the invention comprise single-chain tPA (sc-tPA) mutated with mutation A, mutation B or mutation A and B. sc-tPA has its general meaning in the art and refers to the mature protein of tPA.

The proteins according to the invention also comprise two-chain tPA (tc-tPA) mutated with mutation A, mutation B or mutation A and B. tc-tPA has its general meaning in the art and refers to the cleaved form of tPA, obtained after cleavage of sc-tPA mature protein by a proteolytic cleavage at Arg-Ile, for example at Arg275-Ile276 in human. Both chains of tc-tPA are linked together by a disulfide bond.

It has to be noted that, because of mutation B according to the invention, sc* mutant cannot be converted into tc-tPA form by its usual activators (for example plasmin or kallikrein), but only in sc-tPA form.

The protein according to the invention may be chosen from group i), i.e. proteins comprising the sequence SEQ ID NO: 2 or SEQ ID NO:25, preferably consisting of SEQ ID NO: 2 or of the association of SEQ ID NO:25 and SEQ ID NO:26, wherein said sequence comprises:
a mutation A consisting of the replacement of tryptophan in position 253 of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, preferably arginine, or
a mutation B consisting of the replacement of arginine in position 275 of SEQ ID NO: 2 or SEQ ID NO:25 by serine, or
a double mutation A and B consisting of the replacement of tryptophan in position 253 of SEQ ID NO: 2 or SEQ ID NO:25 by a hydrophilic amino acid chosen from arginine, aspartic acid, glutamic acid, lysine, asparagine, glutamine, serine, threonine, tyrosine and histidine, preferably arginine, and the replacement of arginine in position 275 of SEQ ID NO: 2 or SEQ ID NO:25 by serine.

Said group i) corresponds to sequences comprising SEQ ID NO:2, said SEQ ID NO:2 being specifically mutated with mutation A', mutation B or mutation A' and B (preferably with mutation A, mutation B or mutation A and B), and also to sequences comprising SEQ ID NO:25, said SEQ ID NO:25 being specifically mutated with mutation A', mutation B or mutation A' and B (preferably with mutation A, mutation B or mutation A and B).

Mutation A according to the invention is the following replacement: tryptophan in position 253 is replaced by a hydrophilic amino acid chosen from arginine, aspartic acid, glutamic acid, lysine, asparagine, glutamine, serine, threonine, tyrosine and histidine, preferably arginine. Thus, preferably, mutation A is the following replacement: W253R (in the present application, this nomenclature successively indicates: the amino acid which is replaced, its position in SEQ ID NO:2 or SEQ ID NO:25, and the amino acid which is introduced). Mutation B according to the invention is the following replacement: R275S.

Mutation A and B according to the invention is the double mutation W253 (hydrophilic amino acid chosen from arginine, aspartic acid, glutamic acid, lysine, asparagine, glutamine, serine, threonine, tyrosine and histidine, preferably arginine) and R275S.

Preferably, mutation A and B according to the invention is the double mutation W253R and R275 S.

Preferably, group i) corresponds to sequences consisting of SEQ ID NO:2, said SEQ ID NO:2 being specifically mutated with mutation A, mutation B or mutation A and B, and also to sequences consisting of the association of SEQ ID NO:25 and SEQ ID NO:26, said SEQ ID NO:25 being specifically mutated with mutation A, mutation B or mutation A and B.

The expression "association of" SEQ ID NO:25 and SEQ ID NO:26 means that both sequences are linked together via a disulfide bond. It corresponds to the tc-tPA form.

Preferably, proteins according to group i) are SEQ ID NO:5, SEQ ID NO:6, SEQ ID NO:9, SEQ ID NO:10, SEQ ID NO:13 and SEQ ID NO:14.

The protein according to the invention may also be chosen from group ii), i.e. proteins comprising a sequence having at least 80% homology with (the whole sequence) SEQ ID NO: 2 or SEQ ID NO:25, said proteins comprising mutation A', mutation B, or mutation A' and B (preferably mutation A, mutation B or mutation A and B). Proteins according to group ii) comprise a sequence having at least 80% homology with SEQ ID NO:2 over its whole length, and said proteins comprise mutation A', mutation B, or mutation A' and B (preferably mutation A, mutation B or mutation A and B). Proteins according to group ii) also comprise a sequence having at least 80% homology with SEQ ID NO:25 over its whole length, and said proteins comprise mutation A', mutation B, or mutation A' and B (preferably mutation A, mutation B or mutation A and B); in this case, said homologous protein may be linked to a protein consisting of SEQ ID NO:26 via a disulfide bond.

Said group ii) corresponds to amino acid sequences having at least 80% homology with SEQ ID NO:2 or SEQ ID NO:25, said SEQ ID NO:2 or SEQ ID NO:25 being specifically mutated with mutation A', mutation B or mutation A' and B (preferably with mutation A, mutation B or mutation A and B). Preferably, proteins of group ii) have at least 81%, preferably at least 85%, preferably at least 90%, preferably at least 95%, and preferably at least 99% homology with SEQ ID NO: 2 or SEQ ID NO:25, said proteins comprising mutation A', mutation B, or mutation A' and B (preferably mutation A, mutation B or mutation A and B).

Provided that they comprise mutation A', mutation B, or mutation A' and B, proteins of group ii) may comprise at least one of the following modifications:
the replacement of proline in position 125 of SEQ ID NO:2 or SEQ ID NO:25 by arginine,
the deletion of the Finger domain in the N-terminus and/or the deletion of the EGF-like domain, in SEQ ID NO:2 or SEQ ID NO:25, and/or the replacement of asparagine in position 117 of SEQ ID NO:2 or SEQ ID NO:25 by glutamine,
the replacement of threonine in position 103 of SEQ ID NO:2 or SEQ ID NO:25 by asparagine, and/or the replacement of asparagine in position 117 of SEQ ID NO:2 or SEQ ID NO:25 by glutamine, and/or the replacement of lysine-histidine-arginine-arginine (KHRR; SEQ ID NO:45) in positions 296 to 299 of SEQ ID NO:2 by alanine-alanine-alanine-alanine (AAAA; SEQ ID NO:46),
the replacement of cysteine in position 84 of SEQ ID NO:2 or SEQ ID NO:25 by serine,
the replacement of arginine in position 275 of SEQ ID NO:2 or SEQ ID NO:25 by glutamic acid or glycine, said protein comprising mutation A only, and/or the deletion of the Kringle 1 domain in SEQ ID NO:2 or SEQ ID NO:25.

Provided that it comprises mutation A', mutation B, or mutation A' and B, the protein according to the invention may be chosen from group iii), i.e. proteins consisting of a fragment of SEQ ID NO:2, said fragment consisting of the Kringle 2 domain and the catalytic domain. Said fragment of SEQ ID NO:2 consisting of the Kringle 2 domain and the catalytic domain is thus devoided of the Finger domain, the EGF-like domain and the Kringle 1 domain. Preferably, said fragment of SEQ ID NO:2 consists of amino acids 180 to 526 of SEQ ID NO:2. Thus, said group iii) preferably corresponds to the sequence of amino acids 180 to 526 of SEQ ID NO:2, said sequence comprising mutation A', mutation B or mutation A' and B (preferably mutation A, mutation B or mutation A and B).

Preferably, proteins of group ii) or iii) come from human, rat, mouse, pig or bovine.

Preferably, proteins according to group ii) are SEQ ID NO:3, SEQ ID NO:4, SEQ ID NO:7, SEQ ID NO:8, SEQ ID NO:11 and SEQ ID NO:12.

Preferably, the protein according to the invention is chosen from the group consisting of proteins comprising at least one of the sequences SEQ ID NO: 3 to SEQ ID NO: 14. More preferably, the protein according to the invention is selected in the group consisting of sequences SEQ ID NO: 3 to SEQ ID NO: 14; in other words, said protein consists in one of the sequences SEQ ID NO: 3 to SEQ ID NO: 14.

Another object of the invention is a polynucleotide encoding for said protein. In view of the amino acid sequence of said protein, the corresponding polynucleotide can be synthetized. Preferably, said polynucleotide derived from sequences SEQ ID NO:15 or SEQ ID NO:16.

The described sequences in the present patent application can be summarized as follows:

| Sequence (SEQ ID NO) | Corresponding protein or nucleic acid |
| --- | --- |
| 1 | Human wt tPA prepropeptide form |
| 2 | Human wt tPA mature form |
| 3 | Rat mutated K2* prepropeptide form |
| 4 | Rat mutated K2* mature form |
| 5 | Human mutated K2* prepropeptide form |
| 6 | Human mutated K2* mature form |
| 7 | Rat mutated sc* prepropeptide form |
| 8 | Rat mutated sc* mature form |
| 9 | Human mutated sc* prepropeptide form |
| 10 | Human mutated sc* mature form |
| 11 | Rat mutated K2*/sc* prepropeptide form |
| 12 | Rat mutated K2*/sc* mature form |
| 13 | Human mutated K2*/sc* prepropeptide form |
| 14 | Human mutated K2*/sc* mature form |
| 15 | Rat wt tPA prepropeptide form nucleic acid |
| 16 | Rat wt tPA mature form nucleic acid |
| 17 to 24 | Nucleic acid primers |
| 25 | Human wt tPA first chain of tc-tPA |
| 26 | Human wt tPA second chain of tc-tPA |
| 27 | Human wt tPA mature form with a 6xHis tag at the N-terminal position, followed by a linker between the his-tag and the tPA sequence |
| 28 | Human mutated K2* tPA mature form with a 6xHis tag at the N-terminal position, followed by a linker between the his-tag and the tPA sequence (hutPA K2*) |
| 29 | Human mutated sc* tPA mature form with a 6xHis tag at the N-terminal position, followed by a linker between the his-tag and the tPA sequence (hutPA sc*) |
| 30 | Human tPA double mutant form with a 6xHis tag at the N-terminal position, followed by a linker between the his-tag and the tPA sequence (Opt-PA) |
| 31 | Human wt tPA P125R W253R R275S mutant form with a 6xHis tag at the N-terminal position, followed by a linker between the his-tag and the tPA sequence (Opt-PA2) |

Another object of the invention is an expression vector comprising said polynucleotide encoding for said protein. According to the invention, expression vectors suitable for use in the invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, cytomegalovirus, retrovirus, lentivirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods or commercially available.

Another object of the invention is a host cell comprising an expression vector as described here above, or a polynucleotide as described above. According to the invention, examples of host cells that may be used are eukaryote cells, such as animal, plant, insect and yeast cells and prokaryotes cells, such as E. coli. The means by which the vector carrying the gene may be introduced into the cells include, but are not limited to, microinjection, electroporation, transduction, or transfection using DEAE-dextran, lipofection, calcium phosphate or other procedures known to one skilled in the art.

In a preferred embodiment, eukaryotic expression vectors that function in eukaryotic cells are used. Examples of such vectors include, but are not limited to, viral vectors such as retrovirus, adenovirus, adeno-associated virus, herpes virus, vaccinia virus, poxvirus, poliovirus; lentivirus, bacterial expression vectors, plasmids, such as pcDNA5 or the baculovirus transfer vectors. Preferred eukaryotic cell lines include, but are not limited to, COS cells, CHO cells, HeLa cells, NIH/3T3 cells, 293 cells (ATCC #CRL1573), T2 cells, dendritic cells, or monocytes.

The protein according to the invention may be used as a medicament. Therefore, the protein according to the invention may be introduced in a pharmaceutical composition.

Particularly, the protein according to the invention may be used for treating thrombotic diseases. Said thrombotic diseases include ischemia, artery or vein occlusions (like central retinal artery occlusion), intra-cerebral haemorrhages and ocular haemorrhages. Intra-cerebral haemorrhages include stroke, intra-parenchymatous haemorrhages, intra-ventricular haemorrhages and subarachnoid haemorrhages. The intra-cerebral hematomas (or intraparenchymal) are a type of stroke, and are characterized by a spontaneous eruption of blood within the brain parenchyma and the cause is not traumatic.

Ocular haemorrhages include macular haemorrhages, linked to ocular diseases such as age-related macular degeneration (AMD), and vitreous haemorrhages.

Particularly, the protein according to the invention may be used for treating thrombotic diseases, preferably chosen from deep vein thrombosis (DVT), pulmonary embolism (PE), coronary artery disease (CAD), acute coronary syndrome (ACS), retinal occlusion, which can be central or not, artery or venous, preferably central retinal artery occlusion (CRAO), age related macular degeneration (AMD), cerebrovascular insufficiency, cerebral ischemia, cerebral infarction such as stroke, retinal ischemia, glaucoma, retinal degeneration, multiple sclerosis, ischemic optic neuropathy, reperfusion following acute cerebral ischemia, perinatal hypoxic-ischemic injury and intracranial haemorrhage of any type. Preferably, the protein according to the invention is used for treating intra-cerebral haemorrhages or ocular haemorrhages, more preferably for treating stroke or central retinal artery occlusion.

The pharmaceutical composition of the invention may be combined with pharmaceutically acceptable excipients, and optionally sustained-release matrices, such as biodegradable polymers, to form a therapeutic composition.

In the pharmaceutical composition of the present invention for oral, sublingual, subcutaneous, intramuscular, intravenous, intraarterial, intrathecal, intra-ocular, intra-cerebral, transdermal, local or rectal administration, the active principle, alone or in combination with another active principle, can be administered in a unit administration form, as a mixture with conventional pharmaceutical supports, to animals and human beings. Preferably, the pharmaceutical composition of the present invention is administered via the intra-ocular or intra-cerebral route.

The intra-ocular route includes intra-vitreous administration (like an injection), and the orbital floor route of administration.

Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical composition contains vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Said solutions may comprise at least polyurethane.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical composition of the invention can be formulated into a composition in a neutral or salt form. Pharmaceutically acceptable salts include the acid addition salts (foinied with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active substances in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The pharmaceutical composition of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The following examples are given for the purpose of illustrating various embodiments of the invention.

BRIEF DESCRIPTION OF THE FIGURES

Important Note:

In the following figures which are related to the example, amino acids are numbered from the N-terminal serine of the mature *Rattus norvegicus* tPA sequence (UniProtKB: P19637).

FIG. 1A-B. Comparison table of three plasminogen activators. A) Human tPA, Rat tPA and *Desmodus rotundus* plasminogen activator (DSPA) exhibit an almost similar sequence of domains ranging from a finger domain at the amino terminal extremity to the protease domain at the carboxyl terminal extremity. The kringle 2 domain of tPA is absent in DSPA. Moreover human and rat tPA and DSPA share strong homologies (>80% between rat and human tPA; >65% between human tPA and DSPA). B) Map of the plasmid pcDNA5/FRT used in the experiments for the expression of rat wt tPA.

FIG. 2A-B. Primary structure comparison of human and rat tPA and DSPA. A) Sequence analysis of the kringle domain of DSPA reveals naturally occurring amino acid substitutions leading to a non-functional lysine-binding site: the anionic charges in position D237 and D239 (black box 1) and the hydrophobic amino acid W254 (black box 2) are missing (SEQ ID NOs: 40-42). B) DSPA (SEQ ID NO: 44) is a specific protease in that it exists only in a single-chain form whereas proteases such as human (SEQ ID NO: 27) or rat tPA (SEQ ID NO: 43) may be processed into a two-chain form.

($p<0.02$; *$p<0.01$).

Figure 5A:
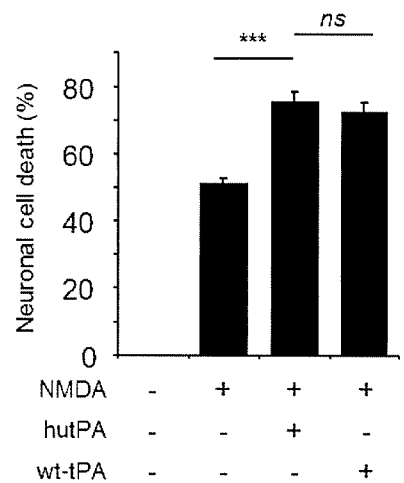
Figure 5B:
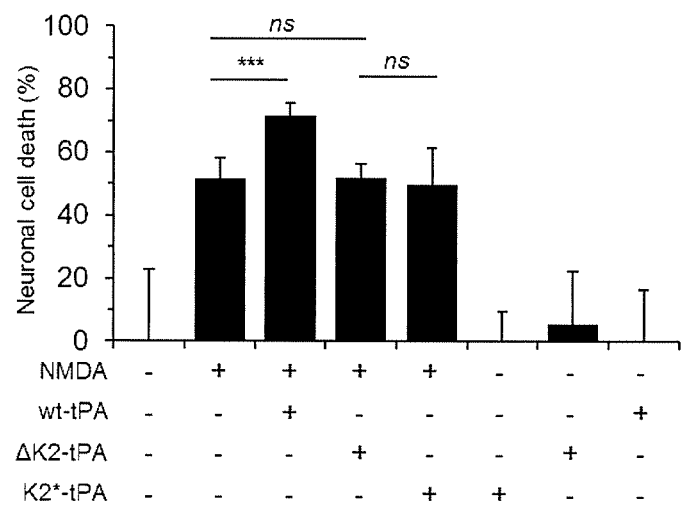
Figure 5C:
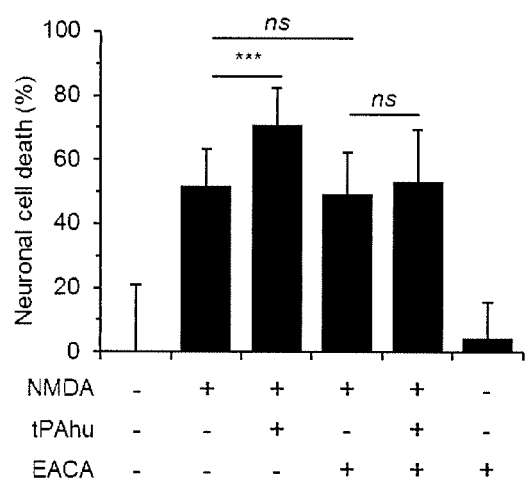

FIG. 5A-C. Invalidation of the constitutive lysine-binding site of the tPA kringle 2 domain abolishes tPA-mediated neurotoxicity. (A-C) Neuronal death was assessed by measuring LDH release in the bathing media 24 hours after an 1 hour exposure of primary cultured cortical neurons (14 days in vitro—DIV) to 50 µM NMDA alone or supplemented with either (A) human tPA or rat wt-tPA (0.3 µM; n=12, 3 independent experiments) (B) wt-tPA, ΔK2-tPA or K2*-tPA (0.3 µM; n=12, 4 independent experiments) or (C) human tPA in the presence or not of 0.1 mM of the lysine analogue ε-ACA (ε-amino caproic acid) (n=19, 5 independent experiments). Data are presented as the mean value±SD of neuronal death in percent relative to control.

(***$p<0.01$; ns: not significant).

Figure 6A:
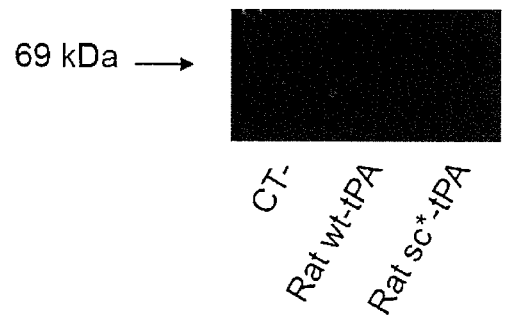
Figure 6B:
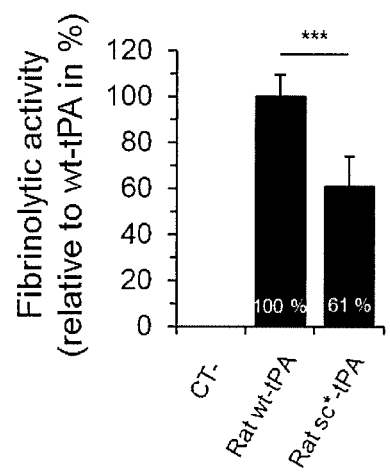

FIG. 6A-B. Fibrin partially restores plasminogen activation function of the inactive sc*-tPA. Whereas sc*-tPA is not able to promote alone the conversion of plasminogen into plasmin, its fibrin cofactor partially brings back its plasminogen activation function as detected (A) by fibrin agarose zymography following non reduced SDS PAGE electrophoresis and (B) in a platelet-poor plasma clot (PPP-clot) lysis assay. Fibrin clots restore the activity of sc*-tPA to a higher level than half the fibrinolytic activity of wt-tPA (n=3). Fibrinolytic activity was normalized to rat wt-tPA, using the half-time for clot lysis.

(***$p<0.01$).

Figure 7:
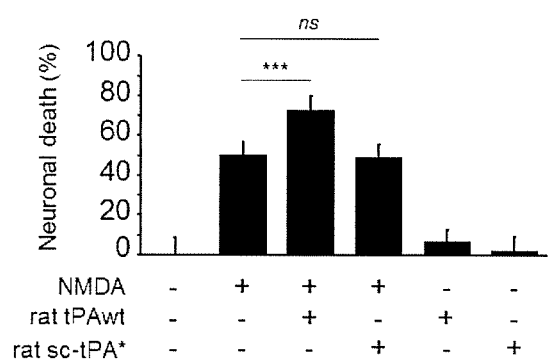

FIG. 7. Restoring sc-tPA zymogenicity rescues neurons from tPA potentiation of NMDA-mediated neurotoxicity. Neuronal death was assessed by measuring LDH release in the bathing media 24 hours after a 1 hour exposure of primary cultured cortical neurons (14 days in vitro—DIV) to 50 µM NMDA alone or supplemented with either rat wt-tPA or rat sc*-tPA (0.3 UM; n=12, 4 independent experiments).

Data are presented as the mean value±SD of neuronal death in percent relative to control.

(***p<0.01; ns: not significant).

Figure 8:
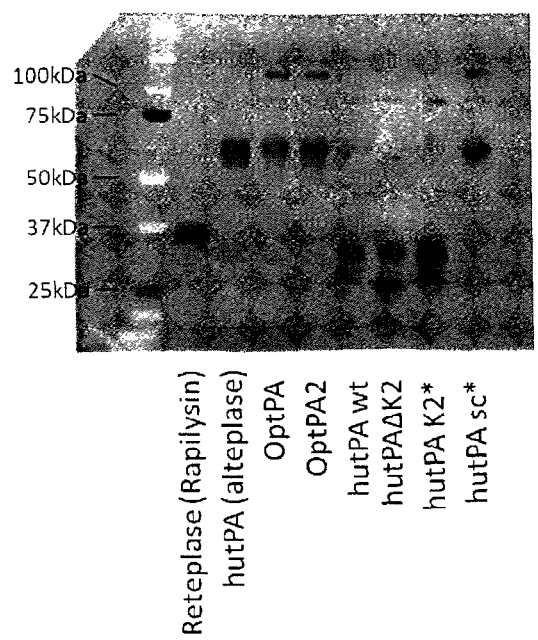

FIG. 8. Characterization of the human tPA variants. Equal amounts (200 ng) of the human tPA variants were subjected to immunoblotting and compared to the commercially available forms of tPA (actilyse) and reteplase (rapilysin).

Figure 9:
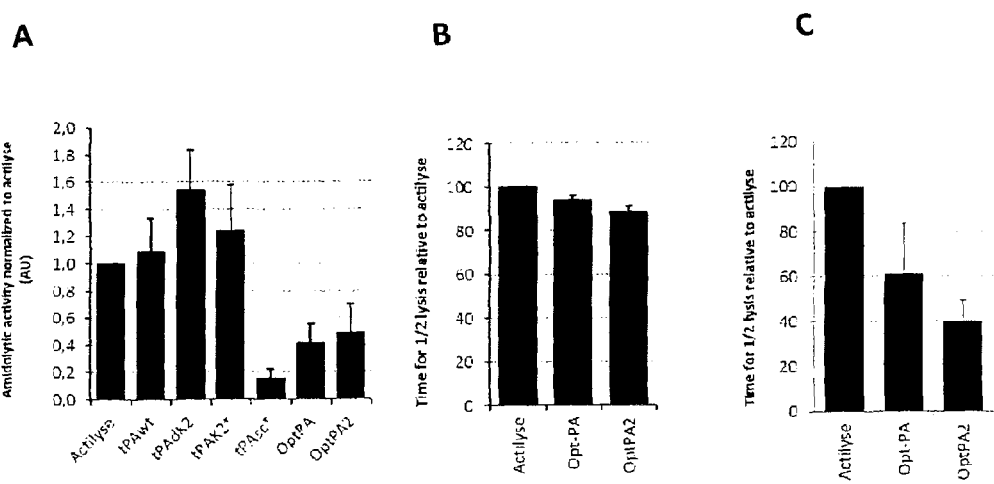

FIG. 9. Biochemical characterization of the tPA variants. A), intrinsic activity of the tPA variants determined by measuring the increase in absorbance of the free chromophore (AMC) generated, in comparison to the original substrate, per unit time at λ440 nm. The fluorogenic substrate used is Spectrofluor tPA (formula: $CH_3SO_2$-D-Phe-Gly-Arg-AMC.AcOH, American Diagnostica). Measurements were performed in duplicate using 5 different doses, in three independent experiments. B), Fibrinolytic activity of the double or triple tPA mutants normalized to the commercially available tPA (actilyse) using the half-time for clot lysis toward euglobulin-derived clots. C), Fibrinolytic activity of the double or triple tPA mutants normalized to the commercially available tPA (actilyse) using the half-time for clot lysis toward whole plasma-derived clots.

Figure 10:
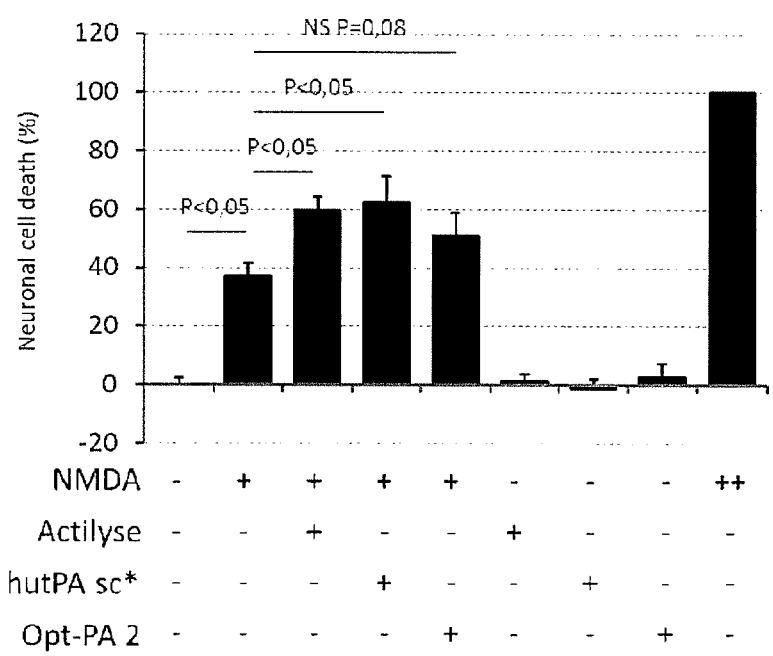

FIG. 10. In vitro proof of concept of the non-neurotoxic effect of the human tPA variants. Neuronal cell death was assessed by measuring lactate dehydrogenase release in the bathing media as described in the methods section. Human tPA (actilyse), hutPAsc* or Opt-PA2 (0.3 µM; 4 independent experiments) (for hutPAsc* and Opt-PA2 definitions, see table of the sequences above). Data are presented as the mean value±SD of neuronal death in percent relative to control; ns: not significant.

Figure 11:
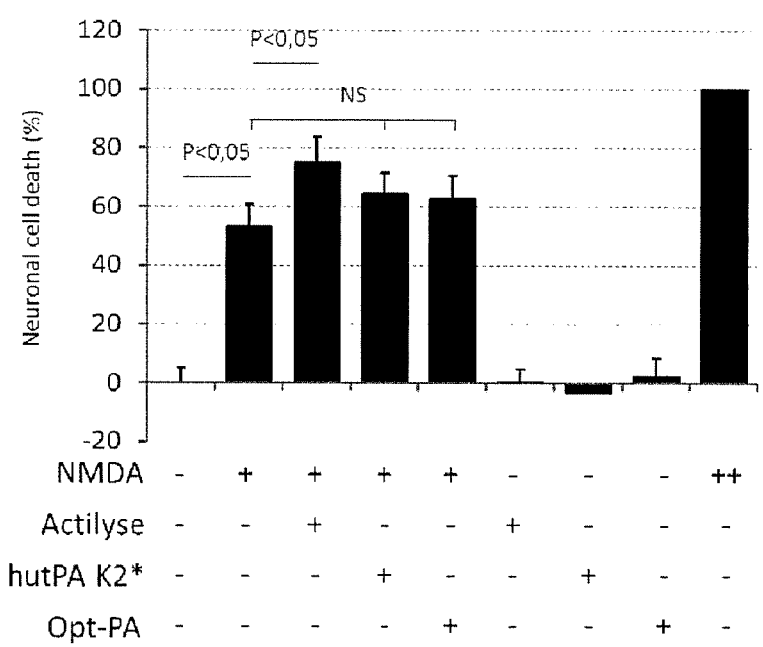

FIG. 11. In vitro proof of concept of the non-neurotoxic effect of the human tPA variants. Neuronal cell death was assessed by measuring lactate dehydrogenase release in the bathing media as described in the methods section. Human tPA (actilyse), hutPAK2* or Opt-PA (0.3 µM; 4 independent experiments) (for hutPAK2* and Opt-PA definitions, see table of the sequences above). Data are presented as the mean value±SD of neuronal death in percent relative to control; ns: not significant.

Figure 12:
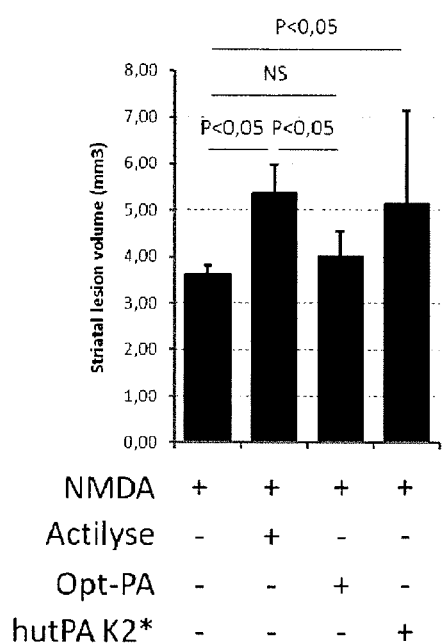

FIG. 12. Opt-PA does not promote NMDA-induced neurotoxicity in vivo. NMDA-induced excitotoxic brain lesions were measured by Magnetic Resonance Imaging (MRI) as described in the methods section, 24 hours after intrastriatal injection of NMDA (12.5 mM) alone or in combination with either actilyse (5 Opt-PA (5 µM), or hutPA K2* (5 µM) (for hutPAK2* and Opt-PA definitions, see table of the sequences above). Data are presented as the mean values±SD of lesion volumes in mm3.

FIG. 13. Summary of the tPA-related muteins produced in the study.

FIG. 14. Biochemical characteristics of the tPA variants. (1): sequence available in the UniProt Database, accession number P19637; (2): fibrinolytic activities obtained from euglobulin clot lysis time assay by reference to the International Reference Preparation (IRP 98/714) using the time to obtain 50% clot lysis; (3-4): Kd for fibrin (3) and Km and kcat for plasminogen in the presence of fibrin (4) obtained from 3 independent experiments (12 tested doses).

EXAMPLE 1: RAT TPA MUTANTS

Important Note:

In the following study, amino acids are numbered from the N-terminal serine of the mature *Rattus norvegicus* tPA sequence (UniProtKB: P19637).

Material and Methods

Chemicals.

N-methyl-D-aspartate (NMDA) was purchased from Tocris (Bristol, United Kingdom). Spectrofluor 444FL was purchased from American Diagnostica (Stamford, USA). 6-aminocaproic acid (E-ACA), Dulbecco's modified Eagle's medium (DMEM), poly-D-lysine, cytosine fl-D-arabinoside and hygromycin B were from Sigma-Aldrich (L'Isle d'Abeau, France). The QuickChange XL site-directed mutagenesis kit was from Stratagene (La Jolla, Calif., USA). Plasminogen was purchased from Calbiochem (Nottingham, United Kingdom). Lipofectamine 2000, Opti-MEM RSM, foetal bovine and horse sera, laminin were from Invitrogen (Cergy Pontoise, France). tPA (Actilyse®) came from Boehringer-Ingleheim (Germany)

Construction of Wild-Type tPA and ΔK2-tPA Muteins in pcDNA5/FRT Vector.

The full-size rat wild-type tPA coding sequence was amplified by PCR using an upstream primer 5' CCGGGATCCTCCTACAGAGCGACC 3' (SEQ ID NO:17) and a downstream primer 5' GGCAAGCTTTTGCTTCATGTTGTCTTGAATCCAGTT 3' (SEQ ID NO:18). A 6×His tag was placed at the N-terminal position of the mature protein. Digested PCR products were then inserted into a pcDNA5/FRT vector (Invitrogen, Cergy-Pontoise, France). Fusion PCR was performed to obtain ΔK2-tPA from wt-tPA coding sequence using the same protocol with the following fusion primers: upstream 5' CAGGCCGCACGTGGAGTCCTGAGTTGGTCCCTTAGG 3' (SEQ ID NO:19) and downstream 5' TCCACCTGCGGCCTG 3' (SEQ ID NO:20). Final constructs were checked using an automated sequence analysis.

Site-Directed Mutagenesis.

Mutagenesis of full-length tPA wt (tPA W254R) has been performed by using QuikChange® XL Site-Directed Mutagenesis Kit purchased from Stratagene (Agilent Technologies, Massy, France) and the following primers 5' GGACCGAAAGCTGACACGGGAATATTGCGACATGTCC 3' (SEQ ID NO:21) and 5' GGACATGTCGCAATATTCCCGTGGTCAGCTTTCGGTCC 3' (SEQ ID NO:22). Non-cleavable tPA (tPA R276S) has been obtained using 5' TACAAACAGCCTCTGTTTCGAATTAAAGGAGGA 3' (SEQ ID NO:23) and 5' TCCTCCTTTAATTCGAAACAGAGGCTGTTTGTA 3' (SEQ ID NO:24) primers. Mutations have been confirmed using an automated sequence analysis.

Human Embryonic Kidney (HEK)-293 Cell Cultures and Stable Transfection.

Human embryonic kidney 293 cells already stable transfected with the pFRT/lacZeo vector (HEK-FlpIn, Invitrogen) were grown in RPMI-1640 medium supplemented with 10% fetal bovine serum and 2 mM glutamine. Cells at high confluence were transfected using lipofectamine 2000 reagent according to manufacturer protocol (Invitrogen) with a mixture containing the tPA-related plasmids and the plasmid helper pOG44. After 24 hours, cells were washed. 48 hours after transfection positive clones were isolated by hygromycine B selection. The quality of the transfection was assessed by RT-PCRq.

Conditioned Media-Containing the tPA-Related Muteins.

High confluency cells stable transfected with the different tPA-related plasmids were incubated for 24 hours in minimal medium composed of Opti-MEM RSM (Invitrogen) added of 2 mM glutamine et containing 10 IU/ml aprotinin and 200 µg/ml hygromycin B. Supernatant were harvested in 0.01% azide, 2 mM EDTA, 0.01% tween 20, centrifuged 15 minutes at 10.000 g and finally stored at −20° C.

Bioreactor Production of the tPA-Related Muteins.

To produce high level of muteins, stable transfected HEK cells were grown in a laboratory-scale bioreactor CELLine AD 1000. Two weeks after a 1×10$^6$ viable cells/ml inoculation, cell compartment is harvested twice a week during four months. Each harvested supernatant is controlled in terms of pH, turbidity, centrifuged 15 minutes at 10.000 g and stored at −20° C. prior to 6×his purification.

6×his Muteins Purification.

Purification was processed using nickel-nitrilotriacetic acid (Ni-NTA) metal-affinity chromatography matrice (Qiagen, Courtaboeuf, France) according to manufacturer protocol. Muteins were then conditioned in a NH$_4$HCO$_3$ 0.5 M buffer, quantified and stored.

tPA Immunoblotting.

Immunoblottings were performed using a monoclonal mouse antibody raised against a penta-histidine sequence (1/1000eme), followed by incubation with the appropriate biotinilated-conjugated secondary antibody. Signal was amplified using the Extravidine (Sigma) biotin-peroxydase conjugate (1/5000). Immunoblots were revealed with an enhanced chemoluminescence ECL Plus immunoblotting detection system (Perkin Elmer-NEN, Paris, France).

SDS-PAGE Plasminogen-Casein Zymography.

Zymography assay was performed by addition of plasminogen (4.5 μg/ml) and casein (1%) in 10% SDS-polyacrylamide gels. Electrophoresis was performed at 4° C. Gels were washed with Triton X-100 (2.5%) and incubated for 2 hours at 37° C. Caseinolytic bands were visualized after Coomassie staining.

Amidolytic Activity Assay.

tPA-related muteins were incubated in the presence of a fluorogenic substrate (5 μM) (Spectrofluor® FL444). The reaction was carried out at 37° C. in 50 mM Tris (pH 8.0) containing 150 mM NaCl in a total volume of 100 μL. The amidolytic activity was measured as the change in fluorescence emission at 440 nm (excitation at 360 nm). Using Spectrozyme®, an amidolytic substrate (Spectrozyme tPA, SptPA)), wt-tPA and sc*-tPA (0.3 nM) were incubated with increasing concentrations of the SptPA (0-1 mM) in a microplate (200 μL per well) and OD405 nm recorded every minute using a microplate spectrophotometer (ELx 808, Biotek, USA). Then, the maximal velocity (Vmax) of the reaction was calculated and the data were plotted as follows:

$$\frac{1}{V} = f\left(\frac{1}{[SptPA]}\right) = \frac{Km}{V_m} \cdot \left(\frac{1}{[SptPA]}\right) + \frac{1}{V_m}.$$

Fibrin Agarose Zymography.

Proteins (10 μg) and reference proteins (10 μL of tPA 0.06 iu/mL, uPA 0.25 iu/mL and plasmin 200 nM) were electrophoresed in a 8% polyacrylamide gel under non-reducing conditions. SDS was then exchanged with 2.5% Triton X-100. After washing-off excess Triton X-100 with distilled water, the gel was carefully overlaid on a 1% agarose gel containing 1 mg/mL of bovine fibrinogen, 100 nM plasminogen and 0.2 NIH unit/mL of bovine thrombin. Zymograms were allowed to develop at 37° C. during 12 h and photographed at regular intervals using dark-ground illumination. Active proteins in cell lysates were identified by reference to the migration of known markers (uPA, tPA, plasmin). To verify the activator identity, zymograms were made on a fibrin-agarose gel containing a polyclonal antibody directed against tPA or a non immun IgG.

Clot Lysis Time.

Human plasma was collected and the euglobulin fractions, containing β- and γ-globulins were separated by dilution of one volume of chilled plasma in 20 volumes of chilled acetic acid 2.9 mM. After incubation at 4° C. for 15 minutes and centrifugation at 3000 g for 10 minutes, the euglobulin fraction was precipitated, the supernatant discarded and the precipitate dissolved in HEPES buffer (10 mM HEPES pH 7.4, 150 mM NaCl). The euglobulin solution (100 μL) was supplemented with 15 mM calcium chloride and 5, 10, 15, 20, 25 or 30 I.U. of the tPA muteins. The time to clot lysis was recorded by optical density (405 nm absorbance) at 37° C. Tests were performed in duplicate. Results are expressed as the time to 50% clot lysis.

Neuronal Cell Culture.

Neuronal cultures were prepared from foetal mice (embryonic day 15-16) as previously described (Nicole et al., 2001). Briefly cortices were dissected and dissociated in DMEM, and plated on 24-well plates previously coated with poly-D-Lysine (0.1 mg/mL) and laminin (0.02 mg/mL). Cells were cultured in DMEM supplemented with 5% fetal bovine serum, 5% horse serum and 2 mM glutamine. Cultures were maintained at 37° C. in a humidified 5% CO/atmosphere. Cytosine β-D-arabinoside (10 μM) was added after 3 days in vitro (DIV) to inhibit glial proliferation. Various treatments were performed after 14 DIV.

Excitotoxic Neuronal Death.

Excitotoxicity was induced by exposure of cortical neurons to NMDA (50 μM) in serum-free DMEM supplemented with 10 μM of glycine, for 1 hour. Recombinant human tPA and rat tPA-related muteins were applied with NMDA when indicated. Neuronal death was quantified 24 hours later by measuring the activity of lactate dehydrogenase (LDH) released from damaged cells into the bathing medium by using a cytotoxicity detection kit (Roche Diagnostics; Mannheim, Germany). The LDH level corresponding to the maximal neuronal death was determined in sister cultures exposed to 200 μM NMDA (LDH$_{max}$). Background LDH levels were determined in sister cultures subjected to control washes (LDH$_{min}$). Experimental values were measured after subtracting LDH$_{min}$ and then normalized to LDH$_{max}$−LDH$_{min}$ in order to express the results in percentage of neuronal death relative to control.

Kinetics of Plasminogen Activation in the Presence of Fibrin.

Kinetics of the activation of plasminogen on a fibrin surface were determined for each of the tPA mutants as previously describe by Angles-cano et al. Briefly, fibrinogen (0.3 μM) was immobilized on PVC plates previously activated by glutaraldehyde. Then, thrombin (10 NIH U/mL) was added for 2 h at 37° C. to convert fibrinogen into fibrin. The plates are then washed with 9 nM PPACK-containing binding buffer (50 mM PO$_4$ pH 6.8, 80 mM NaCl, 0.4% BSA, 0.01% Tween 20, 0.01% azide and 2 mM EDTA). tPA variants were then incubated on fibrin surfaces for 1 h at 37° C. with 50 pd., of binding buffer. Unbound proteins were eliminated by washing with a buffer (50 mM PO$_4$ pH 7.4, 80 mM NaCl, 0.2% BSA, 0.01% Tween 20, 0.01% azide) and the reaction started by adding 50 μL of assay buffer (50 mM PO$_4$ pH 7.4, 80 mM NaCl, 0.2% BSA) containing increasing amounts of plasminogen (0-500 nM) and a fixed concentration (0.75 mM) of the plasmin-selective chromogenic substrate (CBS0065, Diagnostica STAGO, Asnieres, France). The absorbance at 405 nm was recorded for 18 h using a spectrophotometer (ELx 808, Biotek, USA), and data were plotted as follows: ([Pn]=f(t)). The maximal velocity (M$_{Pn}$·s$^{-1}$) was measured for each activator concentration and was plotted against activator concentrations (Vi=f([Pg])). Kinetic parameters were determined by fitting data to the Lineweaver-Burk equation:

$$\frac{1}{Vi} = \frac{Km}{V_M}\left(\frac{1}{[Pg]}\right) + \frac{1}{V_M}$$

The kcat was calculated by using the following equation:

$$kcat = \frac{V_M}{[tPA]}$$

Statistical Analysis.

All the statistical analyses were performed by the two-tailed Kruskall-Wallis' test, followed by post-hoc comparisons, with the two-tailed Mann-Whitney's test. Results are expressed as mean±SD relative to control. Statistical significance is considered for p<0.05.

Results

Generation of New Thrombolytics Originated from tPA.

Figure 1B:
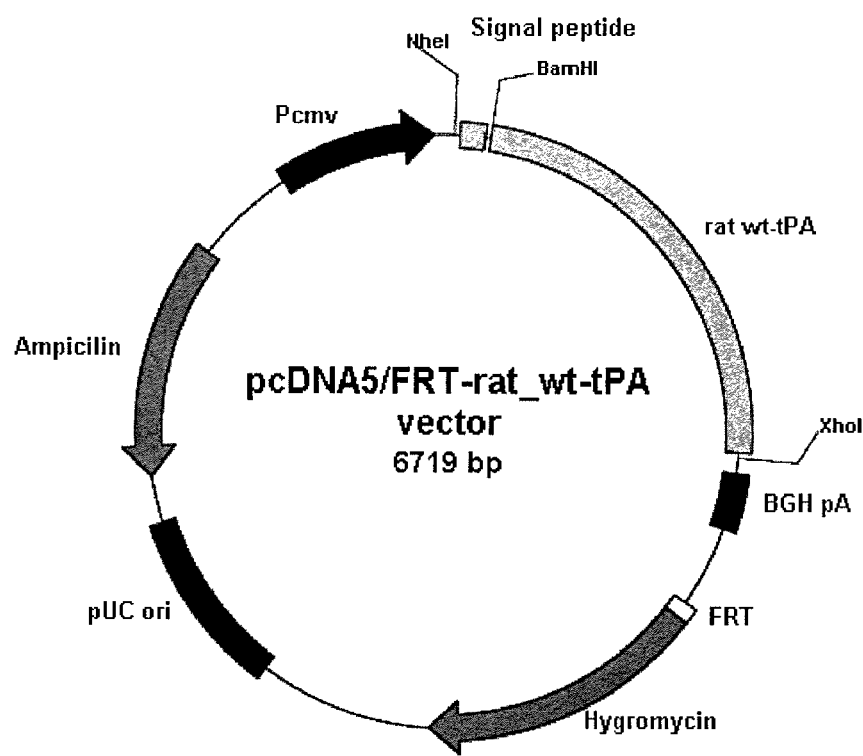

Structural differences between human tPA (UniProtKB: P00750), rat tPA (UniProtKB: P19637) and DSPAα1 (named DSPA) (UniProtKB: P98119) were studied using multiple alignments. Rat tPA shares 81% amino acids identity and 89% conserved substitutions with the human tPA (FIG. 1A). DSPA shares 67% amino acids identity and 79% conserved substitutions with the rat tPA. DSPA contains a single kringle domain having a high degree of amino acid sequence homology with the tPA's kringle 1 domain (FIG. 2A), including the absence of a constitutive lysine-binding site (FIG. 2A—black boxes). On the other hand the tPA's kringle 2 domain contains a constitutive lysine-binding site formed by the pair of aspartic acid in position 237 and 239 and the tryptophane in position 254. A second point of interest is that in contrast to tPA, DSPA is an exclusive single-chain serine protease (Schleuning et al., 1992). Indeed, analysis of the primary sequence of DSPA reveals the lack of the cleavage site present in tPA, Arg276-Iso277 (FIG. 2B). All these features of DSPA when compared to tPA are interestingly associated with an increased affinity for fibrin (Schleuning et al., 1992) and a lack of neurotoxicity (Liberatore et al., 2003).

Figure 3A:
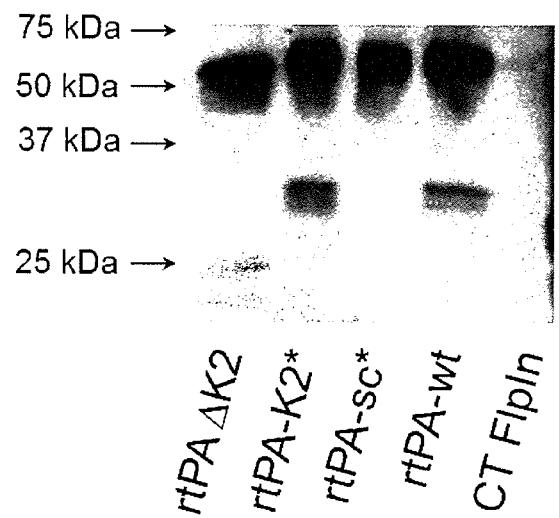
FIG. 3A-C. Biochemical characterization of the tPA-related muteins. A) Equal amounts (100 ng) of wt tPA, ΔK2-tPA, K2*-tPA and sc*-tPA muteins were subjected to immunoblotting. (B-C) Activity of the tPA-related muteins measured either on a fluorogenic substrate (B) or by plasminogen-casein zymography assays (C).
Figure 3B:
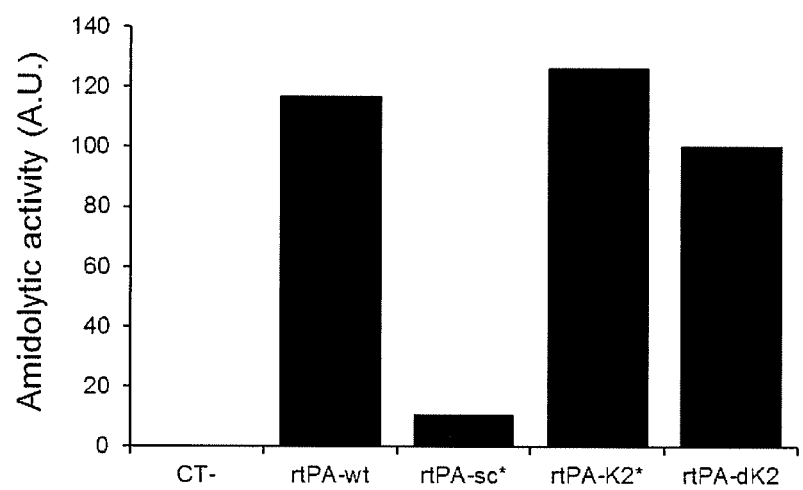
Figure 3C:
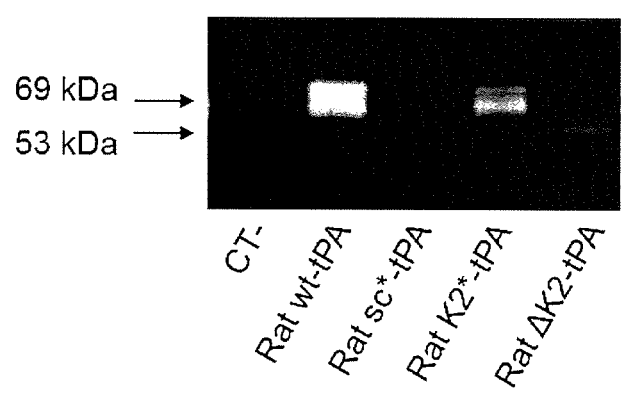

Thus, based on these observations, the inventors have designed and generated three muteins derived from the rat tPA (*Rattus norvegicus*) (rat wild type tPA named wt-tPA): (i) a rat tPA genetically engineered with complete deletion of its K2 domain (deletion of the amino acids 181 to 262), named ΔK2-tPA; (ii) a rat tPA containing a tryptophan to arginine point mutation at position 254 (W254R), named K2*-tPA; (iii) an exclusive rat single-chain tPA obtained by an arginine to serine point mutation at position 276 (R276S), named sc*-tPA (FIG. 13). After PCR-induced appropriate deletion/mutation as described above, the corresponding 6× histidine-tagged cDNAs were inserted into a mammalian expression vector pcDNA5/FRT (FRT: Flp Recombination Target) (FIG. 1B) and stable transfected in HEK-293 cells expressing the Flp-In system (Invitrogen) for stable production of the corresponding recombinant proteins, as described in the methods section. Once purified using nickel affinity chromatography, the muteins were subjected to SDS-PAGE electrophoresis and immunoblotting. wt-tPA, sc*-tPA and K2*-tPA displayed similar molecular weights, whereas the K2 deleted tPA, ΔK2-tPA, showed a 15 kDa reduced molecular weight (FIG. 3A). Interestingly, sc*-tPA is present under its exclusive single-chain form whereas wt-tPA, K2*-tPA and ΔK2-tPA present two-chain forms (at 35 kDa and 25 kDa for ΔK2-tPA). Thus the R276S point mutation (sc*-tPA) leads to the generation of a non-cleavable form of tPA Because tPA binds and cleaves several substrates beyond plasminogen, such as the PDGF-C or the NR1 subunit of the NMDAR with no identified allosteric regulator, the inventors have first evaluated the intrinsic proteolytic activity of each of these muteins. Thus, plasminogen-containing zymography assays (FIG. 3B) and amidolytic activity assays toward a fluorogenic substrate (Spectrofluor) (FIG. 3C) were performed for the different tPA-related muteins cited above. Our data reveal that although wt-tPA and kringle 2-related mutants (ΔK2-tPA and K2*-tPA) display amydolytic activity comparable to that observed for wt-tPA, sc*-tPA does not. Hereafter, muteins concentrations are normalised to their intrinsic proteolytic activity.

The inventors measured the ability of each of the tPA mutants to bind fibrin with Kd's of 0.26 nM, 1.2 nM, 0.5 nM and 0.82 nM for wt-tPA, sc*-tPA, K2*-tPA and ΔK2-tPA, respectively (FIG. 14).

tPA is known to bind and cleave several substrates beyond plasminogen (such as the GluN1 subunit) with no identified allosteric regulator. Therefore, the inventors evaluated the intrinsic proteolytic activity of each of the tPA variants. As such, amidolytic activity assays toward a fluorogenic substrate (Spectrofluor) and plasminogen-containing zymography assays were performed for the different tPA-related mutants cited above. The data reveal that, although wt-tPA and kringle 2-related mutants (ΔK2-tPA and K2*-tPA) display an amidolytic activity comparable to that observed for wt-tPA, sc*-tPA does not. To further investigate the behavior of the sc*-tPA variant when compared to the wt-tPA, the inventors determined the Km of both plasminogen activators by using the amidolytic Spectrozyme®, as the substrate. The data showed that, the point mutation within the cleavage site of tPA leads to a 3-fold increase of the Km value when compared to the wt-tPA (2.83E-04 and 9.12E-05 M, respectively). Hereafter, concentrations of the tPA mutants are normalised to their intrinsic amidolytic activity, unless otherwise mentioned.

Kringle 2-Related Muteins (ΔK2-tPA and K2*-tPA) Display a Higher Fibrinolytic Activity and Failed to Promote NMDA Receptors Mediated Neurotoxicity.

Figure 4A:
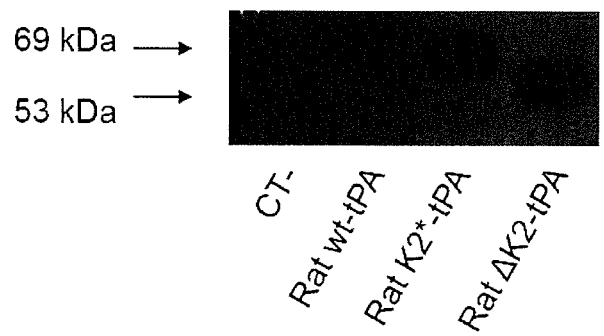
FIG. 4A-B. K2-related muteins have improved fibrinolytic properties. A) ΔK2-tPA and K2*-tPA reveal a fibrinolytic activity as wt-tPA when subjected to fibrin agarose zymography following non reduced SDS PAGE electrophoresis. B) In vitro evaluation of fibrinolytic activity using a platelet-poor plasma clot (PPP-clot). K2*-tPA and ΔK2-tPA muteins express improved global fibrinolytic efficiency compared to wt-tPA (26% and 51% respectively). Fibrinolytic activity was normalized to rat wt-tPA, using the half-time for clot lysis.
Figure 4B:
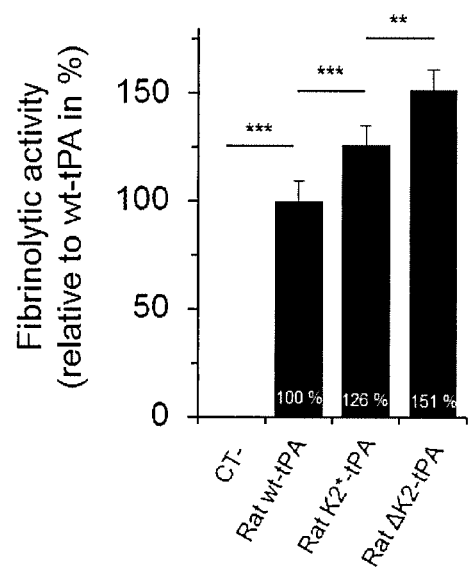

K2-related muteins were characterized toward their ability to initiate fibrinolysis on fibrin-agar plates as described in the methods section. ΔK2-tPA and K2*-tPA trigger activation of plasminogen into plasmin in the presence of fibrin as wt-tPA does (FIG. 4A). In vitro clot lysis assay, performed on platelet-poor human plasma clot (PPP-clot) as substrate, revealed that K2*-tPA and ΔK2-tPA displayed an enhanced fibrinolytic activity when compared to wt-tPA (+26% and +51% respectively) (FIG. 4B). To estimate their effect on NMDA receptor mediated neurotoxicity, pure cultures of cortical neurons (14 days in vitro) were subjected to 1 hour exposure of 50 μM NMDA either alone or in combination with either purified ΔK2-tPA or K2*-tPA (0.3 μM equivalent of their respective amidolytic activity) prior measure of the neuronal death 24 hours later. Although the rat wt-tPA leads to a 39% potentiation of NMDAR-mediated excitotoxicity (71% of neuronal death when compared to 51% with NMDA alone), an effect similar to what is observed for Actilyse®-containing human tPA (FIG. 5A; n=3, p<0.01), ΔK2-tPA and K2*-tPA (FIG. 5B; n=4, p<0.01) have no pro-neurotoxic profiles. Thus, the tryptophan 254, a constitutive amino-acid of the kringle 2 LBS of tPA is critical to mediate the pro-neurotoxicity of tPA. Accordingly, same experiments performed in the presence of ε-amino caproic acid (8-ACA), a lysine analog known to compete with the LBS of tPA, show that blockage of the LBS function prevented wild type tPA-induced potentiation of NMDAR-mediated neurotoxicity (FIG. 5C; n=5, p<0.01).

A Zymogenic tPA (sc*-tPA) Displays a Non Pro-Neurotoxic Profile.

The inventors have tested both the fibrinolytic activity and the pro-neurotoxicity of the non-cleavable form of rat tPA, sc*-tPA, generated and purified as described above. In contrast to its lack of intrinsic amidolytic activity (FIG. 3B-C), sc*-tPA remains fibrinolytic in the presence of fibrin (FIG. 6A) despite a lower activity to that of wt-tPA (−39%) (FIG. 6B). Then, this mutein was tested for its ability to influence NMDAR-mediated neurotoxicity in primary cultures of cortical neurons. Interestingly, sc*-tPA fails to potentiate NMDA receptors-dependent excitotoxicity when compared to wt-tPA (n=3, p<0.01) (FIG. 7).

Altogether, the inventors have generated and characterized a set of original fibrinolytics derived from tPA: a K2*-tPA (SEQ ID NO: 4) characterized by a higher fibrinolytic activity and a lack of pro-neurotoxicity and a sc*-tPA (SEQ ID NO: 8) characterized by both a lack of amydolytic activity and pro-neurotoxicity despite a conserved fibrinolytic activity. These in vitro data provide the bases of further studies to evaluate the efficacy of this new generation of fibrinolytics in experimental models of thrombosis, prior possible transfer to clinical applications.

EXAMPLE 2: HUMAN TPA MUTANTS

Material and Methods
Chemicals

N-methyl-D-aspartate (NMDA) was purchased from Tocris (Bristol, United Kingdom); Spectrofluor 444FL from American Diagnostica (ADF Biomedical, Neuville-sur-oise, France); 6-aminocaproic acid (s-ACA), Dulbecco's modified Eagle's medium (DMEM), poly-D-lysine, cytosine β-D-arabinoside and hygromycin B from Sigma-Aldrich (L'Isle d'Abeau, France). Lipofectamine 2000, foetal bovine and horse sera, laminin and the GeneArt® Site-Directed Mutagenesis System were from Invitrogen (Cergy Pontoise, France). tPA (Alteplase®) came from Boehringer-Ingleheim (Paris, France). Reteplase (Rapilysin) came from Actavis (Paris, France).

Construction of Wild-Type tPA in pcDNA5/FRT Vector.

The human tPA was amplified by PCR using primers: 5' GGCGCTAGCATGGATGCAATGAAGAGAGGGC 3' (SEQ ID NO:32) and 5' CCGGGCAAGCTTTTGCTTCAT-GTTGTCTTGAATCCAGTT 3' (SEQ ID NO:33) (with a 6×His tag at the N-terminal position of the mature protein). PCR products were inserted into a pcDNA5/FRT vector (Invitrogen, Cergy-Pontoise, France). Final construct was automatically sequenced.

Site-Directed Mutagenesis

Mutagenesis of hutPAwt was performed using GeneArt® Site-Directed Mutagenesis System and the following primers:

```
tPA K2* (W253R) of SEQ ID NO: 28:
                                        (SEQ ID NO: 34)
5' GCCAAGCCCCGGTGCCACGTGC 3'
and (SEQ ID NO: 35)
5' GCACGTGGCACCGGGGCTTGGC 3'.

tPA sc* (R275S) of SEQ ID NO: 29:
                                        (SEQ ID NO: 36)
5' GTACAGCCAGCCTCAGTTTAGCATCAAAGGAGGGC 3'
and (SEQ ID NO: 37)
5' AAACTGAGGCTGGCTGTACTGTCTCAGGCCGC 3'.

P125R point mutation of tPA of SEQ ID NO: 31:
                                        (SEQ ID NO: 38)
5' GCAGCGCGTTGGCCCAGAAGCGCTACAGCGGGC 3'
and (SEQ ID NO: 39)
5' CTTCTGGGCCAACGCGCTGCTGTTCCAGTTGG 3'.
```

Mutations were confirmed by sequence analysis.

Human Embryonic Kidney (HEK)-293 Cell Cultures and Stable Transfection Stable human embryonic kidney 293 cells transfected with the pFRT/lacZeo vector (HEK-FlpIn, Invitrogen) were grown in RPMI-1640 medium supplemented with 10% foetal bovine serum and 2 mM glutamine. Cells were transfected using lipofectamine 2000. Positive clones were isolated by hygromycine B selection. The quality of the transfection was assessed by RT-PCRq.

Bioreactor Production of the tPA-Related Mutants

To produce high yields of mutant genes, stable transfected HEK cells were grown in a laboratory-scale bioreactor CELLine AD 1000 (Dominique Dutscher SAS, Brumath, France).

Purification of 6×his Mutants

Purification was processed using nickel-nitrilotriacetic acid (Ni-NTA) metal-affinity chromatography matrice (Qiagen, Courtaboeuf, France). tPA mutants were then conditioned in a $NH_4HCO_3$ 0.5 M buffer and stored.

tPA Immunoblotting

Immunoblottings were performed using a polyclonal sheep antiserum raised against human tPA (1:5000) prepared at the National institute for agronomic research (INRA, Clermont-Theix, France) and a polyclonal rabbit antiserum raised against murine tPA (125 ng/μl), followed by incubation with the appropriate peroxidase-conjugated secondary antibody. Immunoblots were revealed with an enhanced chemoluminescence ECL Plus immunoblotting detection system (Perkin Elmer-NEN, Paris, France).

Amidolytic Activity Assay tPA variants were incubated in the presence of a fluorogenic substrate (5 μM) (Spectrofluor® FL444). The reaction was carried out at 37° C. in 50 mM Tris (pH 8.0) containing 150 mM NaCl in a total volume of 100 μL. The amidolytic activity was measured as the change in fluorescence emission at 440 nm (excitation at 360 nm).

Clot Lysis Time

Human plasma was obtained from citrated blood. Plasma was supplemented with 15 mM of calcium chloride and each of the tPA mutants at 400, 420, 440, 460, 480 and 500 I.U. The euglobulin fraction was recovered as described above, supplemented with 15 mM calcium chloride and 15, 20, 25, 30, 35 or 40 I.U. of the tPA muteins. The time to clot lysis was recorded by optical density measurements (A405 nm) at 37° C. by reference to the commercially available form of tPA (actilyse). Tests were performed in duplicate (from 3 independent experiments). Results are expressed as the time to obtain 50% clot lysis.

Neuronal Cell Culture

Neuronal cultures were prepared from foetal mice (embryonic day 15-16). Cortices were dissected and dissociated in DMEM, and plated on 24-well plates previously coated with poly-D-Lysine (0.1 mg/mL) and laminin (0.02 mg/mL). Cells were cultured in DMEM supplemented with 5% foetal bovine serum, 5% horse serum and 2 mM glutamine. Cultures were maintained at 37° C. in a humidified 5% $CO_2$ atmosphere. Cytosine β-D-arabinoside (10 μM) was added after 3 days in vitro (DIV) to inhibit glial proliferation. Various treatments were performed after 14 DIV.

Excitotoxic Neuronal Death

Excitotoxicity was induced by exposure of cortical neurons to NMDA (50 μM) in serum-free DMEM supplemented with 10 μM of glycine, for 1 hour. The different tPA variants were applied with NMDA when indicated. Neuronal death was quantified 24 hours later by measuring the activity of lactate dehydrogenase (LDH) released from damaged cells into the bathing medium by using a cytotoxicity detection kit (Roche Diagnostics; Mannheim, Germany). The LDH level corresponding to the maximal neuronal death was determined in sister cultures exposed to 200 μM NMDA (LDHmax). Background LDH levels were determined in sister cultures subjected to control washes (LDHmin). Experimental values were measured after subtracting LDHmin and then normalized to LDHmax–LDHmin in order to express the results in percentage of neuronal death relative to control.

Excitotoxic Lesion

Excitotoxic lesions were performed under isoflurane-induced anaesthesia in male swiss mice (25-30 g; CURB, Caen, France). Striatal injections (coordinates: 0.5 mm posterior, +2.0 mm lateral, −3.0 mm ventral to the bregma; Paxinos & Watson, 1995) of 12.5 nmol NMDA versus either NMDA/actilyse, NMDA/Opt-PA or NMDA/hutPA K2* (12.5 mM NMDA and 5 μM equivalent amidolytic activity of tPA; total volume of 1 μl) were performed after placing the animals under a stereotaxic frame. Injections were made using adapted needles (calibrated at 15 mm/μL; assistant ref 555/5; Hoecht, Sodheim-Rhoen, Germany) and removed 5 minutes later. After 24 hours, brains were MRI analysed.

Magnetic Resonance Imaging (MRI)

Experiments were carried out at 24 hours following excitotoxic lesions on a Pharmascan 7T (Bruker, Germany). T2-weighted images were acquired using a Multi-Slice Multi-Echo (MSME) sequences: TE/TR 51.3 ms/1700 ms with 70×70×350 μm3 spatial resolution. Lesion sizes were quantified on these images using ImageJ software (v1.45r).

Results

Generation of New Thrombolytics Originated from tPA.

The inventors have designed and generated six tPA mutants derived from the human tPA: (i) a human wild-type tPA named hutPA wt (SEQ ID NO: 27); (ii) a human tPA genetically engineered with complete deletion of its K2 domain (deletion of the amino acids 180 to 261), named hutPA ΔK2; (iii) a human tPA containing a tryptophan to arginine point mutation at position 253 (W253R, SEQ ID NO: 28), named hutPA K2*; (iv) an exclusive human single-chain tPA obtained by an arginine to serine point mutation at position 275 (R275S, ID SEQ NO: 29), named hutPA sc*; (v) a human tPA containing the double mutation W253R R275S, named Opt-PA (SEQ ID NO: 30); (vi) a human tPA containing the triple mutation P125R W253R R275S (SEQ ID NO: 31), named Opt-PA2. After PCR-induced appropriate deletion/mutation as described above, the corresponding 6× histidine-tagged cDNAs were inserted into a mammalian expression vector pcDNA5/FRT and stable transfected in HEK-293 cells expressing the Flp-In system (Invitrogen) for stable production of the corresponding recombinant proteins, as described in the methods section. Once purified using nickel affinity chromatography, the tPA mutants were subjected to SDS-PAGE electrophoresis and immunoblotting. Reteplase and activase were used as standards (FIG. 8). Interestingly, tPA mutants carrying the R275S point mutation are present under their exclusive single-chain form.

Biochemical Characterization of the Human Derived tPA Mutants.

The inventors have first evaluated the intrinsic proteolytic activity of each of these mutants. Thus amidolytic activity assay toward a fluorogenic substrate (Spectrofluor) (FIG. 9—LEFT) was performed. Our data reveal that sc*-tPA, Opt-PA and Opt-PA 2 show an amidolytic activity decreased by 10, 2.5 and 2 respectively. The mutants were characterized toward their ability to initiate fibrinolysis in models of in vitro clot assays performed on platelet-poor human plasma clot (PPP-clot) as substrate. These assays reveal that both Opt-PA and Opt-PA show similar potentiality to trigger fibrinolysis (FIG. 9—CENTER), even in the presence of the tPA' inhibitors (differences are no more than order of magnitude, FIG. 9—RIGHT).

R275S Point Mutation is not Sufficient to Abolish tPA-Related NMDA Receptors Mediated Neurotoxicity.

To estimate the effect of the tPA mutants hutPA sc* and Opt-PA 2 on NMDA receptor mediated neurotoxicity, pure cultures of cortical neurons (14 days in vitro) were subjected to 1 hour exposure of 50 μM NMDA either alone or in combination with the purified mutants (0.3 μM) prior measure of the neuronal death 24 hours later. Although actilyse leads to a 61% potentiation of NMDAR-mediated excitotoxicity (59% of neuronal death when compared to 37% with NMDA alone), a similar effect is observed for hutPA sc* (62% of neuronal cell death, FIG. 10; n=4, p<0.05). Thus the R275S point mutation is not sufficient by itself to abolish tPA-related NMDA receptors mediated neurotoxicity. The inventors also tested the triple mutant Opt-PA in the above experimental setting up. They observed a marked tendency (but not significant) to abolish tPA-related NMDA receptor mediated neurotoxicity (51% of neuronal cell death, n=4, p=0.08).

The Kringle 2-Related Human tPA Mutants Show a Non-Neurotoxic Profile.

hutPA K2* and Opt-PA were used in place of hutPA sc* and Opt-PA2 in the excitotoxic neuronal death assay (FIG. 11). Here, although actilyse leads to a 41% potentiation of NMDAR-mediated excitotoxicity (75% of neuronal death when compared to 53% with NMDA alone), hutPA K2* and Opt-PA do not promote NMDAR-mediated neurotoxicity (64% and 62% of neuronal cell death respectively, FIG. 11; n=4, p<0.05). Thus, the tryptophan 253, a constitutive amino-acid of the kringle 2 LBS of tPA is critical to mediate the pro-neurotoxicity of tPA. The two tPA mutants hutPA K2* and Opt-PA have an interesting non-neurotoxic profile.

Opt-PA does not Increase Neurotoxicity in an In Vivo Model of Striatal Lesion.

The inventors have then tested the neurotoxicity of both hutPA K2* and Opt-PA in a model of striatal lesion in vivo. As described in the method section, 12.5 mM of NMDA and 5 μM of the tPA variants are injected into the striatum of swiss mice. 24 hours after injection the lesion volume is measured using non-invasive MRI imaging (FIG. 12). Whereas actilyse leads to a 48% potentiation of NMDA-mediated excitotoxicity (5.36 $mm^3$ lesion volume % when compared to 3.62 $mm^3$ with NMDA alone), hutPA K2* has an heterogeneous neurotoxic effect (5.15 $mm^3$ lesion volume) and Opt-PA does not promote NMDA-mediated neurotoxicity (4.00 $mm^3$ lesion volume, FIG. 12; n=11, p<0.05)

Altogether, the inventors have generated and characterized a set of original fibrinolytics derived from human tPA.

From this set of mutants, Opt-PA (SEQ ID NO: 30) is characterized by a fibrinolytic activity similar to actilyse and a lack of pro-neurotoxicity in vitro and in vivo.

These data provide the bases of further studies to evaluate the efficacy of this new fibrinolytic in experimental models of thrombosis, prior possible transfer to clinical applications.

The invention claimed is:

1. A polynucleotide encoding for a protein selected from the group consisting of:
   i) a protein comprising sequence SEQ ID NO: 2 or SEQ ID NO:25, wherein said sequence comprises:
      a mutation A' consisting of the replacement of at least one of an amino acid selected from the group consisting of the aspartic acid at position 236, the aspartic acid at position 238, and the tryptophan at position 253 of SEQ ID NO: 2 or SEQ ID NO:25 by a hydrophilic amino acid selected from the group consisting of arginine, glutamic acid, lysine, asparagine, glutamine, serine, threonine, tyrosine and histidine, or the tryptophan at position 253 is replaced by aspartic acid, or
      a mutation B consisting of the replacement of arginine in position 275 of SEQ ID NO: 2 or SEQ ID NO:25 by serine, or
      a double mutation A' and B consisting of the replacement of at least one of an amino acid selected from the group consisting of the aspartic acid at position 236, the aspartic acid at position 238, and the tryptophan at position 253 of SEQ ID NO: 2 or SEQ ID NO:25 by a hydrophilic amino acid chosen from arginine, glutamic acid, lysine, asparagine, glutamine, serine, threonine, tyrosine and histidine, or the tryptophan at position 253 is replaced by aspartic acid, and the replacement of arginine in position 275 of SEQ ID NO: 2 or SEQ ID NO:25 by serine,
   ii) a protein comprising a sequence having at least 80% identity with SEQ ID NO: 2 over its whole length or SEQ ID NO:25 over its whole length, said protein comprising mutation A', mutation B, or mutation A' and B, and
   iii) a protein consisting of a fragment of SEQ ID NO:2, said fragment consisting of the Kringle 2 domain, the catalytic domain, and mutation A', mutation B, or mutation A' and B.

2. An expression vector comprising a polynucleotide according to claim 1.

3. An isolated host cell comprising an expression vector according to claim 2.

4. An isolated host cell comprising a polynucleotide according to claim 1.

\* \* \* \* \*